United States Patent
Blackaby et al.

(10) Patent No.: US 8,163,956 B2
(45) Date of Patent: Apr. 24, 2012

(54) INHIBITORS OF GLYT1 TRANSPORTERS

(75) Inventors: Wesley Peter Blackaby, Epping (GB); Ian Thomas Huscroft, Bishops Stortford (GB); Linda Elizabeth Keown, Belfast (GB); Richard Thomas Lewis, Framingham, MA (US); Piotr Antoni Raubo, West Bridgford (GB); Leslie Joseph Street, Newport Beach, CA (US); Christopher George Thomson, Billinghurst (GB); Joanne Thomson, Cambridge (GB)

(73) Assignee: Merck Sharp & Dohme Corp., Rahway, NJ (US)

( * ) Notice: Subject to any disclaimer, the term of this patent is extended or adjusted under 35 U.S.C. 154(b) by 250 days.

(21) Appl. No.: 11/922,074

(22) PCT Filed: Jun. 13, 2006

(86) PCT No.: PCT/GB2006/002156
§ 371 (c)(1),
(2), (4) Date: Feb. 11, 2009

(87) PCT Pub. No.: WO2006/134341
PCT Pub. Date: Dec. 21, 2006

(65) Prior Publication Data
US 2009/0286765 A1 Nov. 19, 2009

(30) Foreign Application Priority Data

Jun. 13, 2005 (GB) .................................. 0511903.7
Aug. 11, 2005 (GB) .................................. 0516496.7
Dec. 12, 2005 (GB) .................................. 0525124.4

(51) Int. Cl.
C07C 303/00 (2006.01)
C07C 233/00 (2006.01)
C07C 237/00 (2006.01)
C07C 323/00 (2006.01)
A61K 31/16 (2006.01)
A61K 31/165 (2006.01)

(52) U.S. Cl. .......... 564/86; 564/168; 564/189; 564/192; 514/613; 514/617; 514/625

(58) Field of Classification Search .................. 549/568; 514/428
See application file for complete search history.

(56) References Cited

FOREIGN PATENT DOCUMENTS

| WO | WO 99/52519 | 10/1999 |
|---|---|---|
| WO | WO 2004/013100 | 2/2004 |
| WO | WO 2005/046601 | 5/2005 |
| WO | WO 2005/090353 | 9/2005 |
| WO | WO2005/094514 | 10/2005 |
| WO | WO2005/107469 | 11/2005 |
| WO | WO2005/110983 | 11/2005 |
| WO | WO2006/039221 | 4/2006 |
| WO | WO2006/067529 | 6/2006 |
| WO | WO2006/131711 | 12/2006 |
| WO | WO2006/131713 | 12/2006 |

OTHER PUBLICATIONS

Hcaplus 1993:408508, "Amino acid derivative anticonvulsant", Kohn et. al., 1992.*
Hcaplus 1972:475204, "Blood sugar-depressing arylsulfonylsemicarbazides containing heterocyclic acylamino groups", Plumpe, et. al., 1972.*
Hcaplus 1988:437733, "Preparation and formulatoin of N-(2-aminoethyl)acetamides and propionamides as analgesics", Costello, Gerard, 1988.*
Hardman, J., ed, Goodman and Gilman's The Pharmacological Basis of Therdapeutics 1996 McGraw-Hill, p. 44.*
Wolkenberg, S. et al Curr Top Med Chem 2010, 10, pp. 170-186.*
Biere, et al., "Blood Glucose Lowering Sulfonamides with Asymmetric Carbon Atoms," Journal of Medicinal Chemistry, vol. 7, No. 7, 1974, pp. 716-721.

* cited by examiner

Primary Examiner — Janet Andres
Assistant Examiner — Heidi Reese
(74) Attorney, Agent, or Firm — Susan L. Hess; Gerard M. Devlin

(57) ABSTRACT

A compound of the formula (I): wherein $R^1$, $R^2$, $R^3$, $R^4$, Ar, A, n and m are defined herein, is disclosed as a GlyT1 inhibitor; pharmaceutical compositions containing the compound of the formula (I) are also disclosed as are their use in medicine, for example in the treatment of schizophrenia.

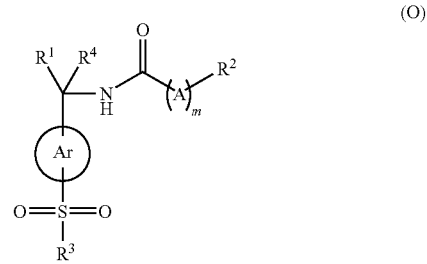

11 Claims, No Drawings

INHIBITORS OF GLYT1 TRANSPORTERS

CROSS REFERENCE TO RELATED APPLICATIONS

This application is a U.S. National Phase application under 35 U.S.C. §371 of PCT Application No. PCT/GB2006/002156, filed Jun. 13, 2006, which claims priority under 35 U.S.C. §119 from GB Application No. 0511903.7, filed Jun. 13, 2005; GB Application No. 0516496.7, filed Aug. 11, 2005; and GB Application No. 0525124.4, filed Dec. 12, 2005.

BACKGROUND OF THE INVENTION

Schizophrenia is a debilitating psychiatric disorder characterized by a combination of negative (blunted affect, withdrawal, anhedonia) and positive (paranoia, hallucinations, delusions) symptoms as well as marked cognitive deficits. While the etiology of schizophrenia is currently unknown, the disease appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia (Jentsch J D and Roth R H, 1999 Neuropsychopharmacology, 20:201).

Fast glutamatergic transmission in the mammalian central nervous system is primarily mediated by the excitatory amino acid glutamate acting on ionotropic glutamate receptors (iGluRs). The iGluRs are comprised of three major subclasses, including the α-amino-3-hydroxy-5-methyl-4-isoxazolepropionic acid (AMPA), kainate, and NMDA receptor subtypes (Hollmann M and Heinemann S, 1994, Annu. Rev. Neurosci. 17:31). These three subclasses are multimeric ligand-gated cation channels which open in response to glutamate binding to induce a depolarizing excitatory post synaptic current. Molecular cloning has revealed that the NMDA receptor family is composed of two primary subunits, NR1 and NR2. In addition a novel inhibitory subunit which is developmentally regulated termed NR3 has been recently described. A high degree of molecular diversity exists within each set of subunits. To date, only one NR1 subunit gene has been cloned; however, alternative splicing of the NR1 gene can produce eight different subunits. In contrast, 4 genes have been cloned for the NR2 subunit (NR2A, NR2B, NR2C, and NR2D), some of which exhibit alternative splicing (Hollmann M and Heinemann S, 1994, Annu. Rev. Neurosci. 17:31). These multiple subunits form heteromeric glutamate-gated ion channels. While the precise subunit stoichiometry of the naturally occurring receptor remains unknown, both the NR1 and NR2 subunits are required for the expression of functionally active receptor-channel complexes in mammalian expression systems. Activation of the NMDA receptor requires the binding of both glutamate and glycine (Johnson J W and Ascher P, 1987, Nature 325:529). Interestingly, the binding sites for these two co-agonists exist on separate subunits as determined by site-directed mutagenesis studies (Laube B, Hirai H, Sturgess M, Betz H and Kuhse J, 1997, Neuron 18:493). On the NR2A and NR2B subunits, a binding pocket for glutamate is formed by interactions between the N-terminus of the receptor and the extracellular loops. Analogous experiments have placed the glycine binding site in a homologous region of the NR1 subunit (Kuryatov A, Laube B, Betz H and Kuhse J, 1994, Neuron 12:1291). Depending on the actual subunit composition, glutamate and glycine activate the NMDA receptor with EC50 values in the high nanomolar to low micromolar range. In addition, the pore of the NMDA receptor is impermeable to magnesium. Under normal resting conditions, extracellular magnesium can bind to a site within the pore and produce a magnesium block of the channel. This magnesium block imparts a strong voltage dependence to the channel which allows the NMDA receptor to act as a coincidence detector requiring the binding of glutamate, glycine, and the occurrence of postsynaptic depolarization before conducting current Of particular interest is the finding that the psychotomimetic drugs MK-801, PCP, and ketamine all act as open channel blockers of the NMDA receptor-channel by binding to a site that overlaps with the magnesium binding site. It is apparent that the rich diversity of NMDA receptor subunits and regulatory sites provides for a complex assortment of physiologically and pharmacologically distinct heteromeric receptors making the NMDA receptor an ideal target for the design of novel therapeutic compounds.

The NMDA receptor plays a critical role in a variety of neurophysiological phenomena, including but not limited to synaptic plasticity, cognition, attention and memory (Bliss T and Collingridge W, 1993, Nature 361:31; Morris R G M et al., 1986, Nature 319:774). Psychotomimetic drugs constitute a wide class of drugs including psychomotor stimulants (cocaine, amphetamine), hallucinogens (LSD), and NMDA receptor antagonists (PCP, ketamine). Of these, only the NMDA receptor antagonists appear to elicit a robust induction of the positive, negative, and cognitive symptoms of schizophrenia. Controlled studies of ketamine-induced psychosis inhuman subjects, as well as observations of symptoms from patients abusing PCP as a recreational drug, have produced a convincing list of similarities between NMDA receptor antagonist-induced psychosis and schizophrenia (Jentsch J D and Roth R H, 1999 Neuropsychopharmacology, 20:201). NMDA-receptor antagonists faithfully mimic the symptoms of schizophrenia to the extent that it is difficult to differentiate the two in the clinic. In addition, NMDA receptor antagonists can exacerbate the symptoms in schizophrenics, and can trigger the re-emergence of symptoms in stable patients. Finally, the finding that NMDA receptor co-agonists such as glycine, D-cycloserine, and D-serine produce benefits in schizophrenic patients implicates NMDA receptor hypofunction in this disorder, and indicate that increasing NMDA receptor activation may provide a therapeutic benefit (Leiderman E et al., 1996, Biol. Psychiatry 39:213, Javitt D C et al., 1994, Am. J. Psychiatry 151:1234, Heresco-Levy U, 2000, Int. J. Neuropsychopharmacol. 3:243, Tsai G et al., 1998, Biol. Psychiatry 44:1081). A large number of studies in animal models lend support to the NMDA hypofunction hypothesis of schizophrenia. Recent generation of a mutant mouse expressing only 5% of normal levels of the NMDA NR1 subunit have shown that this decrease in functional NMDA receptors induces a state very similar to that observed in other animal models of schizophrenia (Mohn A R et al., 1999, Cell 98:427). Besides schizophrenia, dysfunction of glutamatergic pathways has been implicated in a number of disease states in the human central nervous system (CNS) including but not limited to cognitive deficits, dementia, Parkinson disease, Alzheimer disease and bipolar disorder.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses. Clinical trials in which high doses of glycine were administered orally as an add-on to standard neuroleptic therapy showed an improvement of the symptoms of schizophrenia patients (Javitt et al. Int. 3. Neuropsychopharmacol. (2001) 4: 385-391). One way to increase synaptic glycine levels without administering exogenous glycine is to inhibit its removal from the synapse. Evidence that this approach would be useful in treating schizophrenia comes from a double-blind placebo controlled study in which sarcosine was administered to patients suffering from schizophrenia, but who were poorly responsive to antipsychotic drugs. A beneficial effect was observed on positive, negative and cognitive symptoms, indicating that inhibition of glycine re-uptake is a reasonable approach to the treatment of schizophrenia.

Two specific glycine transporters, GlyT1 and GlyT2 have been identified and shown to belong to the Na+/Cr− dependent family of neurotransmitter transporters which includes taurine, γ-aminobutyric acid (GABA), proline, monoamines and orphan transporters (Smith K E et al., 1992, Neuron 8:927; Borowsky B et al., 1993, Neuron 10:851; Liu Q R et al., 1993, J. Biol. Chem. 268:22802; Kim K M et al., 1994, Mol. Pharmacol. 45:608; Morrow J A et al., 1998, FEBS Lett. 439:334; Nelson N, 1998, J. Neurochem. 71:1785). GlyT1 and GlyT2 have been isolated from different species and shown to have only 50% identity at the amino acid level. They also have a different pattern of expression in mammalian central nervous system with GlyT2 being expressed in spinal cord, brainstem and cerebellum and GlyT1 present in these regions as well as forebrain areas such as cortex, hippocampus, septum and thalamus (Smith K E et al., 1992, Neuron 8:927; Borowsky B et al., 1993, Neuron 10:851; Liu Q R et al., 1993, J. Biol. Chem. 268:22802). At the cellular level, GlyT2 has been reported to be expressed by glycinergic nerve endings in rat spinal cord whereas GlyT1 appears to be preferentially expressed by glial cells (Zafra F et al., 1995, J. Neurosci. 15:3952). These expression studies have led to the conclusion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat (Bergeron R et al., 1998, PNAS USA 95:15730; Kinney G et al., 2003, J. Neurosci. 23:7586). Furthermore, NFPS has been reported to enhance pre-pulse inhibition in mice, a measure of sensory gating that is known to be deficient in schizophrenia patients (Kinney G et al., 2003, J. Neurosci. 23:7586). These physiological effects of GlyT1 in forebrain regions together with clinical reports showing the beneficial effects of GlyT1 inhibitor sarcosine in improving symptoms in schizophrenia patients (Tsai and Coyle WO99/52519) indicate that selective GlyT1 uptake inhibitors represent a new class of antipsychotic drugs.

SUMMARY OF THE INVENTION

The present invention is directed to compounds that inhibit the glycine transporter GlyT1 and which are useful in the treatment of neurological and psychiatric disorders associated with glutamatergic neurotransmission dysfunction and diseases in which the glycine transporter GlyT1 is involved.

DETAILED DESCRIPTION OF THE INVENTION

The present invention is directed to compounds of the formula (O):

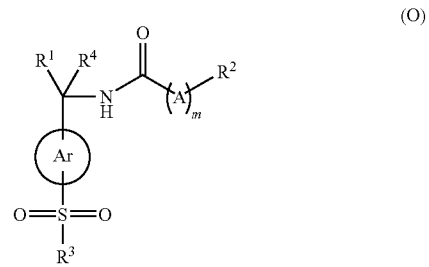

wherein the Ar ring is an optionally substituted phenyl or 5- or 6-membered aromatic ring containing one two or three hetero atoms selected from nitrogen, oxygen and sulphur with the proviso that the two side chains on the Ar ring are not attached to adjacent ring atoms;

$R^1$ is —$CH_2)_n$—$R^{1a}$, wherein n is independently 0-6, and $R^{1a}$ is selected from the group consisting of:
  (1) $C_{1-6}$alkyl or $C_{1-6}$alkenyl, which is unsubstituted or substituted with 1-6 halogen, hydroxyl or —$NR^{10}R^{11}$,
  (2) phenyl substituted with $R^{2a}$, $R^{2b}$ and $R^{2c}$,
  (3) heterocycle substituted with $R^{2a}$, $R^{2b}$ and $R^{2c}$,
  (4) $C_{3-6}$cycloalkyl, which is unsubstituted or substituted with $C_{1-6}$alkyl, 1-6 halogen, hydroxy or —$NR^{10}R^{11}$,
  (5) —O—$C_{1-6}$alkyl, which is unsubstituted or substituted with 1-6 halogen, hydroxy or —$NR^{10}R^{11}$,
  (6) —$CO_2R^9$,
    wherein $R^9$ is independently selected from:
    (a) hydrogen,
    (b) —$C_{1-6}$alkyl, which is unsubstituted or substituted with 1-6 fluoro,
    (c) benzyl, and
    (d) phenyl,
  (7) —$NR^{10}R^{11}$,
    wherein $R^{10}$ and $R^{11}$ are independently selected from:
    (a) hydrogen,
    (b) —$C_{1-6}$alkyl, which is unsubstituted or substituted with hydroxy, 1-6 fluoro or —$NR^{12}R^{13}$, where $R^{12}$ and $R^{13}$ are independently selected from hydrogen and —$C_{1-6}$alkyl,
    (c) —$C_{3-6}$cycloalkyl, which is unsubstituted or substituted with hydroxy, 1-6 fluoro or —$NR^{12}R^{13}$,
    (d) benzyl,
    (e) phenyl, and
  (8) —$CONR^{10}R^{11}$;

$R^2$ is selected from the group consisting of:
  (1) phenyl, which is substituted with $R^{2a}$, $R^{2b}$ and $R^{2c}$,
  (2) heterocycle, which is substituted with $R^{2a}$, $R^{2b}$ and $R^{2c}$,
  (3) $C_{1-8}$alkyl, which is unsubstituted or substituted with 1-6 halogen, hydroxy, —$NR^{10}R^{11}$, phenyl or heterocycle, where the phenyl or heterocycle is substituted with $R^{2a}$, $R^{2b}$ and $R^{2c}$,
  (4) $C_{3-6}$cycloalkyl, which is unsubstituted or substituted with 1-6 halogen, hydroxy or —$NR^{10}R^{11}$, and
  (5) —$C_{1-6}$alkyl-($C_{3-6}$cycloalkyl), which is unsubstituted or substituted with 1-6 halogen, hydroxy or —$NR^{10}R^{11}$;

$R^{2a}$, $R^{2b}$ and $R^{2c}$ are independently selected from the group consisting of:
(1) hydrogen,
(2) halogen,
(3) —$C_{1-6}$alkyl, which is unsubstituted or substituted with:
 (a) 1-6 halogen,
 (b) phenyl,
 (c) $C_{3-6}$cycloalkyl, or
 (d) —$NR^{10}R^{11}$,
(4) —O—$C_{1-6}$alkyl, which is unsubstituted or substituted with 1-6 halogen,
(5) hydroxy,
(6) —$SCF_3$,
(7) —$SCHF_2$,
(8) —$SCH_3$,
(9) —$CO_2R^9$,
(10) —CN,
(11) —$SO_2R^9$,
(12) —$SO_2$—$NR^{10}R^{11}$,
(13) —$NR^{10}R^{11}$,
(14) —$CONR^{10}R^{11}$, and
(15) —$NO_2$;

$R^3$ is selected from the group consisting of:
(1) $C_{1-6}$alkyl, which is unsubstituted or substituted with 1-6 halogen, hydroxyl, —$NR^{10}R^{11}$, or heterocycle, which is substituted with $R^{2a}$, $R^{2b}$ and $R^{2c}$,
(2) $C_{3-6}$cycloalkyl, which is unsubstituted or substituted with 1-6 halogen, hydroxyl or —$NR^{10}R^{11}$,
(3) —$C_{1-6}$alkyl-($C_{3-6}$cycloalkyl), which is unsubstituted or substituted with 1-6 halogen, hydroxy or —$NR^{10}R^{11}$,
(4) —$NR^{10}R^{11}$, and
(5) heterocycle, which is substituted with $R^{2a}$, $R^{2b}$ and $R^{2c}$;

$R^4$ is selected from the group consisting of:
(1) hydrogen, and
(2) $C_{1-6}$alkyl, which is unsubstituted or substituted with halogen or hydroxyl;

A is selected from the group consisting of:
(1) —O—, and
(2) —$NR^{10}$—;

m is zero or one, whereby when m is zero $R^2$ is attached directly to the carbonyl and with the proviso that when $R^1$ is methyl, $R^3$ is not methyl;
and pharmaceutically acceptable salts thereof and individual enantiomers and diastereomers thereof.

Suitably, when Ar is an aromatic ring containing hetero atoms, there is a maximum of one hetero atom other than nitrogen. Suitable aromatic heterocycles are those containing one five- or six membered rings included within the definition "heteroaryl" as hereinafter defined. Most suitably, Ar is phenyl or a six-membered heteroaromatic ring such as pyridine or pyrimidine or a triazole ring. Preferably, the side chains on Ar are para to each other. In one embodiment Ar is unsubstituted. In a further embodiment Ar is substituted by a $C_{3-6}$cycloalkyl group such as a cyclopropyl group, a $C_{1-6}$alkyl group, suitably a $C_{1-4}$alkyl group such as methyl, which is unsubstituted or substituted with fluorine, or Ar is substituted by halo, for example fluoro or chloro and preferable fluoro. When Ar is a triazole ring, one of the ring nitrogen atoms is suitably substituted by a methyl group.

In one embodiment of the present invention, the compound of the formula (0) is a compound of the formula (I):

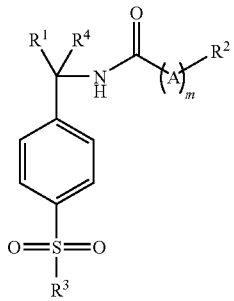

wherein $R^1$, $R^2$, $R^3$, $R^4$, A, n and m are defined herein or a pharmaceutically acceptable salt thereof or individual enantiomer or diastereoisomer therefore.

In an embodiment, the present invention includes compounds wherein $R^1$ is selected from the group consisting of $(CH_2)_nR^{1a}$ wherein $R^{1a}$ is $C_{3-6}$ cycloalkyl, which is unsubstituted or substituted with $R^{2a}$, $R^{2b}$ and $R^{2c}$. In one embodiment, suitably n is 1 and $R^{1a}$ is unsubstituted $C_{3-6}$ cycloalkyl, preferably cyclopropyl or cyclobutyl. In a further embodiment, suitably n is 0 and $R^{1a}$ is unsubstituted $C_{3-6}$ cycloalkyl, preferably cyclopropyl or cyclobutyl. In another embodiment $R^1$ is tertiary butyl.

An embodiment of the present invention includes compounds of the formula Ia:

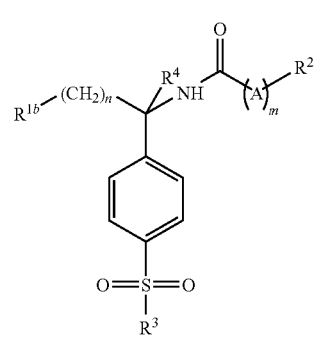

wherein $R^{1b}$ is a $C_{3-4}$ cycloalkyl, which is unsubstituted or substituted with $R^{2a}$, $R^{2b}$ and $R^{2c}$ and $R^2$, $R^{2a}$, $R^{2b}$, $R^{2c}$, $R^3$, $R^4$, A, n and m are defined herein or a pharmaceutically acceptable salt thereof or individual enantiomer or diastereoisomer therefore. Suitably n is 1 and $R^{1b}$ is unsubstituted $C_{3-6}$ cycloalkyl, preferably cyclopropyl or cyclobutyl.

Further embodiments of the present invention include compounds wherein $R^1$ is heterocycle substituted with $R^{2a}$, $R^{2b}$ and $R^{2c}$. The heterocycle is preferably an unsaturated heterocyclic moiety, for example a nitrogen containing unsaturated heterocycle such as pyridyl and $R^{2a}$ and $R^{2b}$ are hydrogen and $R^{2c}$ is hydrogen or fluorine or a saturated heterocyclic moiety, for example a nitrogen containing saturated heterocycle such as piperidinyl, or pyrrolidinyl which is unsubstituted or substituted with $R^{2a}$ and $R^{2b}$ and $R^{2c}$ is hydrogen wherein $R^{2a}$ and $R^{2b}$ are independently selected from the group consisting of $C_{1-6}$alkyl, 1-6 halogen, hydroxy, —O—$C_{1-6}$alkyl, or —$NR^{10}R^{11}$, pyranyl, which is unsubstituted or substituted with $C_{1-6}$alkyl, 1-6 halogen, hydroxy, —O—$C_{1-6}$alkyl, or —$NR^{10}R^{11}$, pyrrolyl, which is unsubstituted or substituted with $C_{1-6}$alkyl, 1-6 halogen, hydroxy, —O—$C_{1-6}$alkyl, or —$NR^{10}R^{11}$, or azabicyclo[2.2.1]heptanyl, which is unsubstituted or substituted with $C_{1-6}$alkyl, 1-6 halogen, hydroxy, —O—$C_{1-6}$alkyl, or —$NR^{10}R^{11}$ Suitably, when $R^1$ is a saturated heterocyclic moiety this is preferably piperidinyl, pyrrolidinyl or azabicyclo[2.2.1]heptanyl each optionally substituted by $C_{1-6}$ alkyl.

Thus, a further embodiment of the present invention provides compounds of the formula Ib:

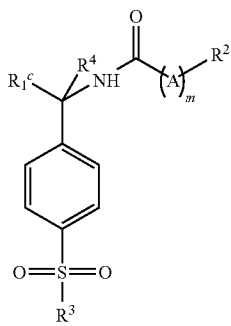

Ib wherein $R^{1c}$ is a saturated heterocycle, which is unsubstituted or substituted with $R^{2a}$, $R^{2b}$ and $R^{2c}$ and $R^2$, $R^{2a}$, $R^{2b}$, $R^{2c}$, $R^3$, $R^4$, A, n and m are defined herein or a pharmaceutically acceptable salt thereof or individual enantiomer or diastereoisomer therefore. Suitably, $R^{1c}$ is piperidinyl, pyrrolidinyl or azabicyclo[2.2.1]heptanyl each optionally substituted by $C_{1-6}$ alkyl.

In an alternative embodiment, $R^{1c}$ is a $C_{3-6}$cycloalkyl group which is unsubstituted or substituted with 1-6 halogen, preferably fluorine, or with an $C_{1-6}$alkoxy group, a methyl group optionally substituted by $C_{3-4}$cycloalkyl or by one or two further methyl groups or by a group —$NR^{10}R^{11}$ wherein $R^{10}$ and $R^{11}$ are independently selected from hydrogen or —$C_{1-6}$alkyl, preferably methyl or ethyl, or $R^{1c}$ is a phenyl group.

An embodiment of the present invention includes compounds wherein $R^4$ is $C_{1-3}$alkyl or hydrogen.

Also within this embodiment, the present invention includes compounds wherein $R^4$ is hydrogen.

An embodiment of the present invention includes compounds wherein m is zero.

Within this embodiment, the present invention includes compounds of the formula Ic:

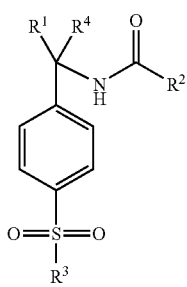

Ic wherein $R^1$, $R^2$, $R^3$, and $R^4$ are defined herein;
or a pharmaceutically acceptable salt thereof or an individual enantiomer or diastereomer thereof.

Further within this embodiment, the present invention includes compounds wherein $R^2$ is selected from the group consisting of:

(1) phenyl, which is substituted with $R^{2a}$, $R^{2b}$ and $R^{2c}$,
(2) heterocycle, such as pyridyl, pyrimidinyl or thienyl, which is substituted with $R^{2a}$, $R^{2b}$ and $R^{2c}$,
(3) $C_{1-8}$-alkyl, which is unsubstituted or substituted with 1-6 halogen, phenyl or —$NR^{10}R^{11}$, where the phenyl is substituted with $R^{2a}$, $R^{2b}$ and $R^{2c}$,
(4) $C_{3-6}$cycloalkyl, which is unsubstituted or substituted with 1-6 halogen, hydroxy or —$NR^{10}R^{11}$, and $R^{2a}$, $R^{2b}$ and $R^{2c}$ are independently selected from the group consisting of:

(1) hydrogen,
(2) halogen,
(3) —$C_{1-6}$alkyl,
(4) —O—$C_{1-6}$alkyl,
(5) —$CF_3$,
(6) —$OCF_3$,
(7) —$OCHF_2$,
(8) $SCF_3$,
(9) —$SCHF_2$, and
(10) —$NH_2$.

Also further within this embodiment, the present invention includes compounds wherein $R^2$ is phenyl or thienyl substituted by $R^{2a}$, $R^{2b}$ and $R^{2c}$ as hereinbefore defined:

Within this embodiment the present invention includes compounds of the formula Id:

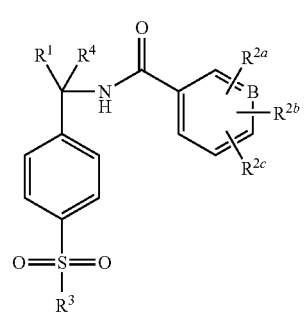

Id wherein $R^1$, $R^3$, and $R^4$ are defined herein, B is CH or N and $R^{2a}$, $R^{2b}$ and $R^{2c}$ are selected from hydrogen, fluoro, chloro, bromo, $OCH_3$, $CF_3$, $OCF_3$ and $NH_2$, and preferably selected from hydrogen, fluoro, chloro, bromo and $CF_3$; and pharmaceutically acceptable salts thereof and individual enantiomers and diastereomers thereof. In one embodiment of this invention, B is CH. In a further aspect of this invention, B is N.

Within this embodiment, the present invention includes compounds of the formula Id'

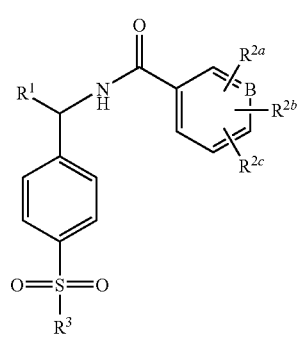

Id' wherein B, $R^1$, $R^{2a}$, $R^{2b}$, $R^{2c}$ and $R^3$ are defined herein; and pharmaceutically acceptable salts thereof and individual enantiomers and diastereomers thereof.

Also within this embodiment, the present invention includes compounds of the formula Id":

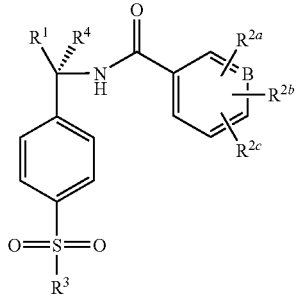

Id"

wherein B, $R^1$, $R^{2a}$, $R^{2b}$, $R^{2c}$, $R^3$ and $R^4$ are defined herein; and pharmaceutically acceptable salts thereof and individual enantiomers and diastereomers thereof.

An embodiment of the present invention includes compounds wherein $R^3$ is a group $R^{3a}$ and $R^{3a}$ is a heterocycle as defined herein which is substituted with $R^{2a}$, $R^{2b}$ and $R^{2c}$. Preferred heterocyclic groups $R^{3a}$ include unsaturated heterocycles. Preferably the unsaturated heterocyle will be a six-membered ring containing one or more nitrogen atoms, for example pyridine, or a five-membered ring containing a sulphur atom or one to three nitrogen atoms, and preferably two or three nitrogen atoms.

Most suitably $R^{3a}$ is a five-membered unsaturated heterocycle having one, two or three hetero atoms selected from one, two or three nitrogen atoms and additionally optionally an oxygen or sulphur atom that is linked to the sulphonyl group through one of the heterocycle's carbon atoms.

Preferably $R^{3a}$ is a group

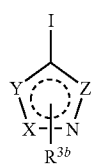

wherein at least one of X, Y and Z is nitrogen and one of the other groups is nitrogen, the third position being carbon; and $R^{3b}$ is hydrogen or $C_{1-6}$alkyl, preferably methyl or $R^{3a}$ is pyridine.

Most preferably $R^{3a}$ is a group:

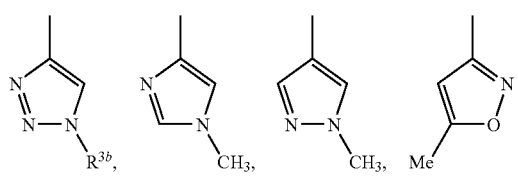

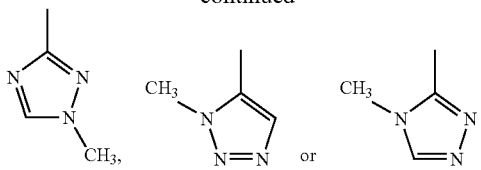

and $R^{3b}$ is hydrogen or methyl.

The unsaturated heterocycle may be unsubstituted or substituted by one or two halogen atoms or $C_{1-4}$ alkyl or $C_{1-6}$ haloalkyl groups. Preferably the unsaturated heterocycle is unsubstituted or substituted with one or two methyl or ethyl groups.

In another embodiment, $R^3$ is a $C_{1-4}$ alkyl group optionally substituted by a cyclopropyl group or a group $NR^{14}R^{15}$ wherein $R^{14}$ is hydrogen or a $C_1$— alkyl group and $R^{15}$ is a $C_{1-6}$ alkyl group or $R^{14}$ and $R^{15}$ together with the nitrogen atom to which they are attached form a four to six membered heterocyclic ring.

A preferred group of compounds of the formula (I) is that of the formula Ie:

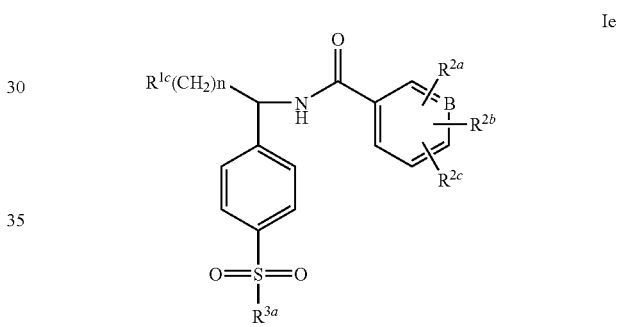

Ie wherein n, B, $R^{1c}$ and $R^{2a}$, $R^{2b}$ and $R^{2c}$ are as hereinbefore defined and $R^{3a}$ is an unsaturated heterocyle optionally substituted by a halogen or a $C_{1-6}$ alkyl or $C_{1-6}$ haloalkyl group.

n is preferably 0 or 1.

Preferred values of $R^{1c}$ are as hereinbefore defined.

$R^{2a}$, $R^{2b}$, $R^{2c}$ are preferably hydrogen, $CF_3$ or halogen, suitably chlorine or fluorine. Preferably only one of $R^{2a}$, e, $R^{2c}$ is hydrogen.

$R^{3a}$ is preferably a six-membered heterocyle containing one or more nitrogen atoms for example pyridine, or a five-membered heterocycle containing a sulphur or oxygen atom and/or one to three nitrogen atoms and preferably two to three nitrogen atoms, wherein the heterocyclic ring is optionally substituted by one or two halogen atoms or $C_{1-6}$ alkyl or $C_{1-6}$ haloalkyl groups, such as methyl or ethyl.

The heterocycle will preferably be connected to the sulphonyl group through a ring carbon atom.

Preferred heterocycles include five-membered unsaturated heterocycles such as triazolyl, pyrazolyl and imidazolyl.

The substituents on the heterocycle ring may be attached to ring carbon and or ring nitrogen atoms (in the case of nitrogen containing heterocycles).

A further preferred group of compounds of the formula (I) is that of the formula:

If

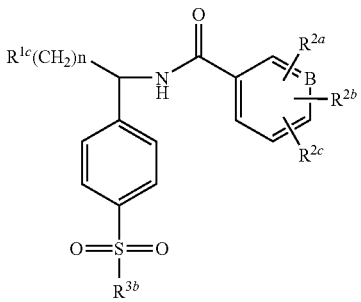

wherein n, B, $R^{1c}$ and $R^{2a}$, $R^{2b}$ and $R^{2c}$ are as hereinbefore defined and $R^{3b}$ is a $C_{1-4}$ alkyl group optionally substituted by a cyclopropyl group.

n is preferably 0 or 1.

Preferred values of $R^{1c}$ are as hereinbefore defined.

$R^{2a}$, $R^{2b}$, $R^{2c}$ are preferably hydrogen, methyl, $CF_3$ or halogen, suitably chlorine or fluorine. Preferably only one of $R^{2a}$, $R^{2b}$, $R^{2c}$ is hydrogen.

$R^{3b}$ is preferably propyl or cyclopropylmethyl.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more chiral centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl, A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof. The heterocycle may be bridged by a (1-3 alkylene group to form, for example, an azabicycloalkanyl group such as an azabicyclo[2.2.1]heptanyl group.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-diethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of inhibiting the glycine transporter GlyT1 activity in a patient such as a mammal in need of such inhibition comprising the administration of an effective amount of the compound. The present invention is directed to the use of the compounds disclosed herein as inhibitors of the glycine transporter GlyT1 activity. In addition to primates, especially humans, a variety of other mammals can be treated according to the method of the present invention.

The present invention is further directed to a method for the manufacture of a medicament for inhibiting glycine transporter GlyT1 activity in humans and animals comprising combining a compound of the present invention with a pharmaceutical carrier or diluent.

The subject treated in the present methods is generally a mammal, preferably a human being, male or female, in whom inhibition of glycine transporter GlyT1 activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibiting the glycine transporter activity, in particular GlyT1 activity, may be demonstrated by methodology known in the art. Human placental choriocarcinoma cells (JAR cells (ATCC No. HTB-144)) endogenously expressing GlyT1 were cultured in 96-well Cytostar scintillating microplates (Amersham Biosciences) in RPMI 1640 medium containing 10% fetal calf serum in the presence of penicillin (100 micrograms/milliliter) and streptomycin (100 micrograms/milliliter). Cells were grown at 37° C. in a humidified atmosphere of 5% CO2 for 40-48 hours before the assay. Culture medium was removed from the Cytostar plate, and JAR cells were incubated with 30 microliters of TB1A buffer (120 mM NaCl, 2 mM KCl, 1 mM $CaCl_2$, 1 mM $MgCl_2$, 10 mM HEPES, 5 mM L-alanine, pH 7.5 adjusted with Tris base) with or without the compounds of the present invention for 1 minute. Then 30 microliters of $[^{14}C]$-glycine diluted with TB1A was added to each well to give a final concentration of 10 micromolar. After incubation at room temperature for 3 hours, the Cytostar scintillating microplates were sealed and counted on a Top Count scintillation counter (Packard). Non-specific uptake of $[^{14}C]$-glycine was determined in the presence of 10 mM unlabeled glycine. $[^{14}C]$ taurine uptake experiments were performed according to the same protocol except that 10 mM unlabeled taurine was used to determine non-specific uptake. To determine potencies, a range of concentrations of the compounds of the present invention was added to the cells, followed by the fixed concentration of $[^{14}C]$glycine. The concentration of the present compound that inhibited half of the specific uptake of $[^{14}C]$ glycine ($IC_{50}$ value) was determined from the assay data by non-linear curve fitting.

In particular, the compounds of the following examples had activity in inhibiting specific uptake of $[^{14}C]$glycine in the aforementioned assay, generally with an $IC_{50}$ value of less than about 10 micromolar. Preferred compounds within the present invention had activity in inhibiting specific uptake of $[^{14}C]$glycine in the aforementioned assay with an $IC_{50}$ value of less than about 1 micromolar. These compounds were selective for $[^{14}C]$glycine uptake (by GlyT1 in the JAR cells) compared to $[^{14}C]$taurine uptake (by the taurine transporter TauT in the JAR cells). Such a result is indicative of the intrinsic activity of the compounds in use as inhibitors of GlyT1 transporter activity.

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

The compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In another specific embodiment, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In another specific embodiment, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-IV-TR. The skilled artisan will recognize that there are alternative nomenclatures, nosologies and classification systems for general medical conditions, and that these systems evolve with medical and scientific progress. Thus the term "obesity or eating disorders associated with excessive food intake" is intended to include like conditions and disorders that are described in other diagnostic sources.

The subject compounds are further useful in a method for the prevention, treatment, control, amelioration, or reducation of risk of the diseases, disorders and conditions noted herein.

The subject compounds are further useful in a method for the prevention, treatment, control, amelioration, or reduction of risk of the aforementioned diseases, disorders and conditions in combination with other agents, including an inhibitor of glycine transporter GlyT1 activity.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drugs) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromaazine, clozapine, cyprazepam, desipramine, dexclamol, diazepam, dichloralphenazone, divalproex, diphenhydramine, doxepin, estazolarn, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially S-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art.

In the treatment of conditions which require inhibition of glycine transporter GlyT1 activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the description of the chemistry and in the Examples that follow are:
$CH_2Cl_2$ dichloromethane
DIEA diisopropylethylamine
PS-DIEA polystyrene diisopropylethylamine
PS-DMAP polystyrene 4-N,N-dimethylaminopyridine
DCC polystyrene dicyclohexylcarbodiimide
Ra—Ni Raney Nickel
HOBt hydroxybenzotriazole
THF tetrahydrofuran
TFA trifluoroacteic acid
MeOH methanol
LAH lithium aluminium hydride
KHMDS potassium bis(trimethylsilyl)amide
MsCl methane sulphonyl chloride.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing methods well known to those skilled in the art for preparing analogous compounds, for example using the reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

The compounds of the formula (I) may be prepared by the acylation of the corresponding compound of the formula (II):

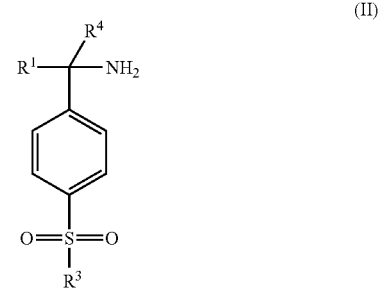

(II)

This acylation is conveniently carried out by the reaction of a compound of the formula (II) with a reactive derivative of a compound $R^2COOH$, for example an acid halide of the formula R²COhal, and preferably the appropriate acid chloride, in the presence of a weak base such as a trialkylamine, for example triethylamine, in a non polar solvent, for example a halogenated hydrocarbon such as dichloromethane, at a non-extreme temperature, for example -20 to 100° C. and conveniently 0 to 50° C. The compounds of the formula (II) may be prepared by reaction Scheme I:

tion with diisobutylaluminum hydride and the resultant compound reacted with a Grignard agent, for example cyclopropylmagnesium bromide or allylmagnesium chloride, for attaching the group $R^1$ (when the Grignard reagent contains an alkenyl group, this may be reduced to the corresponding alkyl group or a cyclopropyl group formed from the carbon-

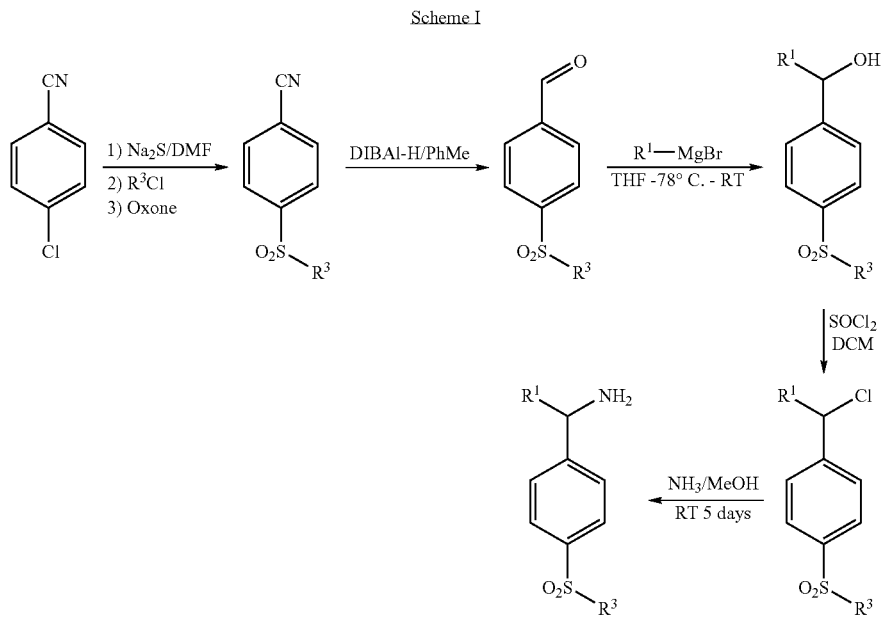

As illustrated in reaction Scheme (I), 4-chlorobenzonitrile is reacted with sodium sulphide and $R^3$hal in a polar aprotic solvent or, alternatively when $R^3$ is an acidic heterocycle, 4 fluorobenzonitrile may be reacted with an alkaline metal salt of the mercaptoheterocycle, for example 4-mercapto-[1,2,3] triazole sodium salt, to give the corresponding sulphanyl compound. This is then oxidized, by reaction with "Oxone". The nitrite group is converted to an aldehyde group by reaction carbon double bond by reaction with diiodomethane in the presence of zinc-copper couple). The hydroxyl group in the Grignard adduct is then halogenated, for example by reaction with thionyl chloride, and aminated, by reaction with ammonia, to give the compound of the formula (II).

When $R^1$ is a heterocycle, the compounds of the formula (II) may be prepared by reaction Scheme II:

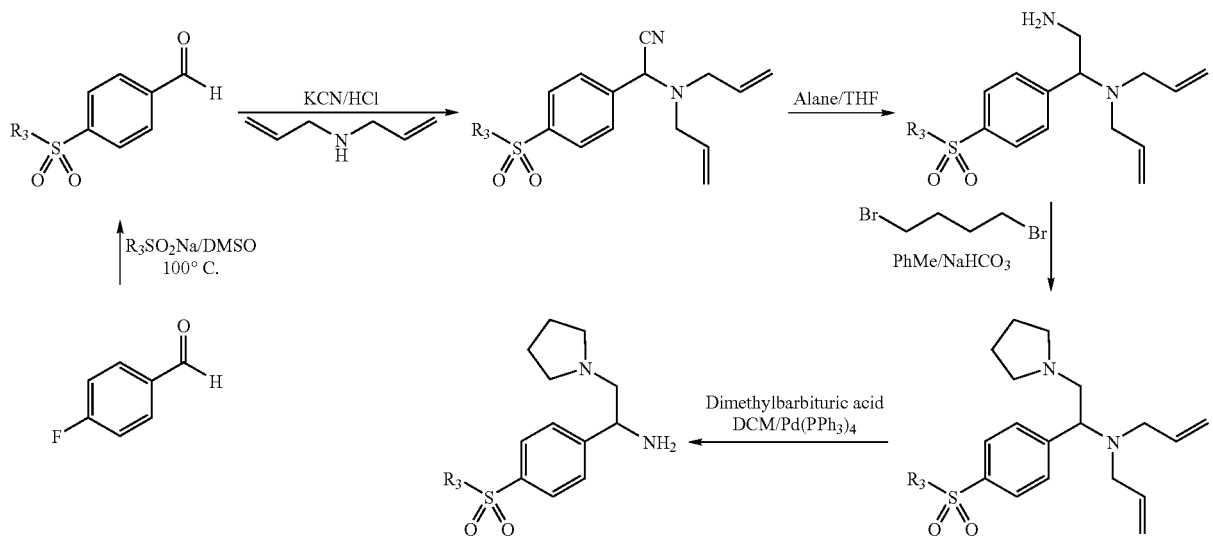

When R³ is an acidic heterocycle, the compounds of the formula (I) may be prepared by the method of Scheme III:

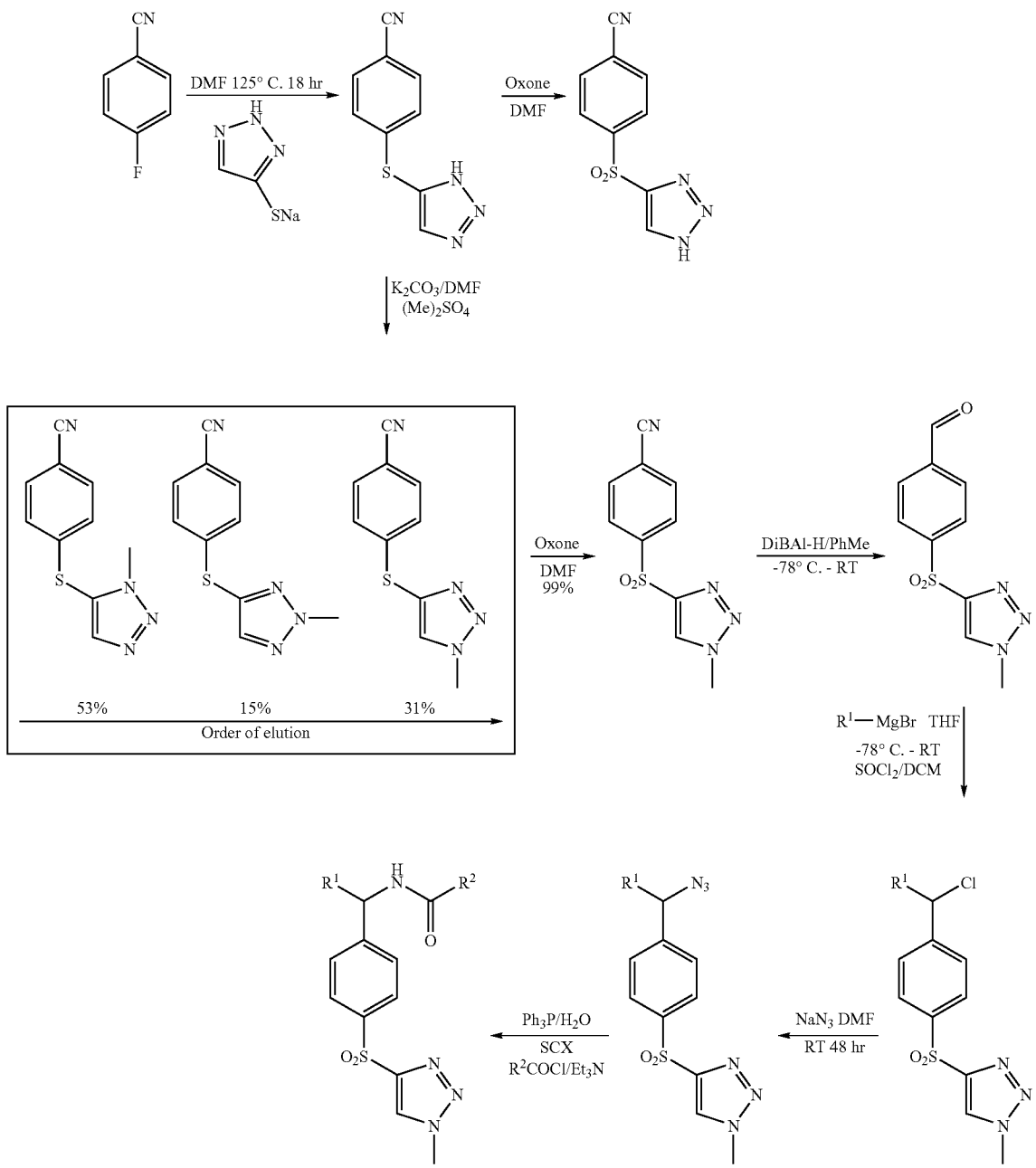

In this case, 4-fluorobenzonitrile is processed through to the Grignard adduct followed by displacement of the hydroxyl group by halo, for example chloro as described above. The halide, suitably chloride, is displaced by azide, for example by reaction with sodium azide in a dipolar aprotic solvent and the azide group then reduced and the resulting amine acylated, and preferably by reaction with the appropriate acid chloride, for example by reaction with R²COhal, in the presence of a weak base such as a trialkylamine, for example triethylamine, in a non polar solvent, for example a halogenated hydrocarbon such as dichloromethane.

The compounds of the formula (I) may also be prepared by oxidation of the corresponding sulphanyl compound. This oxidation may conveniently be carried out by reaction with "Oxone" in a suitable solvent, for example a ketone such as acetone at a non-extreme temperature, for example −20 to 150° C. and conveniently 20 to 100° C. When nitrogen containing heterocycles are present, it may be necessary to protect the ring nitrogen atom, for example with BOC, and then remove the protecting group after oxidation.

A representative method for making the sulphanyl compounds is depicted in Scheme IV (in this case illustrated by where Ar is phenyl):

Scheme IV

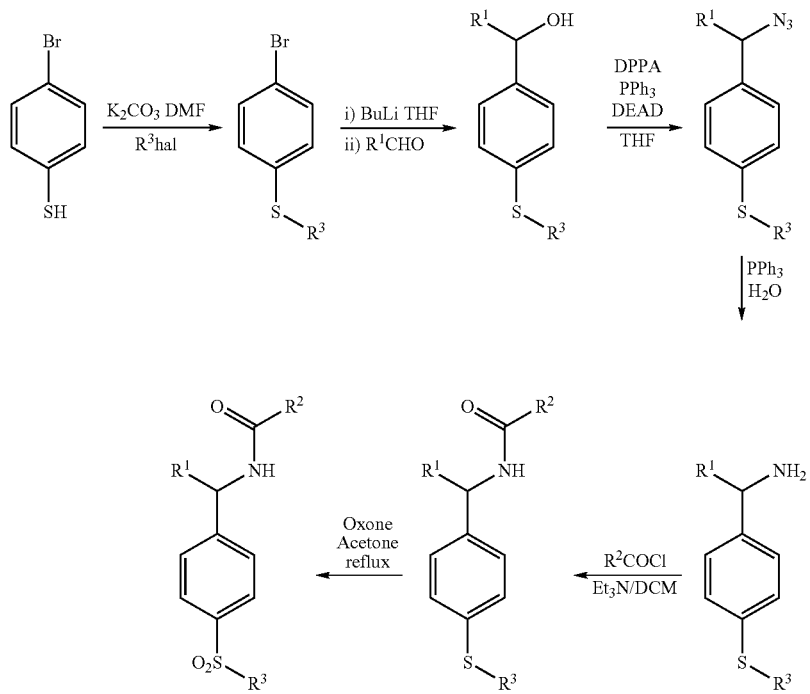

DPPA = Diphenyl phosphoryl azide
DEAD = Diethyl azodicarboxylate

4-Bromothiophenol is reacted with $R^3$hal in the presence of a base such as potassium carbonate in a dipolar aprotic solvent such as DMF. The bromo group is then replaced (i) by the group $R^1CH_2OH$ by reaction with butyllithium followed by addition of the aldehyde $R^1CHO$. The hydroxyl group is displaced by azide and the azide group in turn reduced to the amine and acylated, for example by reaction with the appropriate acid chloride $R^2COhal$, in the presence of a weak base such as a trialkylamine, for example triethylamine, in a non polar solvent, for example a halogenated hydrocarbon such as dichloromethane. The resulting compound is then oxidized as described above.

An alternative method is shown in Scheme V:

Scheme V

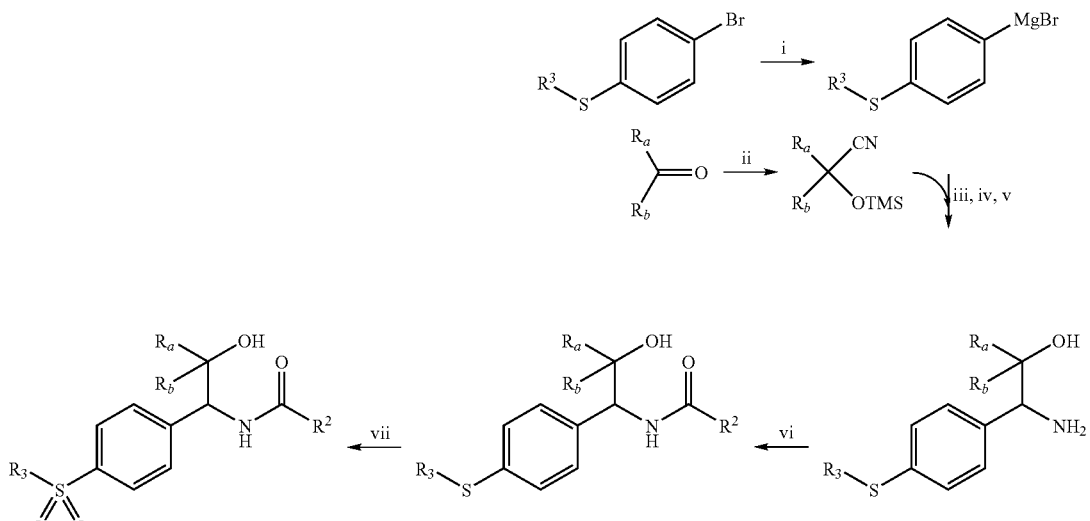

Reagents:; i. Mg, Et$_2$O; ii. TMSCN, CsF, MeCN; iii. Et$_2$O; iv. NaBH$_4$, MeOH; v. 1N HCl; vi. R$_2$COCl, DCM, aq. NaHCO$_3$; vii. Oxone, CHCl$_3$, alumina (grade V), R$^a$, R$^b$ = alkyl When R$^1$ is a saturated hererocycle the appropriate sulphanyl compound may be prepared in the following manner (Scheme VI):

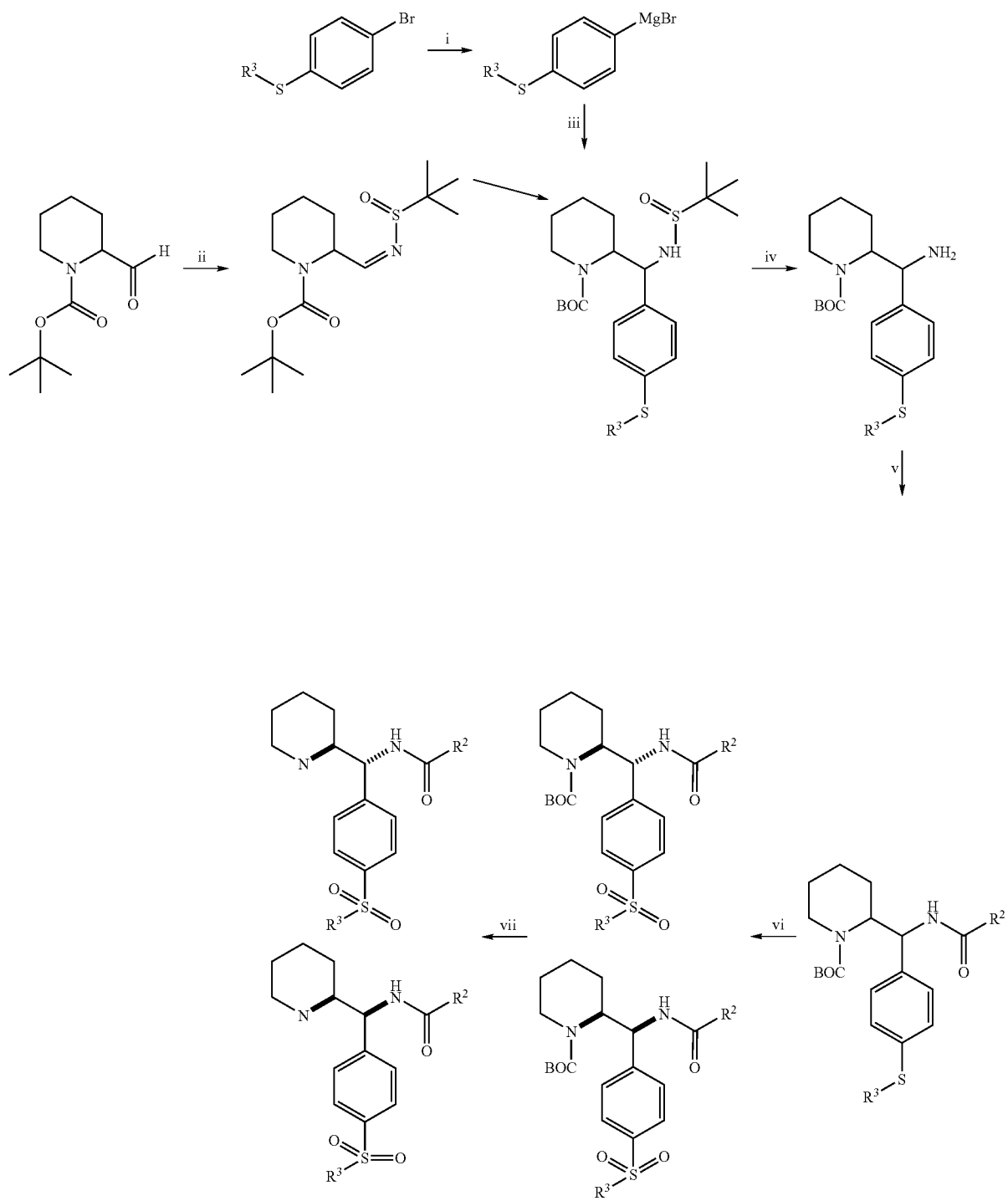
Reagents:; i. Mg, THF; ii. t-BuSONH$_2$, Ti(OEt)$_4$, THF; iii. THF; iv. MeOH, HCl; v. R$_2$COCl, Et$_3$N, DMAP, DCM; vi. Oxone, MeOH, H$_2$O; vii. TFA, DCM
When R$^1$ is an unsaturated heterocycle the appropriate sulphanyl compound may be prepared in the following manner (Scheme VII):

Scheme VII
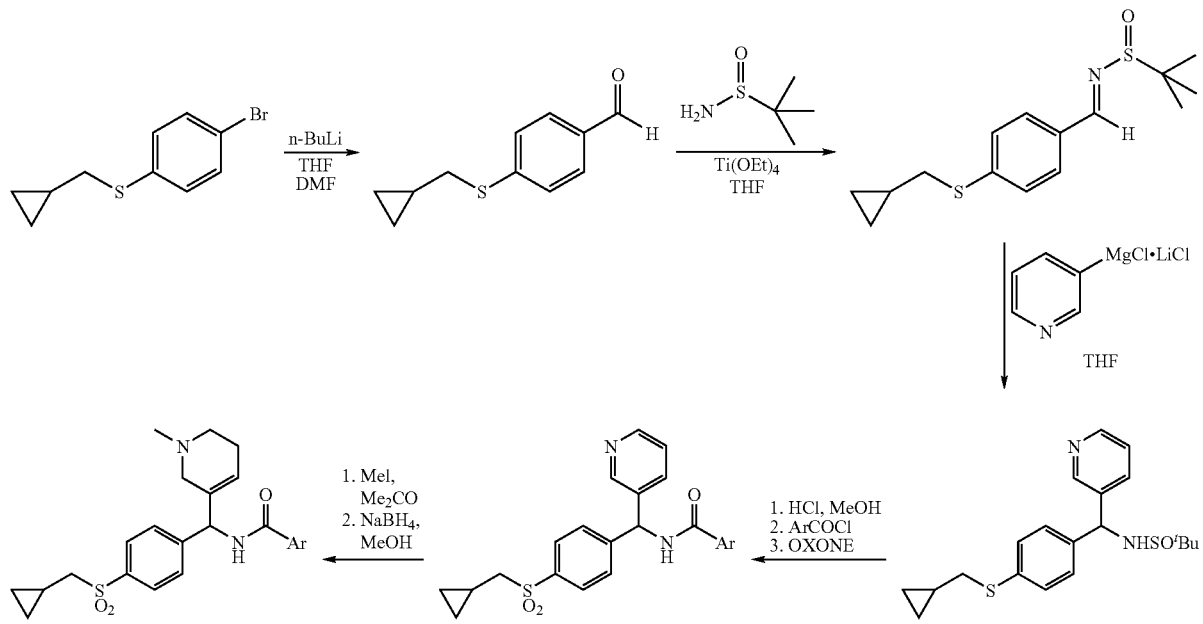
When Ar is a triazole ring, the sulphanyl compounds may be prepared as illustrated in Schemes VIII and IX:
Scheme VIII
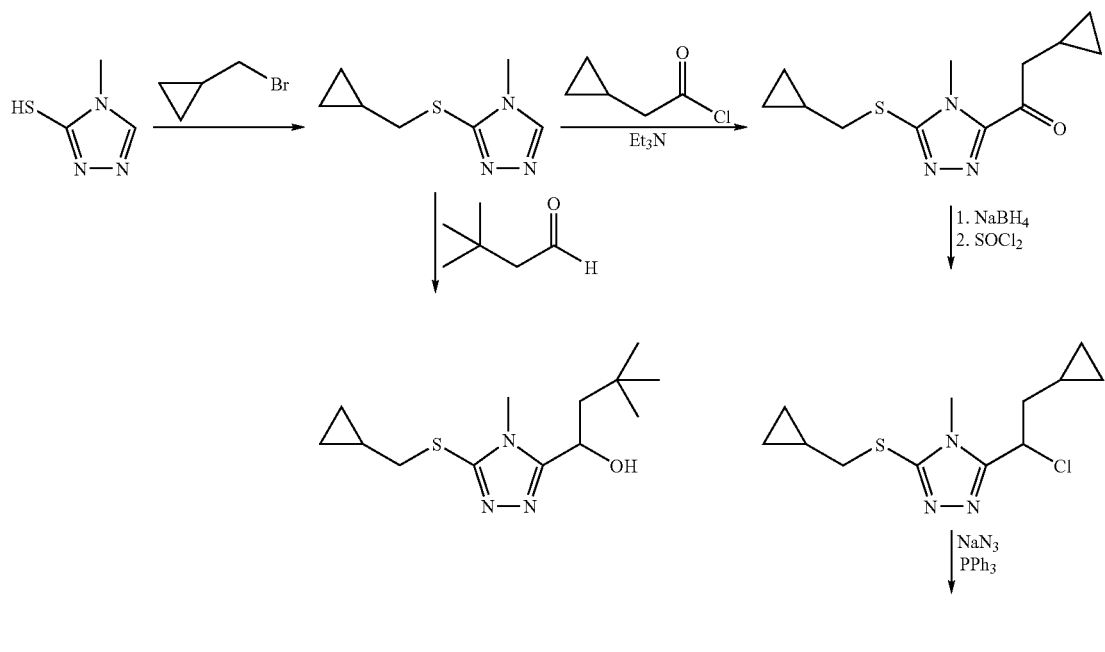

Scheme IX
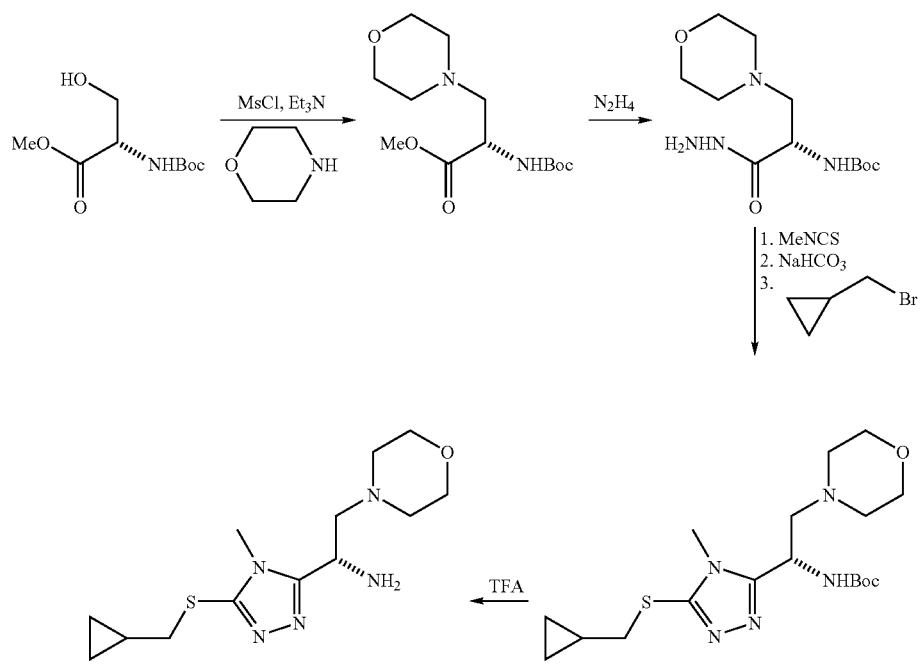
Alternative methods for introducing substituents R[1] may be adopted, for example as shown in Scheme X:
Scheme X
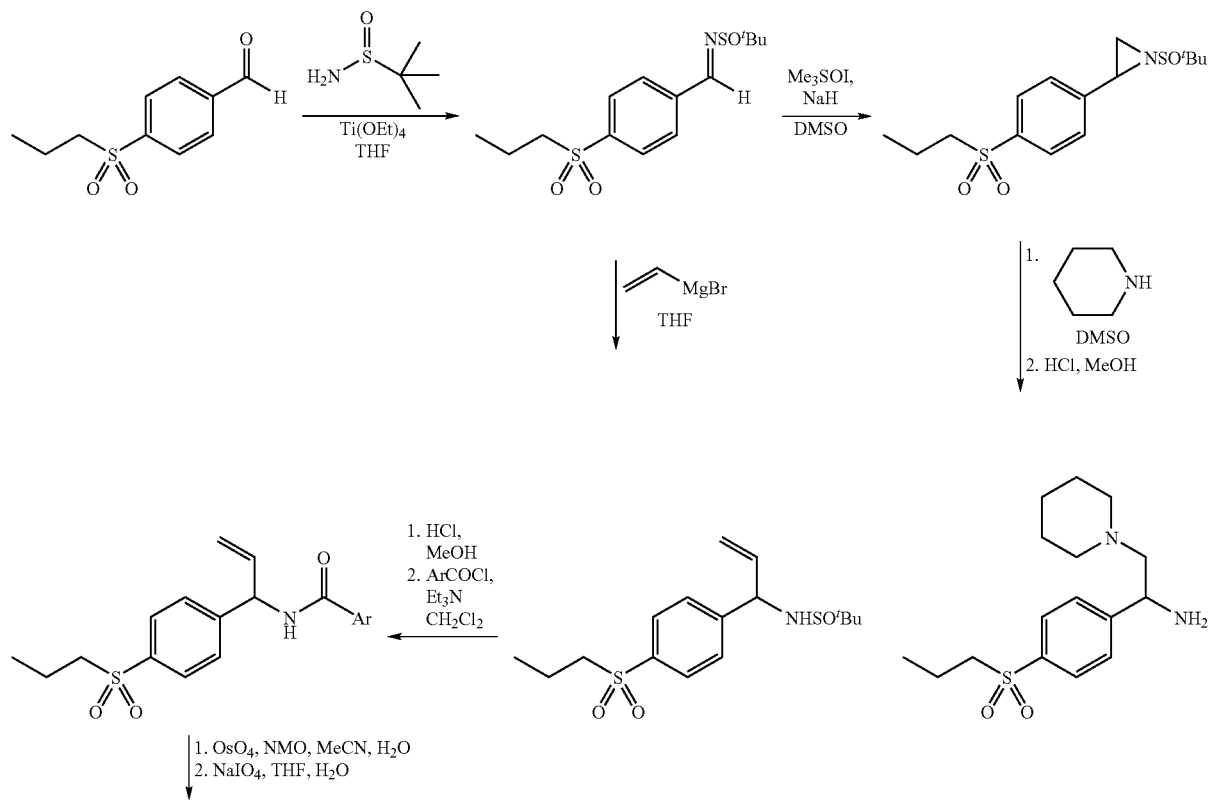

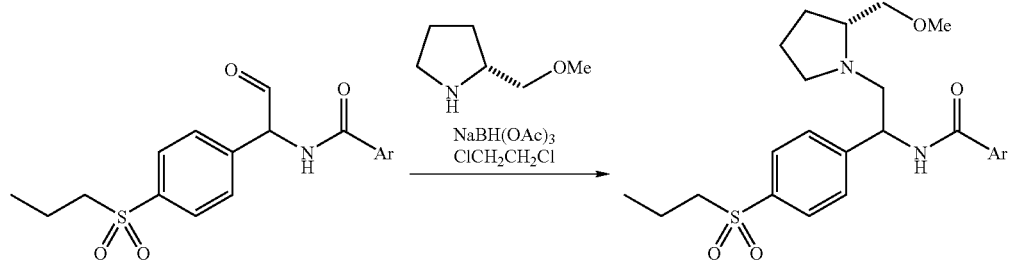

Compounds of the formula (I) may be converted into other compounds of the formula (I) for example when $R^1$ is pyridine, partial reduction of the pyridine ring and methylation of the ring nitrogen atom as shown in Scheme VII.

The following examples serve to illustrate the preparation of compounds of the present invention:

Example 1

2,4-Dichloro-N-{cyclopropyl[4-(propylsulphonyl)phenyl]methyl}benzamide

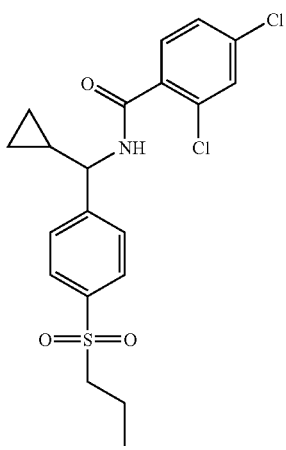

a) 4-(Propylsulphonyl)benzonitrile

To 4-chlorobenzonitrile (5 g) in dry N,N-dimethylformamide (50 mL), under nitrogen, was added sodium sulphide (3.11 g), and the stirred mixture heated in an oil bath at 130° C. for 48 h. The mixture was cooled to room temperature, 1-chloropropane (4.0 mL) added and stirring continued for 12 h. The mixture was cooled in an ice-water bath and "OXONE" (34 g) added with stirring. The water bath was removed after 2 h, and the mixture stirred at room temperature for 14 h. The reaction mixture was then diluted with an equal volume of ethyl acetate, solids removed by filtration, and solvent stripped at reduced pressure. The residue was chromatographed on silica gel, eluent 15 to 30% ethyl acetate in isohexane, and the title compound crystallised from isohexane as a white solid. $^1$H NMR (360 MHz, CDCl$_3$) δ 8.05 (2H, d, J=8.1 Hz), 7.88 (2H, d, J=8.3 Hz), 3.10 (2H, m), 1.76 (2H, m), 1.02 (3H, t, J=7.4 Hz).

b) 4-(Propylsulphonyl)benzaldehyde

To 4-(propylsulphonyl)benzonitrile (1.60 g) suspended in dry toluene (10 mL) cooled to −78° C. under nitrogen, was added a 1M solution of diisobutylaluminum hydride in toluene (8.5 mL). The mixture was stirred for 2 h, then the cooling bath removed and the reaction warmed to room temperature. The reaction was maintained at room temperature for 0.5 h before being cooled in an ice-water bath and quenched by addition of 2M aqueous hydrochloric acid (10 mL). The mixture was then stirred at room temperature for 0.5 h. The organic phase was separated, and the aqueous phase extracted with toluene. The combined organic phases were washed sequentially with water and brine, then solvent stripped at reduced pressure to afford 4-propylsulphonyl)benzaldehyde. $^1$H NMR (360 MHz, CDCl$_3$) δ 10.14 (1H, s), 8.09 (4H, m), 3.11 (2H, m), 1.76 (2H, m), 1.02 (3H, t, J=7.4 Hz).

c) Cyclopropyl-[4-(propylsulphonyl)phenyl]methanol

To 4-(propylsulphonyl)benzaldehyde (0.58 g) in dry tetrahydrofuran (5 mL), at −78° C. under nitrogen, was added a 0.5 M solution of cyclopropylmagnesium bromide in tetrahydrofuran (6.0 mL), slowly with stirring. The mixture was stirred for 1.75 h, quenched by addition of acetic acid (0.5 mL), then warmed to room temperature and partitioned between ethyl acetate and water. The organic phase was washed with brine, solvent stripped, and the residue chromatographed on silica gel, eluent 35% to 50% ethyl acetate in isohexane, to give the title compound as a white solid. $^1$H NMR (360 MHz, CDCl$_3$) δ 7.88 (2H, d, J=8.3 Hz), 7.63 (2H, d, J=8.4 Hz), 4.10 (1H, m), 3.06 (2K, m), 2.14 (1H, d, J=2.9 Hz), 1.75 (2H, m), 1.18 (1H, m), 0.99 (3H, t, J=7.4 Hz), 0.66 (2H, m), 0.49 (2H, m).

d) 2,4-Dichloro-N-{cyclopropyl[4-(propylsulphonyl)phenyl]methyl}benzamide

To the product of Example 1c, (0.40 g), in dry dichloromethane (5 mL), was added thionyl chloride (3.0 mL), and N,N-dimethylformamide (0.01 mL). The mixture was stirred for 3 h, then solvent stripped at reduced pressure, and the residue azeotroped with toluene. To the residue was added methanol (50 mL), the mixture cooled in an ice-water bath, and ammonia gas passed through until saturated. The vessel was then sealed and allowed to stand at room temperature for 5 days. Solvent was stripped and the residue azeotroped with toluene, and dried under vacuum. The product was taken up in dry dichloromethane (10 mL), and triethylamine (0.5 mL) added, followed by 2,4-dichlorobenzoyl chloride (0.5 mL), and the mixture stirred at room temperature for 18 hours. Solvent was stripped and residue partitioned between ethyl acetate and aqueous sodium hydrogencarbonate. Organic phase separated, solvent stripped, and residue chromatographed on silica gel, eluent 30% ethyl acetate in isohexane, to give the title compound as a white solid after crystallisation from dichloromethane by addition of diethyl ether then isohexane. $^1$H NMR (500 MHz, CDCl$_3$) δ 7.88 (2H, d, J=8.3 Hz), 7.64 (3H, m), 7.46 (1H, d, J=2 Hz), 7.34 (1H, dd, J=8.3, 2 Hz), 6.82 (1H, d, J=7 Hz) 4.59 (1H, m), 3.06 (2H, m), 1.75 (2H, m), 1.22 (1H, m), 1.00 (3H, t, J=7.4 Hz), 0.72 (2H, m), 0.52 (2H, m). MS (ES$^+$) m/z 426, 428 and 430[M+H]$^+$.

Example 2

2,4-Dichloro-N-(cyclopropyl {4-[(1-methyl-1H-1,2,3-triazol-4-yl)sulphonyl]phenyl}-methyl)benzamide

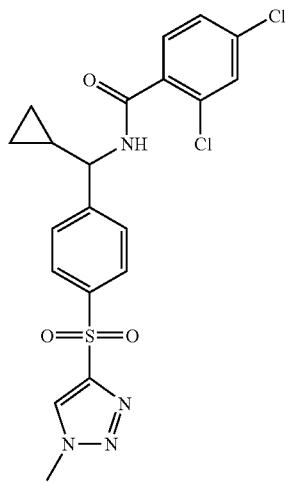

a) 4-(1H-1,2,3-Triazol-4-ylthio)benzonitrile

To 4-fluorobenzonitrile (6.1 g) in dry N,N-dimethylformamide (50 mL), under nitrogen, was added 4-mercapto-1,2,3-triazole sodium salt (6.2 g), and the stirred mixture heated in an oil bath at 125° C. for 18 h. The mixture was cooled to room temperature, and most of the solvent stripped at reduced pressure. The residue was partitioned between ethyl acetate and water, the organic phase washed with water, brine, then dried (sodium sulphate), and solvent stripped at reduced pressure. The residue was azeotroped with toluene, and the resulting solid triturated with isohexane, collected by filtration, washed with cold toluene, then isohexane, and dried in vacuo to give the title compound as a yellow solid (8.4 g). $^1$H NMR (360 MHz, CDCl$_3$) δ 12.45 (1H, br s), 7.92 (1H, s), 7.51 (2H, d, J=8.5 Hz), 7.22 (2H, d, J=8.5 Hz).

b) 4-(1H-1,2,3-Triazol-4-ylsulphonyl)benzonitrile

To the product of Example 2a (5.4 g) in N,N-dimethylformamide (30 mL), under nitrogen, was added "OXONE" (24 g) with stirring. The mixture stirred at room temperature for 24 h. The reaction mixture was then diluted with ethyl acetate (100 mL), washed with water, and the organic phase stripped at reduced pressure. The product was crystallised from toluene-isohexane as a white solid (5.1 g). $^1$H NMR (360 MHz, d$_6$-DMSO) δ 8.96 (1H, br s), 8.16 (5H, m).

c) 4-[(1-Methyl-1H-1,2,3-triazol-4-yl)sulphonyl]benzonitrile

To the product of Example 2b (1.55 g) in dry N,N-dimethylformamide (40 mL), under nitrogen, was added caesium carbonate (15 g), followed by dimethyl sulphate (1.0 mL) dropwise with stirring. The mixture was stirred at room temperature for 16 h. Most of the solvent was stripped at reduced pressure, and the residue was partitioned between ethyl acetate and water, the organic phase washed with water, then stripped at reduced pressure. The residue was chromatographed on silica gel, eluent 60% to 100% ethyl acetate in isohexane, to give the title compound as the more polar second eluting isomer (0.54 g). $^1$H NMR (500 MHz, CDCl$_3$) δ 8.20 (2H, d, J=8.6 Hz), 8.16 (1H, s), 7.85 (2H, d, J=8.5 Hz), 4.17 (3H, s).

d) 4-[(1-Methyl-1H-1,2,3-triazol-4-yl)sulphonyl]benzaldehyde

To the product of Example 2c, (0.290 g), suspended in dry toluene (5 mL) cooled at −78° C. under nitrogen, was added a 1M solution of diisobutylaluminum hydride in toluene (1.34 mL). The mixture was stirred for 2 h, then the cooling bath removed, and the reaction warmed to room temperature. Room temperature was maintained for 0.5 h, then the reaction was cooled in an ice-water bath and quenched by addition of 1M aqueous hydrochloric acid (10 mL) and ethyl acetate. The mixture was then stirred at room temperature for 0.5 h. The organic phase was separated, and the aqueous phase extracted with ethyl acetate. The combined organic phases were washed with water, brine, then solvent stripped at reduced pressure, to afford the title compound (0.268 g). $^1$H NMR (500 MHz, CDCl$_3$) δ 10.10 (1H, s), 8.26 (2H, d, J=8.4 Hz), 8.15 (1H, s), 8.04 (2H, d, J=8.5 Hz), 4.17 (3H, s).

e) Cyclopropyl-{4-[(1-methyl-1H-1,2,3-triazol-4-yl)sulphonyl]phenyl}methanol

To the product of Example 2d, (0.268 g), in dry tetrahydrofuran (5 mL), at −78° C. under nitrogen, was added a 0.5 M solution of cyclopropylmagnesium bromide in tetrahydrofuran (4.3 mL), slowly with stirring. The mixture was stirred for 2 h, then warmed to room temperature, and quenched by addition of saturated aqueous ammonium chloride, then partitioned between ethyl acetate and water. The organic phase was washed with brine, and solvent stripped to give the title compound (0.329 g). $^1$H NMR (360 MHz, CDCl$_3$) δ 8.09 (1H, s), 8.04 (2H, d; J=8.5 Hz), 7.60 (2H, d, J=8.4 Hz), 4.14 (3H, s), 4.06 (1H, d, J=8.5 Hz), 2.14 (1H, br s), 1.14 (1H, m), 0.63 (2H, m), 0.46 (2H, m).

f) 2,4-Dichloro-N-(cyclopropyl-{4-[(1-methyl-1H-1,2,3-triazol-4-yl)sulphonyl]-phenyl}methyl)benzamide To the product of Example 2e, (0.329 g), in dry dichloromethane (5 mL), was added thionyl chloride (3.0 mL). The mixture was stirred for 3 h, then solvent stripped at reduced pressure, and the residue azeotroped with toluene. To the residue was added dry N,N-dimethylformamide (2 mL) and sodium azide (0.3 g). The mixture was stirred at 50° C. for 2 days, then diluted with ethyl acetate, and washed with water. The organic phase was stripped to afford a brown oil dried under vacuum. The product was taken up in tetrahydrofuran (5 mL), water (0.5 mL) and triphenylphosphine (0.58 g) added, and the mixture stirred at room temperature for 18 h. The reaction mixture was applied to a strongly acidic cation exchange resin (20 g scx cartridge), eluted with methanol, then ammonia (2M in methanol) to recover the desired amine. The amine containing fractions were evaporated, the residue azeotroped with toluene, and the residue dissolved in dry dichloromethane (2 mL), and triethylamine (0.75 mL) added, followed by 2,4-dichlorobenzoyl chloride (0.2 mL), and the mixture stirred at room temperature for 18 h. Solvent was stripped and residue partitioned between ethyl acetate and aqueous sodium hydrogencarbonate. The organic phase was separated, solvent stripped, and the residue chromatographed on silica gel, eluent 60% ethyl acetate in isohexane, to give the title compound as a white solid after crystallisation from dichloromethane by addition of diethyl ether then isohexane. $^1$H NMR (400 MHz, CDCl$_3$) δ 8.07 (1H, s), 8.04 (2H, d, J=8.4 Hz), 7.60 (3H, m), 7.43 (1H, d, J=2 Hz), 7.31 (1H, dd, J=8.3, 2 Hz), 6.83 (1H, br d, J=7 Hz), 4.53 (1H, m), 4.13 (3H, s), 1.19 (1H, m), 0.69 (2H, m), 0.50 (2H, m). MS (ES$^+$) m/z 465, 467 and 469[M+H]$^+$.

Example 3

2,4-Dichloro-N-{2-cyclopropyl-1-[4-(propylsulphonyl)phenyl]ethyl}benzamide

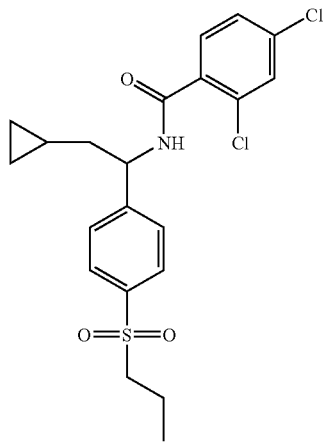

a) 1-[4-(Propylsulphonyl)phenyl]but-3-en-1-ol

To the product of Example 1b (3.03 g) in dry tetrahydrofuran (30 mL) at −78° C. under nitrogen was added a 2 M solution of allylmagnesium chloride in tetrahydrofuran (10 mL), slowly with stirring. The mixture was stirred for 2 hours, then warmed to 0° C., quenched by addition of saturated aqueous ammonium chloride, then partitioned between ethyl acetate and water. Organic phase was washed with brine, solvent stripped, and residue chromatographed on silica gel, eluent 30% ethyl acetate in isohexane, to give the title compound (3.29 g) as a colourless solid. MS (ES$^+$)/Z 255[M+H]$^+$.

b) 2-Cyclopropyl-1-[4-(propylsulphonyl)phenyl]ethanol

To activated zinc dust (3.0 g) and cuprous chloride (0.456 g) under a nitrogen atmosphere was added dry diethyl ether, and the mixture heated at reflux for 0.5 h. Diiodomethane (0.62 mL) was added and the mixture heated at reflux for 1 h. A solution of the product of Example 3a (1.02 g) and diiodomethane (0.5 mL) in dry diethyl ether (10 mL) was then added and reflux continued for 5 h. A further portion of diiodomethane (0.5 mL) was then added and the mixture heated at reflux for 18 h. The reaction mixture was diluted with diethyl ether, solids removed by filtration, solvent stripped, and residue chromatographed on silica gel, eluent 30% ethyl acetate in isohexane, to give the title compound (0.72 g). $^1$H NMR (500 MHz, CDCl$_3$) δ 7.85 (2H, d, J=7.6 Hz), 7.56 (2H, d, J=8.1 Hz), 4.89 (1H, m), 3.05 (2H, m), 2.32 (1H, br s), 1.73 (2H, m), 1.66 (2H, m), 0.99 (3H, t, J=7.4 Hz), 0.71 (1H, m), 0.48 (2H, m), 0.12 (1H, m), 0.04 (1H, m).

c) 2,4-Dichloro-N-{2-cyclopropyl-1-[4-(propylsulphonyl)phenyl]ethyl}benzamide

According to the method of Example 2f, the product of Example 3b was converted to the title compound. $^1$H NMR (500 MHz, CDCl$_3$) δ 7.88 (2H, d, J=8.3 Hz), 7.69 (1H, d, J=8.4 Hz), 7.57 (2H, d, J=8.3 Hz), 7.45 (1H, d, J=2 Hz), 7.33 (1H, dd, J=8.3, 2 Hz), 6.90 (1H, d, J=7 Hz), 5.29 (1H, m), 3.05 (2H, m), 1.85 (1H, m), 1.74 (3H, m), 1.00 (3H, t, J=7.4 Hz), 0.65 (1H, m), 0.51 (2H, m), 0.13 (2H, m). MS (ES$^+$) m/z 440, 442 and 444 [M+H]$^+$.

Example 4

2,4-Dichloro-N-{2,2-dimethyl-1-[4-(propylsulphonyl)phenyl]propyl}benzamide

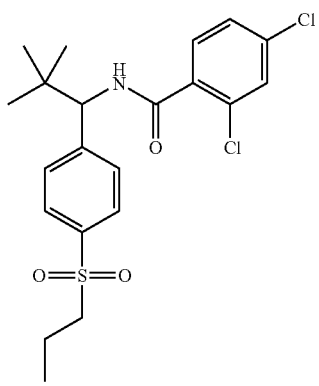

a) 1-Bromo-4-propylthio)benzene

To a stirred solution of 4-bromothiophenol (18.8 g, 100 mmol) in DMF (100 ml) was added potassium carbonate followed by 1-iodopropane (18.7 g, 100 mmol) and the reaction mixture stirred for 16 h. The reaction was quenched with water (10 ml) and the reaction mixture partitioned between ethyl acetate (200 ml) and water (100 ml). The organic phase was separated, washed with water (100 ml), brine (50 ml) then dried over MgSO$_4$. The mixture was filtered and the solvent evaporated to give a pale yellow oil which was used in the next step without further purification (21 g). $^1$H NMR δ (CDCl$_3$) 7.37 (2H, d, J=8.2 Hz), 7.16 (2H, d, J=8.2 Hz), 2.86 (2H, t, J=7.3 Hz), 1.65 (2H, m), 1.02 (3H, t, J=7.3 Hz).

b) 2,2-Dimethyl-1-[4-(propylthio)phenyl]propan-1-ol

To a stirred solution of 1-bromo-4-(propylthio)benzene (500 mg, 2.16 mmol) in THF (10 ml) at −78° C. was added n-butyllithium (2.5 M in hexanes, 0.91 ml, 2.27 mmol). The resulting yellow solution was stirred at −78° C. for 15 minutes then pivaldehyde (0.29 ml, 2.59 mmol) was added. The mixture was allowed to warm to room temperature, during which time the solution turned colourless. The mixture was partitioned between ethyl acetate (60 ml) and water (30 ml). The organic phase was separated, washed with brine (30 ml), dried over MgSO₄ filtered and evaporated to give a colourless oil. The crude product was chromatographed on silica eluting with 5% ethyl acetate in hexanes to give the title product as a pale yellow oil (468 mg). ¹H NMR δ (CDCl₃) 7.28-7.20 (4H, m), 4.36 (1H, s), 2.89 (2H, t, J=7.3 Hz), 1.84 (1H, s), 1.71-1.63 (2H, m), 1.02 (3H, t, J=7.3 Hz), 0.91 (9H, s).

c) 1-(1-Azido-2,2-dimethylpropyl)-4-(propylthio) benzene

To a stirred solution of 2,2-dimethyl-1-[4-(propylthio)phenyl)propan-1-ol (466 mg, 1.95 mmol) in THF (10 ml) were added triphenylphosphine (666 mg, 2.54 mmol), diethyl azodicarboxylate (0.40 ml, 2.54 mmol), and finally diphenylphosphoryl azide (0.55 ml, 2.54 mmol). The mixture was stirred at room temperature over for 3 days. Water (1 ml) was added and the mixture was evaporated. The residue was partitioned between ethyl acetate (50 ml) and water (30 ml). The organic phase was separated, washed with brine (30 ml), dried over MgSO₄, filtered and evaporated to give an oil. The crude product was chromatographed on silica eluting with 4% EtOAc in hexanes to give the title product as a pale yellow oil (284 mg). ¹H NMR δ (CDCl₃) 7.29-7.27 (2H, m), 7.17-7.15 (2H, m), 4.23 (1H, s), 2.92 (2H, t, J=7.3 Hz), 1.73-1.67 (2H, m), 1.04 (3H, t, J=7.4 Hz), 0.90 (9H, s).

d) 2,2-Dimethyl-1-[4-(propylthio)phenyl]propan-1-amine

To a stirred solution of 1-(1-azido-2,2-dimethylpropyl)-4-(propylthio)benzene (282 mg, 1.07 mmol) in THF (8 ml) were added triphenylphosphine (842 mg, 3.21 mmol) and water (2 ml). The mixture was heated at 50° C. for 18 hours then allowed to cool to room temperature. Methanol (10 ml) was added and the mixture was passed through an SCX cartridge, which had been pre-treated with HCl in MeOH, eluting first with several column lengths of methanol to remove the triphenylphosphine oxide, then with 2M solution of ammonia in methanol to elute the product. The appropriate fractions were evaporated to give the title product as a pale yellow oil (231 mg). ¹H NMR 3 (CDCl₃) 7.27-7.19 (4H, m), 3.67 (1H, s), 2.89 (2H, t, J=7.3 Hz), 1.72-1.62 (2H, m), 1.02 (3H, t, J=7.3 Hz), 0.89 (9H, s).

e) 2,4-Dichloro-N-{[2,2-dimethyl-1-[4-(propylthio) phenyl]propyl}benzamide

To a stirred solution of 2,2-dimethyl-1-[4-(propylthio)phenyl]propan-1-amine (231 mg, 0.973 mmol) and diisopropyl-ethylamine (0.20 ml, 1.17 mmol) in DCM (3 ml) was added 2,4-dichlorobenzoyl chloride (0.16 ml, 1.17 mmol). The mixture was stirred at room temperature for 2 hours. DCM (5 ml) and water (5 ml) were added and the mixture was stirred vigorously for 5 minutes then passed through a PTFE separation frit. The organic phase was collected and evaporated to give an orange oil. The crude product was chromatographed on silica eluting with 17% ethyl acetate in hexanes to give the title product as a white foam (322 mg). ¹H NMR δ (CDCl₃) 7.72-7.70 (1H, m), 7.45-7.44 (1H, m), 7.33-7.25 (3H, m), 7.16 (2H, d, J=8.1 Hz), 6.96 (1H, d, J=8.1 Hz), 4.95 (1H, d, J=9.0 Hz), 2.89 (2H, t, J=7.3 Hz), 1.71-1.63 (2H, m), 1.05-0.98 (12H, m); m/z=410:412 (3:2)

f) 2,4-Dichloro-N-{2,2-dimethyl-1-[4-(propylsulphonyl)phenyl]propyl}benzamide

To a stirred solution of 2,4-dichloro-N-{[2,2-dimethyl-1-[4-(propylthio)phenyl]-propyl}benzamide (322 mg, 0.788 mmol) in acetone (5 ml) was added "OXONE" (1.45 g, 2.35 mmol) in water (2.5 ml). The mixture was heated at reflux for 2 hours then allowed to cool to room temperature. Water (10 ml) was added and the pH was adjusted to 7 with 2M sodium hydrogen carbonate solution. The mixture was extracted with DCM (3 ml) and the organic phase was dried over MgSO₄ and evaporated to give a yellow oil. The crude product was chromatographed on silica eluting with 30% ethyl acetate in hexanes to give a colourless oil, which crystallised from diethyl ether as a white solid (205 mg). ¹H NMR δ (CDCl₃) 7.86 (2H, d, J=8.3 Hz), 7.72 (1H, d, J=8.4 Hz), 7.48-7.46 (3H, m), 7.33 (1H, dd, J=2.0, 8.4 Hz), 7.11 (1H, d, J=8.2 Hz), 5.01 (1H, d, J=8.2 Hz), 3.08-3.04 (2H, m), 1.81-1.73 (2H, m), 1.02-0.98 (12H, m); m/z=442:444 (3:2)

Examples 5 and 6

(2R*)-2-{(R*)-{[2-Chloro-3-(trifluoromethyl)benzoyl]amino}[4-(ethylsulfonyl)phenyl] methyl}piperidinium trifluoroacetate and (2R*)-2-{(S*)-{[2-chloro-3-(trifluoromethyl)benzoyl] amino}[4-(ethylsulfonyl)phenyl] methyl}piperidinium trifluoroacetate

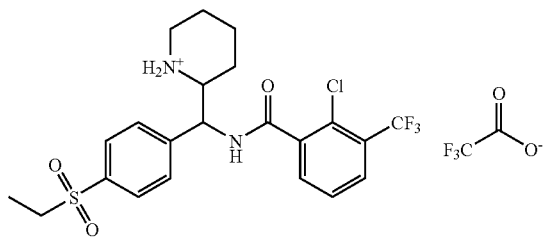

a) tert-Butyl 2-{(Z)-[(tert-butylsulphinyl)imino] methyl}piperidine-1-carboxylate tert-Butylsulphinamide (1.21 g, 10 mmol) was added to a stirred mixture of tert-butyl 2-formylpiperidine-1-carboxylate (1.64 g, 7.7 mmol) and titanium ethoxide (3.2 mL, 15.4 mmol) in THF (20 mL). The reaction mixture was stirred for 12 h at ambient temperature, poured into a bi-phasic mixture of brine (100 mL) and ethyl acetate (100 mL) and stirred for a further 30 min. The mixture was filtered through a pad of Celite and the phases were separated. The organic phase was dried (MgSO₄) and concentrated to give the title product which was used without purification (2.77 g). ¹H NMR (400 MHz, CDCl₃): δ 7.93 (1H, dd, J=6.8, 2.1 Hz), 5.03 (1H, br), 4.00 (1H, br s), 2.76-3.03 (1H, br), 2.1 (1H, d, J=13 Hz), 1.87-1.55 (3H, m), 1.50-1.40 (9H, br), 1.36-1.13 (11H, m), b) 4-(Ethylthio)phenylmagnesium bromide 1-Bromo-4-(ethylthio)benzene (0.5 g, 2.3 mmol) was added to a stirred mixture of magnesium turnings (1.96 g, 82 mmol) in THF (10 mL). 1,2-Dibromoethane (30 μL) was then added and the mixture was heated at reflux to initiate the reaction. A solution of 1-bromo-4-(ethylthio)benzene (18.2 g, 84 mmol) in THF (60 mL) was added at such a rate to maintain the reaction mixture at gentle reflux. The reaction mixture was then stirred at 50° C. for 90 min and cooled to ambient temp to give a 1.16M solution of 4-(ethylthio)phenylmagnesium bromide in THF which was used in the next reaction.

c) tert-Butyl 2-{amino[4-(ethylthio)phenyl]methyl}piperidine-1-carboxylate

A solution of 4-ethylthio)phenylmagnesium bromide in THF (10 mL, 11.6 mmol) was added to cooled 0° C.) solution of tert-butyl 2-{(Z)-[(tert-butylsulfinyl)imino]methyl}piperidine-1-carboxylate (1.5 g, 4.7 mmol) in THF (10 mL) and the mixture was stirred for 60 min The reaction was quenched by addition of 60 mL of a 1:1 mixture of saturated aqueous ammonium chloride and 33% aqueous ammonia before extraction with ethyl acetate (100 mL). The organic phase was dried (MgSO$_4$) and concentrated. The residue was dissolved in methanol (20 mL), cooled to 0° C., treated with 4N hydrochloric acid in dioxane 50 mL) and stirred for 30 min. The reaction was neutralised by adding 4N aqueous sodium hydroxide (6 mL) and the mixture was extracted into DCM. The organic extract was dried (Na$_2$SO$_4$) and concentrated. The residue was purified on silica gel eluting with iso-hexane on a gradient of ethyl acetate (0-60%) then with dichloromethane on a gradient of methanol (2-10%) to give the title product as a 2:1 mixture of diastereoisomers (760 mg, 45%). $^1$H NMR (360 MHz, CDCl$_3$, 2:1 mixture): δ 7.30-7.20 (4H, m), 4.12-4.27 (2H, br), 3.88-4.00 (1H, br), 3.63-3.75 (1H, br), 2.90 (2H, q, J=7.4 Hz), 2.80 (1H, dt, J=2.6, 13.4 Hz), 2.11 (1H, d, J=13.2 Hz), 1.37-1.75 (7H, m), 1.29 (3H, t, J=7.4 Hz), 1.22 (3H, s), 1.18 (6H, s).

d) 2-{{[2-Chloro-3-(trifluoromethyl)benzoyl]amino}[4-(ethylsulphonyl)phenyl]methyl}piperidinium trifluoroacetate To a mixture of tert-butyl 2-{amino[4-(ethylthio)phenyl]methyl}piperidine-1-carboxylate (94 mg, 0.27 mmol), triethylamine (0.102 mL, 0.72 mmol) and 4-(N,N-dimethylamino)pyridine (5 mg, 0.04 mmol) in dichloromethane (1 mL) was added 2-chloro-3-(trifluoromethyl)benzoyl chloride (130 mg, 0.54 mmol) and the mixture was stirred at ambient temperature for 15 min. Methanol (0.5 mL) was then added and the reaction concentrated in vacuo. The residue was treated with methanol (5 mL) and a solution of OXONE® (0.8 mg, 1.3 mmol) in water (4 mL) was added drop-wise. The mixture was stirred for 1 hour, treated with 0.5M aqueous solution of Na$_2$SO$_3$ and extracted into ethyl acetate. The organic phase was dried (Na$_2$SO$_4$) and concentrated. The residue was purified by preparative TLC (eluting with iso-hexane/ethyl acetate 1:1) to give two diastereoisomers. Both sample were treated independently with 20% trifluoroacetic acid in dichloromethane and after 2 hours at ambient temperature were concentrated to give both possible diastereoisomers of the title product. (2R*)-2-{(R*)-{[2-chloro-3-trifluoromethyl)benzoyl]amino}[4-(ethylsulphonyl)phenyl]methyl}piperidinium trifluoroacetate. $^1$H NMR (500 MHz, CD$_3$OD): δ 8.00 (2H, d, J=8.2 Hz), 7.88 (1H, d, J=8.1 Hz), 7.79 (1H, d, J=7.6 Hz), 7.73 (2H, d, J=8.2 Hz), 7.58 (1H, t, J=7.9 Hz), 5.36 (1H, d, J=9.8 Hz), 3.65 (1H, m), 3.51 (1H, m), 3.25 (2H, q, J=7.3 Hz), 3.07 (1H, dt, J=3.2, 12.9 Hz), 1.90 (2H, m), 1.71 (1H, m), 1.59 (1H, m), 1.54-1.42 (2H, m), 1.23 (3H, t, J=7.5 Hz); MS m/e 489 (M$^+$+1). 2R*)-2-{(S)-{[2-chloro-3-(trifluoromethyl)benzoyl]amino}[4-(ethylsulphonyl)-phenyl]methyl}piperidinium trifluoroacetate. $^1$H NMR (500 MHz, CD$_3$OD): δ 8.03 (2H, br d, J=8.3 Hz), 7.90 (1H, d, J=7.8 Hz), 7.76 (2H, d, J=8.4 Hz), 7.73 (1H, d, J=7.7 Hz), 7.59 (1H, t, J=7.8 Hz), 5.52 (1H, d, J=7.4 Hz), 3.67 (1H, ddd, J=2.5, 7.0, 11.2 Hz), 3.42 (1H, m), 3.25 (2H, q, J=7.4 Hz), 3.03 (1H, dt, J=3.1, 13.0 Hz), 2.17 (1H, br d, J=14.0 Hz), 1.99 (1H, br d, J=13.4 Hz), 1.92 (1H, br d, J=14.0 Hz), 1.54-1.76 (3H, m), 1.25 (3H, t, J=7.4 Hz); MS m/e 489 (M$^+$+1).

Example 7

2-Chloro-N-(1-{4-[(cyclopropylmethyl)sulphonyl]phenyl}-2-hydroxy-2-methylpropyl)-3-(trifluoromethyl)benzamide

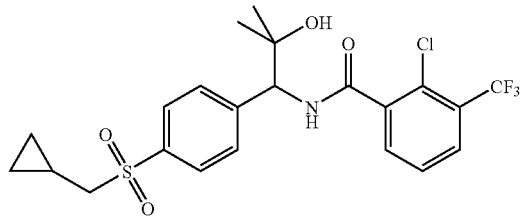

a) 1-Bromo-4-[(cyclopropylmethyl)thio]benzene

4-Bromothiophenol (37.8 g) in N,N-dimethylformamide (200 mL) was treated with potassium carbonate (30.4 g) and cyclopropylmethyl bromide (29.7 g). The suspension was stirred at ambient temperature for 16 hrs then diluted with diethyl ether (500 mL). The organic phase was washed with water (2×500 mL), dried (MgSO$_4$) and concentrated to give the title compound as an oil (46.4 g). $^1$H NMR (360 MHz, CDCl$_3$): δ 7.38 (2H, d, J=8.0 Hz), 7.21 (2H, d, J=8.0 Hz), 2.83 (2H, d, J=7.0 Hz), 1.08-0.98 (1H, m), 0.58 (2H, q, J=5.1 Hz), 0.24 (2H, q, J=5.1 Hz).

b) 2-Methyl-2-[(trimethylsilyl)oxy]propanenitrile

To anhydrous acetone (3.7 mL) in acetonitrile (50 mL) was added caesium fluoride (760 mg) followed by trimethylsilyl cyanide (10 mL). The exothermic reaction was then allowed to stir back to ambient temperature over 1.5 hr then concentrated in vacuo. The residue was partitioned between water (100 mL) and dichloromethane (100 mL). The organic phase was removed, dried MgSO$_4$) and concentrated to give the title compound as an oil (4.35 g). $^1$H NMR (360 MHz, CDCl$_3$): δ 1.60 (6H, s), 0.24 (9H, s).

c) 1-Amino-1-{4-[(cyclopropylmethyl)thio]phenyl}-2-methylpropan-2-ol

To magnesium turnings (888 mg) in diethyl ether (60 mL) was added 1-bromo-4-[(cyclopropylmethyl)thio]benzene (8.4 g). The mixture was heated at reflux for 16 hrs, and then cooled to ambient temperature. A solution of 2-methyl-2-[(trimethylsilyl)oxy]propanenitrile (4.35 g) in diethyl ether (30 mL) was then added and this solution was stirred at ambient temperature for 7 h. Sodium borohydride (1.33 g) in methanol (30 mL) was then slowly added and the solution aged for 2 h Water (25 mL) was added followed by 1N hydrochloric acid (100 mL) and the mixture stirred for 1 h. The organic layer was extracted with a further portion of 1N hydrochloric acid (100 mL) and the acid extracts combined. These were then made basic with 4N sodium hydroxide solution and extracted with dichloromethane (2×100 mL). The organic extracts were dried (MgSO$_4$) and concentrated to give the title compound as a yellow solid (3.7 g). $^1$H NMR (360 MHz, CDCl$_3$): δ 7.22-7.34 (4H, m), 3.77 (1H, s), 2.85 (2H, d, J=7.0 Hz), 1.21 (3H, s), 1.09-1.03 (1H, m), 1.03 (3H, s), 0.57 (2H, q, J=5.1 Hz), 0.24 (2H, q, J=5.1 Hz); m/z 307 (M-16 [NH$_2$])$^+$.

d) 2-Chloro-N-(1-{4-[(cyclopropylmethyl)thio]phenyl}-2-hydroxy-2-methylpropyl)-3-(trifluoromethyl)benzamide 1-Amino-1-(4-[(cyclopropylmethyl)thio]phenyl)-2-methylpropan-2-ol (150 mg) and 2-chloro-3-(trifluoromethyl)benzoyl chloride (300 mg) in dichloromethane (2 mL) were treated with saturated sodium bicarbonate solution (2 mL) and stirred vigorously for 16 h. The organic phase was dried (MgSO$_4$), concentrated and the residue purified by chromatography on silica (eluting with iso-hexane on a gradient of ethyl acetate) to give the title compound as a foam (189 mg). $^1$H NMR (500 MHz, CDCl$_3$): δ 7.76 (1H, d, J=7.8 Hz), 7.64 (1H, d, J=7.6 Hz), 7.41 (1H, t, J=7.8 Hz), 7.34 (2H, d, J=8.2 Hz), 7.28 (2H, d, J=8.2 Hz), 7.05 (1H, br d, J=8.5 Hz), 4.98 (1H, d, J=8.5 Hz), 2.87 (2H, d, J=7.0 Hz), 1.45 (3H, s), 1.10 (3H, s), 1.09-1.04 (1H, m), 0.59 (2H, q, J=5:1 Hz), 0.26 (2H, q, J=5.1 Hz); m/z 457, 459.

e) 2-Chloro-N-(1-{4-[(cyclopropylmethyl)sulphonyl]phenyl}-2-hydroxy-2-methylpropyl)-3-(trifluoromethyl)benzamide 2-Chloro-N-(1-{4-[(cyclopropylmethyl)thio]phenyl}-2-hydroxy-2-methylpropyl)-3-(trifluoromethyl)benzamide (172 mg) in methanol (5 mL) was treated with OXONE® (0.8 g) in water (2 mL) and stirred for 0.5 h. This mixture was quenched with aqueous 1N sodium sulphite solution (5 mL) and extracted with dichloromethane (2×10 mL). The combined extracts were dried (MgSO$_4$), concentrated and the residue purified by chromatography on silica (eluting with iso-hexane on a gradient of ethyl acetate) to give the product as a foam (152 mg). $^1$H NMR (400 MHz, CDCl$_3$) δ 7.92 (2H, d, J=8.4 Hz), 7.78 (1H, d, J=7.8 Hz), 7.63 (3H, t, J=7.4 Hz), 7.43 (1H, t, J=7.8 Hz), 7.22 (1H, d, J=8.4 Hz), 5.06 (1H, d, J=8.4 Hz), 3.08-2.96 (2H, m), 1.51 (3H, s), 1.09 (3H, s), 1.05-0.95 (1H, m), 0.61-0.53 (2H, m), 0.18-0.10 (2H, m); m/z 490, 492 (M+1)+, 472, 474 [(M-18)+1]+.

Examples 8 and 9

(2R*)-2-{(R*)-{[2-Chloro-3-(trifluoromethyl)benzoyl]amino}[3-(ethylsulphonyl)phenyl]methyl}piperidinium trifluoroacetate and (2R*)-2-{(S*)-{[2-chloro-3-(trifluoromethyl)benzoyl]amino}[3-(ethylsulphonyl)phenyl]methyl}-piperidinium trifluoroacetate

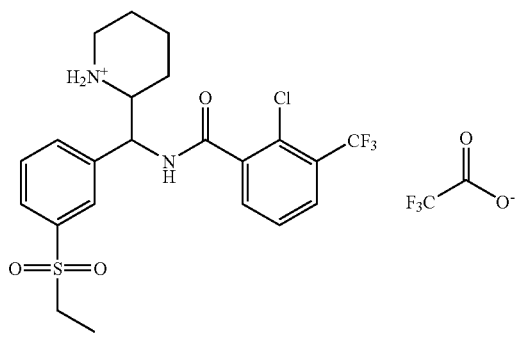

a) 1-Bromo-3-(ethylthio)benzene

The title compound was prepared using bromoethane and conditions described in Example 4a for the 4-propylthio analogue. $^1$H NMR (360 MHz, CDCl$_3$): δ 7.43 (1H, t, J=1.5 Hz), 7.28 (1H, br d, J=8.0 Hz), 7.22 (1H, d, J=8.2 Hz), 7.13 (1H, t, J=7.8 Hz), 2.94 (2H, q, J=7.3 Hz), 1.32 (3H, t, J=7.3 Hz).

b) 3-(Ethylthio)phenylmagnesium bromide

A 1.16 M solution of the title compound in THF was prepared using the conditions described in Examples 5 & 6 part b.

c) tert-Butyl 2-{amino[3-(ethylthio)phenyl]methyl}piperidine-1-carboxylate

A solution of 3-(ethylthio)phenylmagnesium bromide in THF (10 mL 11.6 mmol) was added to a cooled (0° C.) solution of tert-butyl 2-{(Z)-[(tert-butylsulfinyl)imino]methyl}piperidine-1-carboxylate (1.5 g, 4.7 mmol) in THF (10 mL) and the mixture was stirred for 60 min The mixture was quenched with 50 mL of a 1:1 mixture of saturated aqueous ammonium chloride and 33% aqueous ammonia before extracting into ethyl acetate (100 mL). The organic phase was dried (MgSO$_4$) and concentrated. The residue was treated with methanol (20 mL), cooled to 0° C. and then 4N hydrogen chloride in dioxane (5 mL) was added. After stirring for 30 min 4N aqueous sodium hydroxide (6 mL) was added and the mixture was extracted into DCM. The organic extract was dried (Na$_2$SO$_4$) and concentrated. The residue was purified on silica gel eluting with iso-hexane on a gradient of ethyl acetate (0-60%) followed by dichloromethane on a gradient of methanol (2-10%) to give the title product as a 1.7:1 mixture of diastereoisomers (860 mg, 51%). $^1$H NMR (360 MHz, CDCl$_3$): δ 7.30-7.09 (4H, m), 4.30-4.1 (2H, m), 4.05-3.88 (1H, br), 3.78-3.60 (2H, m), 2.99-2.88 (2H, m), 2.80 (1H, dt, J=2.8, 13.4 Hz), 2.11 (1H, d, J=13.6 Hz), 1.75-1.41 (5H, m), 1.34-1.30 (3H, m), 1.23 (3.5H, s), 1.20 (5.5H, s).

d) 2-{{[2-Chloro-3-(trifluoromethyl)benzoyl]amino}[3-(ethylsulphonyl)phenyl]methyl}piperidinium trifluoroacetate To a mixture of tert-butyl 2-{amino[3-ethylthio)phenyl]methyl}piperidine-1-carboxylate (94 mg, 0.27 mmol), triethylamine (0.102 mL, 0.72 mmol) and 4-N,N-dimethylamino)pyridine (5 mg, 0.04 mmol) in dichloromethane (1 mL) was added 2-chloro-3-(trifluoromethyl)benzoyl chloride (130 mg, 0.54 mmol). This mixture was stirred at ambient temperature for 15 min then treated with methanol (0.5 mL) and concentrated. The residue was treated with methanol (5 mL) and a solution of OXONE® (0.8 mg, 1.3 mmol) in water (4 mL) was added dropwise. The mixture was stirred for 1 h and treated with 0.5M aqueous Na$_2$SO$_3$ and extracted into ethyl acetate. The organic phase was dried (Na$_2$SO$_4$) and concentrated. The residue was purified by preparative TLC (eluting with iso-hexane/ethyl acetate 1:1) to give two diastereoisomers. Both samples were treated independently with 20% trifluoroacetic acid in dichloromethane and after 2 hours at ambient temperature were concentrated to give both possible diastereoisomers of the title product.

(2R*)-2-{(R*)-([2-chloro-3-(trifluoromethyl)benzoyl]amino)[3-(ethylsulphonyl)phenyl]methyl}piperidinium trifluoroacetate. $^1$H NMR (500 MHz, CD$_3$OD): δ 8.03 (1H, s), 7.98 (1H, d, J=7.8 Hz), 7.88 (1H, d, J=6.9 Hz), 7.82 (1H, d, J=7.7 Hz), 7.80 (1H, d, J=7.5 Hz), 7.75 (1H, t, J=7.6 Hz), 7.59 (1H, t, J=7.8 Hz), 5.36 (1H, d, J=9.9 Hz), 3.67-3.63 (1H, m), 3.51 (1H, br d, J=12.5 Hz), 3.25 (2H, q, J=7.4 Hz), 3.06 (1H, dt, J=3.1, 13.0 Hz), 1.96-1.84 (2H, m), 1.75-1.67 (1H, m), 1.60-1.42 (3H, m), 1.23 (3H, t, J=7.4 Hz); MS m/e 489 (M⁺+1).

(2R*)-2-{(S*)-{[2-chloro-3-(fluoromethyl)benzoyl]amino}[3-(ethylsulphonyl)phenyl]methyl}piperidinium trifluoroacetate. ¹H NMR (500 MHz, CD₃OD): δ 8.07 (1H, s), 7.98 (1H, d, J=7.8 Hz), 7.90 (1H, d, J=6.9 Hz), 7.85 (1H, d, J=7.8 Hz), 7.77 (1H, t, J=7.7 Hz), 7.73 (1H, d, J=7.6 Hz), 7.59 (1H, t, J=7.8 Hz), 5.52 (1H, d, J=7.4 Hz), 3.67 (1H, ddd, J=2.8, 7.5, 11.3 Hz), 3.40 (1H, br d, J=12.7 Hz), 3.25 (2H, q, J=7.4 Hz), 3.04 (1H, dt, J=3.2, 12.9 Hz), 2.15 (1H, d, J=11.7 Hz), 1.95 (2H, dd, J=13.3, 29.1 Hz), 1.76-1.54 (3H, m), 1.25 (3H, t, J=7.4 Hz); MS m/e 489 (M⁺+1).

Example 10

2,4-Dichloro-N-(1-{4-[(cyclopropylmethyl)sulphonyl]phenyl}but-3-en-1-yl)benzamide

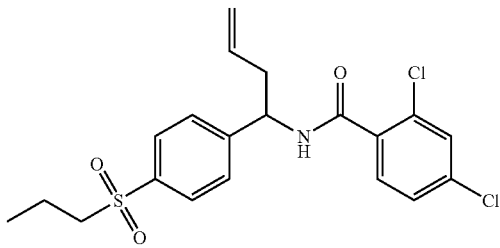

The title compound was obtained from 1-[4-(propylsulphonyl)phenyl]but-3-en-1-ol (prepared as described in Example 3a using the conditions described in Example 2f. ¹H NMR (400 MHz, CD₃OD): δ 1.00 (3H, t, J=7.4 Hz), 1.70-1.80 (2H, m), 2.60-2.72 (2H, m), 3.03-3.07 (2H, m), 5.17 (1H, s), 5.21 (1H, d, J=8.0 Hz), 5.29-5.34 (1H, m), 5.66-5.76 (1H, m), 6.82 (1H, d, J=6.9 Hz), 7.32 (1H, dd, J=8.4, 1.8 Hz), 7.44 (1H, s), 7.54 (2H, d, J=8.2 Hz), 7.66 (1H, d, J=8.3 Hz), 7.88 (2H, d, J=8.2 Hz); MS (ES⁺) m/z 428, 426.

Examples 11-46

The following starting materials were prepared as described below:

a) tert-Butyl 2-(amino{4-[(cyclopropylmethyl)thio]phenyl}methyl)piperidine-1-carboxylate

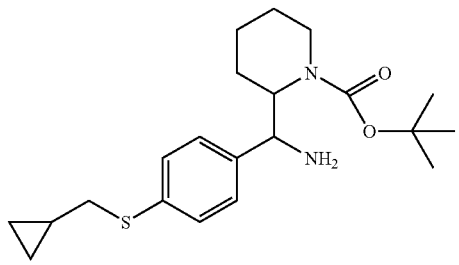

The title compound was prepared from tert-butyl 2-{(Z)-[(tert-butylsulphinyl)imino]methyl}piperidine-1-carboxylate as a 1.5:1 mixture of diastereoisomers using conditions described in Examples 5 and 6 and with the Grignard reagent described in Example 7. ¹H NMR (400 MHz, CDCl₃): δ 7.35-7.20 (4H, m), 4.28-4.14 (2H, m), 3.95 (1H, br), 3.69-3.63 (2H, m), 2.87-2.74 (3H, m), 2.11 (1H, d, J=13.6 Hz), 1.71-1.47 (5H, m), 1.23 (3.6H, s), 1.18 (5.4H, s), 1.03 (1H, m), 0.59-0.55 (2H, m), 0.24 (2H, q, J=5.1).

b) tert-Butyl(2S)-2-{(E)-[(tert-butylsulphinyl)imino]methyl}pyrrolidine-1-carboxylate

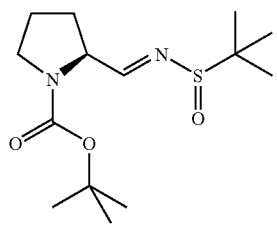

The title compound was prepared from commercially available N-Boc-L-prolinal using conditions described in Examples 5 and 6. ¹H NMR (360 MHz, CDCl₃): δ 7.94 (1H, m), 4.70-4.46 (1H, m), 3.60-3.29 (2H, m), 2.25-1.71 (4H, m), 1.48-1.39 (9H, m), 1.24-1.17 (9H, m).

c) tert-Butyl (2S)-2-(amino{-4-[(cyclopropylmethyl)thio]phenyl}methyl) pyrrolidine-1-carboxylate

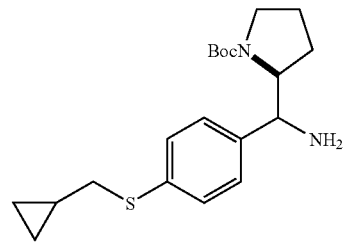

The title compound was prepared from tert-butyl (2S)-2-{(E)-[(tert-butylsulphinyl)imino]methyl}pyrrolidine-1-carboxylate using conditions described in Examples 5 and 6 and with the Grignard reagent described in Example 7. ¹H NMR (400 MHz, CDCl₃): δ 7.40-7.20 (4H, m), 4.72-4.52 (1H, br), 4.08-3.85 (1H, br), 3.70-3.40 (1H, br), 3.35-3.30 (1H, br), 2.85 (2H, d, J=7.0 Hz), 2.00-1.40 (13H, m), 1.09-0.99 (1H, m), 0.56 (2H, q, J=6.1 Hz), 0.23 (2H, q, J=5.1 Hz).

d) tert-Butyl (2R)-2-{(E)-[(tert-butylsulphinyl)imino]methyl}pyrrolidine-1-carboxylate

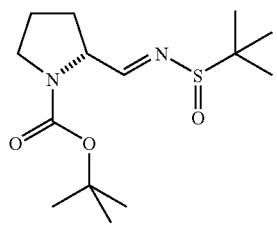

The title compound was prepared from commercially available N-Boc-D-prolinal using conditions described in Examples 5 and 6. ¹H NMR (360 MHz, CDCl₃): δ 7.94 (1H, m), 4.70-4.46 (1H, m), 3.60-3.29 (2H, m), 2.25-1.71 (4H, m), 1.48-1.39 (9H, m), 1.24-1.17 (9H, m).

e) tert-Butyl (2R)-2-(amino{4-[(cyclopropylmethyl)thio]phenyl}methyl)pyrrolidine-1-carboxylate

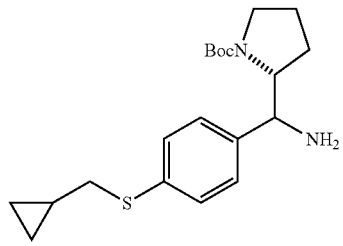

The title compound was prepared from tert-butyl (2R)-2-{(E)-[(tert-butylsulphinyl)imino]methyl}pyrrolidine-1-carboxylate using conditions described in Examples 5 and 6 and with the Grignard reagent described in Example 7. Data identical to those described for tert-butyl (2S)-2-(amino{4-[(cyclopropylmethyl)thio]phenyl}methyl)pyrrolidine-1-carboxylate.

f) tert-Butyl 3-{[methoxy(methyl)amino]carbonyl}-2-azabicyclo[2.2.1]heptane-2-carboxylate

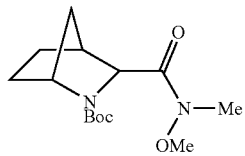

Isopropylmagnesium chloride (41.3 mL of a 2 M solution in THF, 82.6 mmol) was added dropwise to a cooled 0° C. mixture of N,O-dimethylhydroxylamine hydrochloride (4.0 g, 41.3 mmol) and 2-tert-butyl 3-ethyl 2-azabicyclo[2.2.1]heptane-2,3-dicarboxylate (prepared according to procedures described in EP 947506) (7.9 g, 29.5 mmol) in THF (50 mL). The mixture was stirred for 30 min and quenched with saturated aqueous ammonium chloride (50 mL) and 33% aqueous ammonia (50 mL). The mixture was extracted into ethyl acetate (2×100 mL). The combined organic extracts were dried (Na₂SO₄) and concentrated. The residue was purified on silica gel eluting with iso-hexane on a gradient of ethyl acetate (0-60%) to give the title product (6.17 g, 73%). ¹H NMR (400 MHz, CDCl₃, δ 1:1 mixture of rotamers): δ 4.37 (0.5H, s), 4.24 (0.5H, s), 4.13 (0.5H, s), 4.06 (0.5H, s), 3.78-3.71 (3H, m), 3.21-3.19 (3H, m), 2.58 (1H, m), 2.10-2.00 (1H, m), 1.80-1.40 (4H, m), 1.44 (4.5H, s) and 1.39 (4.5H, m), 1.19 (1H, m).

g) tert-Butyl 3-{(E)-[(tert-butylsulphinyl)imino]methyl}-2-azabicyclo[2.2.1]heptane-2-carboxylate

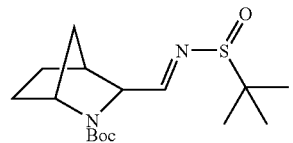

Diisobutylaluminium hydride (50 mL of a 1M solution in toluene, 50 mmol) was added to a pre-cooled (−78° C.) solution of tert-butyl 3-{[methoxy(methyl)amino]-carbonyl}-2-azabicyclo[2.2.1]heptane-2-carboxylate (6.17 g, 21.7 mmol) in diethyl ether (80 mL). The mixture was stirred at −78° C. for 2 hours and then at 0° C. for 10 min. The reaction was poured into a mixture of 1N hydrochloric acid (180 mL), diethyl ether (150 mL) and hexane (150 mL) and stirred for 20 min. The organic layer was washed with brine, dried Na₂SO₄) and concentrated. The residue was treated with THF (90 mL), tert-butylsulphinamide (3.15 g, 26 mmol) and titanium ethoxide (9.1 mL, 43.4 mmol) and stirred at ambient temperature for 12 h. The mixture was treated with brine (120 mL) and ethyl acetate (150 mL) and stirred for 30 min. The organic phase was removed and retained. The aqueous residue was washed with 2 further portions of ethyl acetate. The combined organic extracts were dried (Na₂SO₄) and concentrated. The residue was purified on a pad of silica gel eluting with iso-hexane containing 0.5% triethylamine on a gradient of ethyl acetate (0-40%) to give the title product (6.1 g, 85%). ¹H NMR (400 MHz, CDCl₃): δ 7.94-7.88 (1H, m), 4.33 (0.5H, s), 4.22 (0.5H, s), 4.10 (0.5H, m), 4.02 (0.5H, m), 2.75-2.65 (1.5H, m), 2.58 (0.5H, d, J=5.5), 1.88-1.50 (4H, m), 1.48-1.38 (9H, m), 1.34-1.26 (2H, m), 1.24-1.20 (9H, m).

h) tert-Butyl3-(amino{-4-[(cyclopropylmethyl)thio]phenyl}methyl)-2-azabicyclo[2.2.1]heptane-2-carboxylate

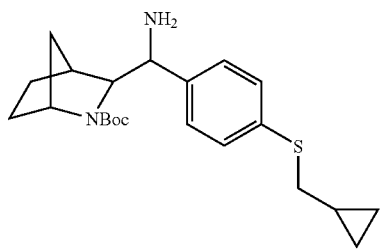

The title compound was prepared from tert-butyl 3-{(E)-[(tert-butylsulphinyl)imino]methyl}-2-azabicyclo[2.2.1]heptane-2-carboxylate using procedures described in Examples 5 and 6 and with the Grignard reagent described in Example 7. Complex NMR due to mixture of diastereoisomers and rotamers. MS m/e 389 (M⁺+1).

i) tert-Butyl (2S)-2-{[methoxy(methyl)amino]carbonyl}azetidine-1-carboxylate

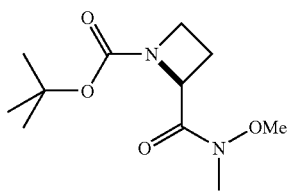

A solution of trimethylsilyldiazomethane in ether (2M, 9 mL) was added dropwise to a stirred, ice-bath cooled, mixture of 1-Boc-L-azetidine-2-carboxylic acid (3 g, 15 mmol), dichloromethane (20 mL) and methanol (5 mL) until yellow colour persisted. The mixture was concentrated in vacuo. The residue was treated with THF (30 mL) and N,O-dimethylhydroxylamine hydrochloride (2.04 g; 20.9 mmol) and cooled to 0° C. i-Propylmagnesium chloride in THF (2 M, 22.4 ml, 44.7 mmol) was added dropwise to the mixture and it was stirred for 30 min. After quenching with saturated aqueous $NH_4Cl$ (25 ml) and concentrated $NH_3$ (25 ml), the mixture was extracted into ethyl acetate (150 mL). The organic extract was dried ($Na_2SO_4$) and concentrated. The residue was purified on silica gel (hexanes-ethyl acetate 0-100%) to give the title product (2.73 g, 75%). $^1$H NMR (500 MB, $CDCl_3$): δ 5.03 (1H, m), 4.05 (1H, m), 3.87 (1H, m), 3.71 (3H, s), 3.22 (3H, s), 2.46 (1H, m), 2.13 (1H, m), 1.43 (9H, s).

j) tert-Butyl (2S)-2-{(E)-[(tert-butylsulphinyl)imino]methyl}azetidine-1-carboxylate

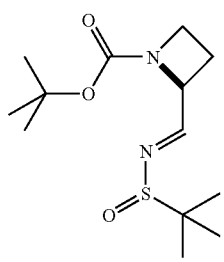

Prepared from tert-butyl (2S)-2-{[methoxy(methyl)amino]carbonyl}azetidine-1-carboxylate as described in part g) above. $^1$H NMR (500 MHz, $CDCl_3$, δ 2.3:1 mixture of diastereoisomers): δ 8.17 (0.3H, d, J=4.9 Hz), 8.16 (0.7H, d, J=4.0 Hz), 4.97 (1H, m), 3.95 (2H, m), 2.51 (1H, m), 2.21 (1H, m), 1.43-1.42 (9H, two s), 1.22-1.21 (9H, two s).

k) tert-Butyl (2S)-2-amino{4-[(cyclopropylmethyl)thio]phenyl}methyl)azetidine-1-carboxylate

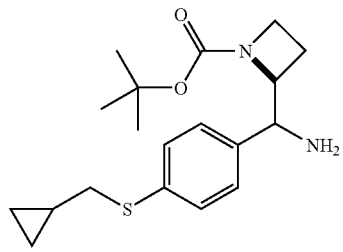

Prepared from tert-butyl (2S)-2-{(E)-[(tert-butylsulphinyl)imino]methyl}azetidine-1-carboxylate using the method described in Examples 5 and 6 using the Grignard reagent described in Example 7. m/e 349 (M$^+$+1).

l) 2-Cyclopropylquinoline-4-carbonyl chloride hydrochloride

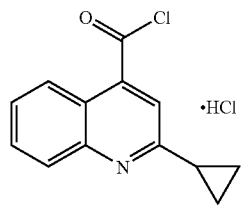

Oxalyl chloride (1.5 ml; 17.5 mmol) was added to a stirred mixture of the acid (1.065 g; 5 mmol), DMF (1 drop) and DCM (20 mL). The mixture was stirred for 2.5 hours and concentrated in vacuo to give the product. $^1$H NMR (360 MHz, $d_6$-DMSO) δ 8.70 (1H, d, J=8.5 Hz), 8.57 (1H, d, J=8.1 Hz), 8.16-8.10 (1H, m), 7.92 (1H, m), 7.80 (1H, s), 3.09-2.99 (1H, m), 1.64-1.52 (4H, m).

General Procedure for Preparation of Examples 11-46

Acid chlorides (70-80 mg) were added to stirred solutions of previously described amines (100 mg), triethylamine (0.15 mL) and DMAP (5 mg) in dichloromethane (1 mL). The mixtures were stirred for 30 min and quenched with saturated aqueous $NaHCO_3$ (2 mL) and extracted twice with 1:1 mixture of hexanes: diethyl ether (2×2 mL). The organic phase was concentrated and filtered through a pad of silica gel (1 g, eluting with iso-hexane/ethyl acetate 1:1) and concentrated to give crude amides. Products containing a basic nitrogen were then converted into their hydrochloride salts by treatment with an excess of 1M hydrogen chloride in ether and subsequent concentration. All samples were then treated with methanol (2 mL) and an aqueous solution of 2 g of Oxone® in 10 mL of water was added drop-wise. The progress of the reactions was monitored by LC-MS. When complete, the reactions were quenched with 0.5M $Na_2SO_3$ (2 mL) and saturated aqueous $NaHCO_3$ (2 mL) and extracted into dichloromethane (3×2 mL). The combined organic phases were dried ($Na_2SO_4$), filtered and concentrated. The residues were then treated at ambient temperature with a 1:2 mixture of trifluoroacetic acid and dichloromethane (3 mL) for 2 hours and concentrated. The residues were purified and where possible separated into individual diastereoisomers by preparative mass-directed HPLC to provide the compounds in the table:
| Ex | Structure And Stereochemistry | m/e (M + 1) |
|---|---|---|
| 11 | 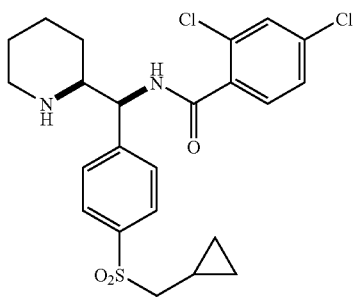 rac | 481 |
| 12 | 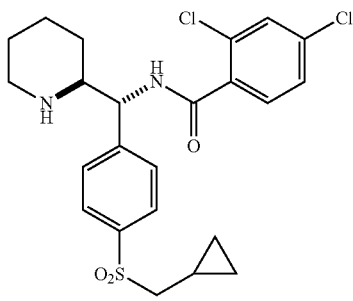 rac | 481 |
| 13 | 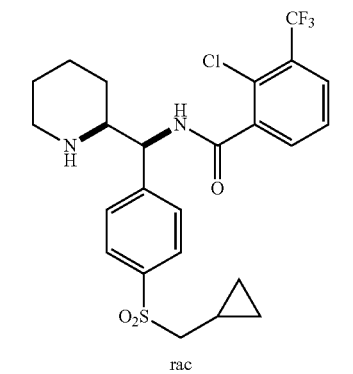 rac | 515 |
| 14 | 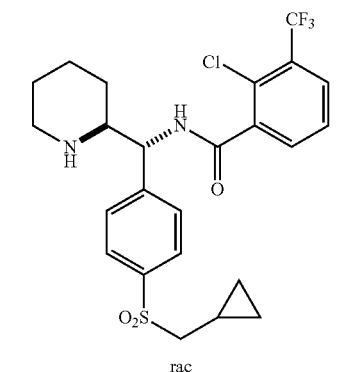 rac | 515 |
| 15 | 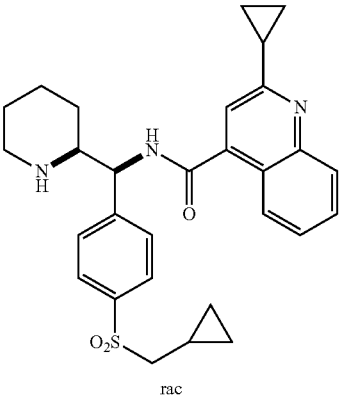 rac | 503 |
| 16 | 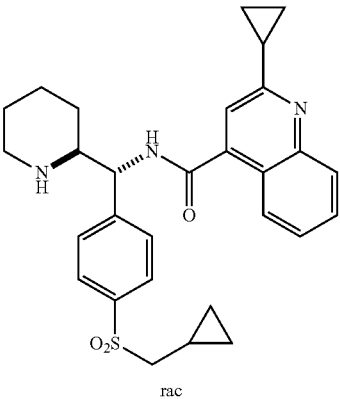 rac | 503 |
| 17 | 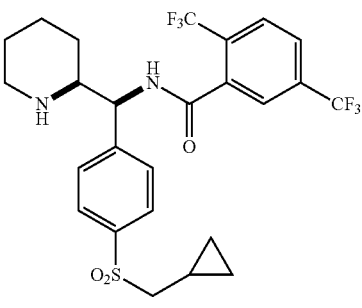 rac | 549 |
| 18 | 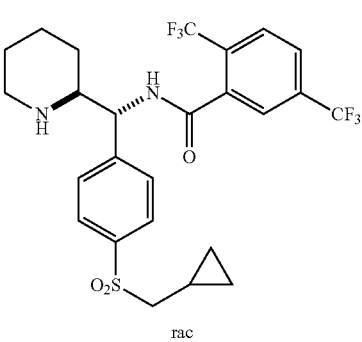 rac | 549 |

-continued
| Ex | Structure And Stereochemistry | m/e (M + 1) |
|---|---|---|
| 19 | 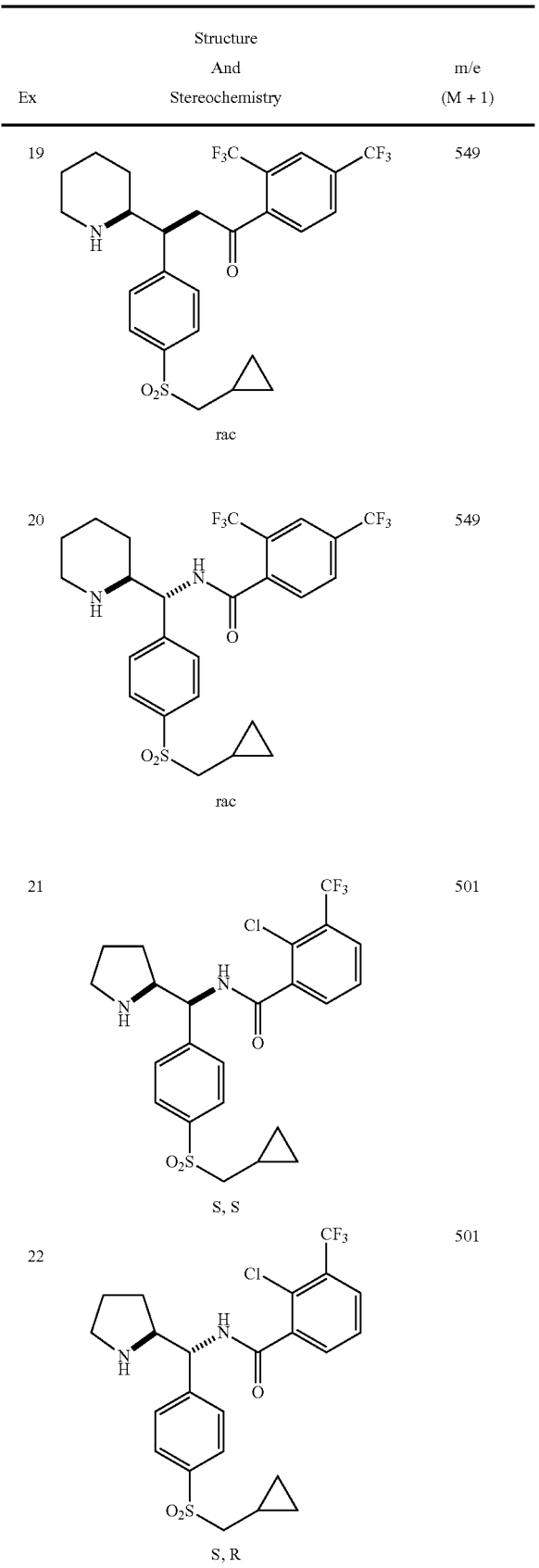 rac | 549 |
| 20 | rac | 549 |
| 21 | S, S | 501 |
| 22 | S, R | 501 |
-continued
| Ex | Structure And Stereochemistry | m/e (M + 1) |
|---|---|---|
| 23 | 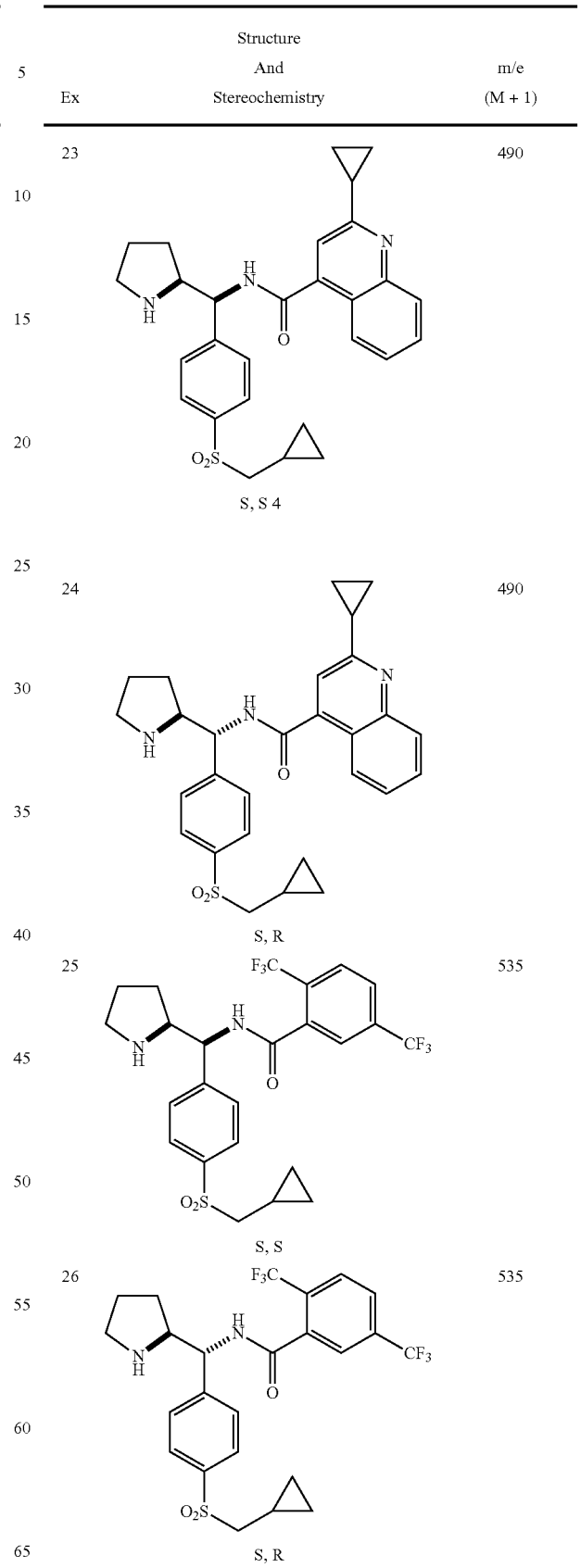 S, S | 490 |
| 24 | S, R | 490 |
| 25 | S, S | 535 |
| 26 | S, R | 535 |

| Ex | Structure And Stereochemistry | m/e (M + 1) |
|---|---|---|
| 27 | 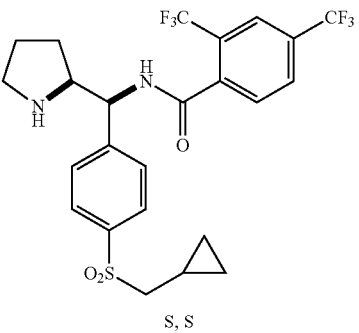<br>S, S | 535 |
| 28 | 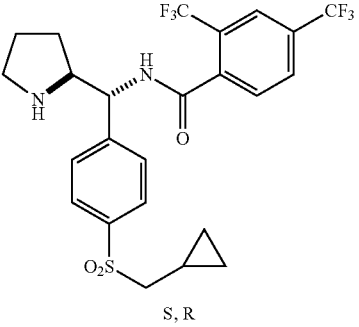<br>S, R | 535 |
| 29 | 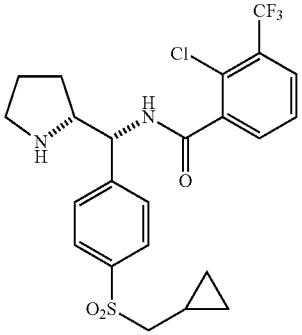<br>R, R | 501 |
| 30 | 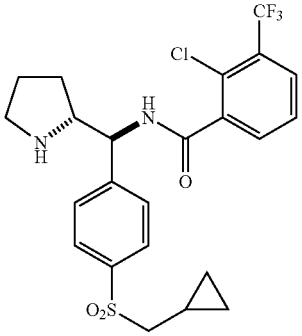<br>R, S | 501 |
| Ex | Structure And Stereochemistry | m/e (M + 1) |
|---|---|---|
| 31 | 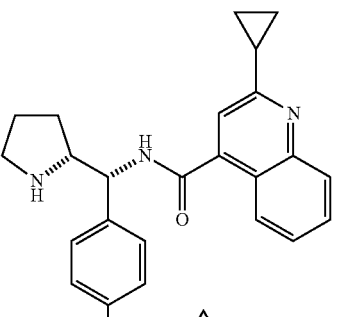<br>R, R | 490 |
| 32 | 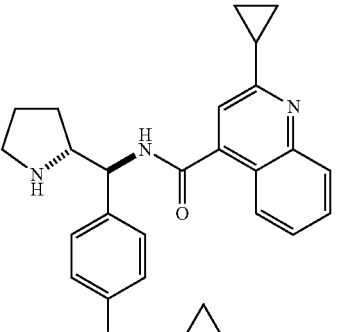<br>R, S | 490 |
| 33 | 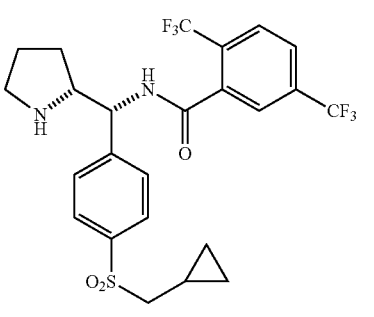<br>R, R | 535 |
| 34 | 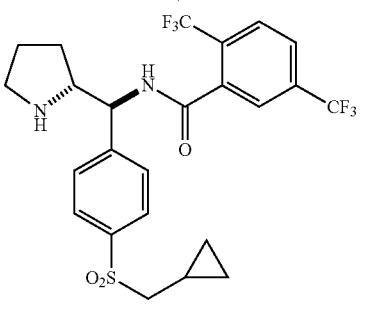<br>R, S | 535 |

| Ex | Structure And Stereochemistry | m/e (M + 1) |
|---|---|---|
| 35 | 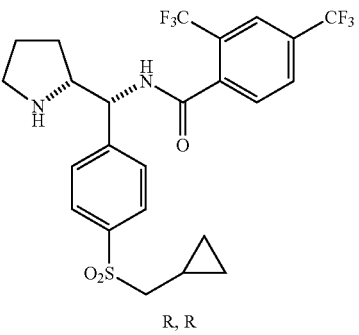 R, R | 535 |
| 36 | 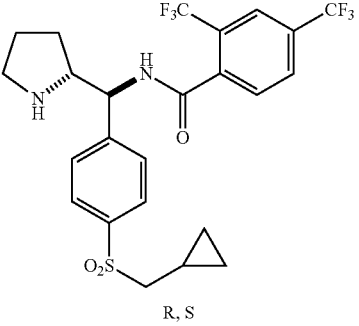 R, S | 535 |
| 37 | 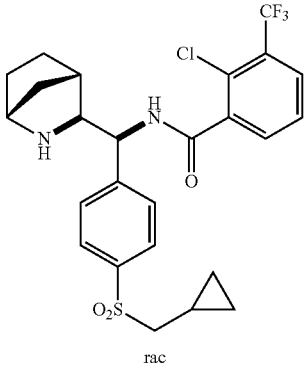 rac | 527 |
| 38 | 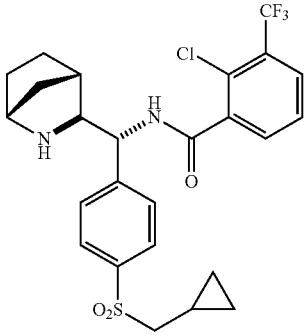 R, S | 527 |
| Ex | Structure And Stereochemistry | m/e (M + 1) |
|---|---|---|
| 39 | 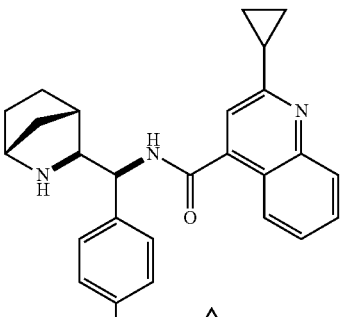 rac | 517 |
| 40 | 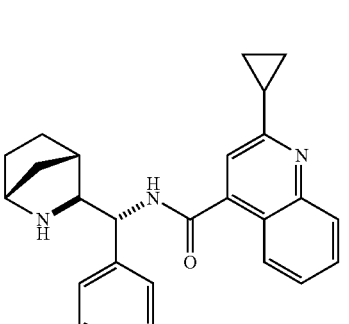 rac | 517 |
| 41 | 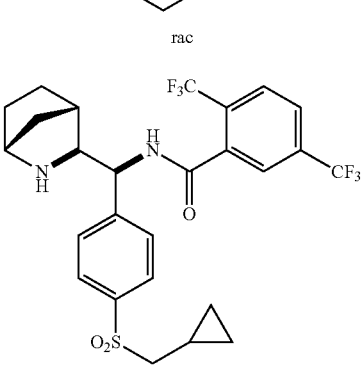 rac | 561 |
| 42 | 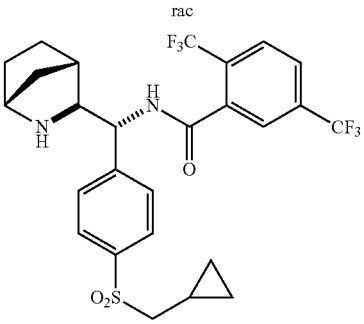 rac | 561 |

| Ex | Structure And Stereochemistry | m/e (M + 1) |
|---|---|---|
| 43 | ![structure] rac | 561 |
| 44 | ![structure] rac | 561 |
| 45 | ![structure] S, R | 489 487 |
| 46 | ![structure] S, SR | 455 453 |

Example 47

2,4-Dichloro-N-{1-[4-(propylsulphonyl)phenyl]-2-pyrrolidin-1-ylethyl}benzamide

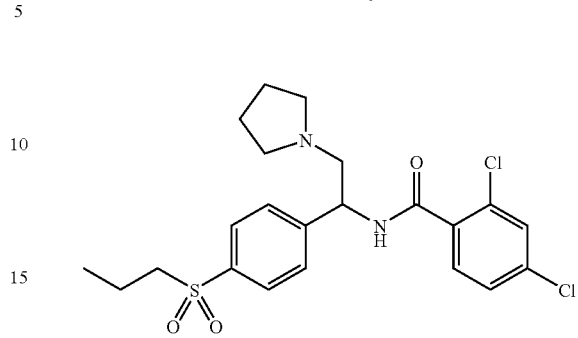

a) 4-(Propylsulphonyl)benzaldehyde

4-Fluorobenzaldehyde (3.03 mL, 28.2 mmol) and sodium n-propylsulphinate (4.03 g, 31.0 mmol, synthesised as described in *J. Med. Chem.* 1989, 32, 2436) were dissolved in dry DMSO and the resulting solution heated at 100° C. for 18 h. The mixture was allowed to cool and then poured onto approximately 50 g of ice. After the ice had melted, the product was extracted into ethyl acetate (×2). The combined organic extracts were dried (MgSO$_4$) and concentrated. Chromatography on silica eluting with 20 to 40% ethyl acetate in hexane afforded the product as a white solid (3.21 g, 54% yield). $^1$H NMR (400 MHz, CDCl$_3$) δ 1.02 (3H, t, J=7.5 Hz), 1.72-1.82 (2H, m), 3.10-3.14 (2H, m), 8.07-8.11 (4H, m), 10.14 (1H, s).

b) (Diallylamino)[4-propylsulphonyl)phenyl]acetonitrile

Diallylamine (0.58 mL, 4.71 mmol) was stirred with hydrochloric acid (4.71 mL of 1M aqueous solution, 4.71 mmol) for 5 minutes. Potassium cyanide (307 mg, 4.71 mmol) was added and the mixture stirred for a further 10 mins before addition of 4-(propylsulphonyl)benzaldehyde (1.00 g, 4.71 mmol). The reaction mixture was stirred at 60° C. for 16 h. After cooling to ambient temperature, the mixture was treated with saturated aqueous NaHCO$_3$ and extracted with ethyl acetate (×2). The combined organic extracts were dried (MgSO$_4$) and concentrated. Chromatography on silica eluting with 30% ethyl acetate in hexane afforded the title compound (1.22 g, 81% yield). $^1$H NMR (400 MHz, CDCl$_3$) δ 1.01 (3H, t, J=7.5 Hz), 1.71-1.81 (2H, m), 2.97 (2H, dd, J=14.0, 8.4 Hz), 3.06-3.10 (2H, m), 3.31-3.36 (2H, m), 5.16 (1H, s), 5.24 (2H, d, J=10.2 Hz), 5.33 (2H, d, J=17.1 Hz), 5.73-5.83 (2H, m), 7.78 (2H, d, J=8.2 Hz), 7.94 (2H, d, J=8.4 Hz); m/z (ES+) 319 (M+H), 292 (M−CN), 252 (M−[CN+allyl]).

c) N$^1$,N$^1$-Diallyl-1-[4-(propylsulphonyl)phenyl]ethane-1,2-diamine

Anhydrous THF (5 mL) was cooled to 0° C. and treated with 98% sulphuric acid (0.28 mL, 5.25 mmol). After stirring for 15 mins, lithium aluminium hydride (10.5 mL of 1.0M solution in THF, 10.5 mmol) was added drop wise over 10 mins. The mixture was stirred at 0° C. for 60 minutes before addition of a solution of (diallylamino)[4-(propylsulphonyl)phenyl]acetonitrile (1.22 g, 3.83 mmol) in THF (3+2 mL washing). The mixture was stirred at 0° C. for 30 mins then at 40° C. for 1 h. The reaction was allowed to cool and carefully treated with powdered sodium sulphate decahydrate (3 g). The mixture was stirred at ambient temperature for 15 h, then filtered and the filtrate concentrated to give a pale yellow oil. Used without further purification. $^1$H NMR (400 MHz, CDCl$_3$) δ 1.01 (3H, t, J=7.4 Hz), 1.75-1.81 (2H, m), 2.82 (2H, dd, J=14.6, 7.6 Hz), 2.95 (1H, dd, J=13.0, 6.0 Hz), 3.06-3.10 (2H, m), 3.18 (1H, dd, J=13.1, 7.5 Hz), 3.28-3.33 (2H, m), 3.86 (1H, br t, J=67 Hz), 5.15-5.20 (4H, m), 5.77-5.85 (2H, m), 7.44 (2H, d, J=8.3 Hz), 7.88 (2H, d, J=8.3 Hz); m/z (ES+) 323 (M+H), 306 (M−NH$_2$).

d) Diallyl {1-[4-(propylsulphonyl)phenyl]-2-pyrrolidin-1-ylethyl}amine

N$^1$,N$^1$-Diallyl-1-[4-(propylsulphonyl)phenyl]ethane-1,2-diamine (445 mg, 1.38 mmol), 1,4-dibromobutane (0.18 mL, 1.51 mmol) and sodium hydrogencarbonate (0.26 g, 3.09 mmol) were heated in toluene at reflux for 17 h. The reaction mixture was allowed to cool to ambient temperature, filtered through Celite and the filter cake washed with ethyl acetate. The filtrate was washed with water and then brine before being dried (MgSO$_4$) and concentrated. The crude product was purified using an SCX cartridge eluting with dichloromethane, then methanol and finally 2M ammonia in methanol to give the title compound as a pale yellow oil (266 mg, 51% yield). $^1$H NMR (400 MHz, CDCl$_3$) δ 1.00 (3H, t, J=7.5 Hz), 1.69-1.80 (6H, m), 2.45-2.54 (4H, m), 2.83-3.00 (4H, m), 3.05-3.09 (2H, m), 3.21 (2H, dd, J=14.4, 6.0 Hz), 4.07 (1H, dd, J=8.3, 5.2 Hz), 5.11-5.19 (4H, m), 5.76-5.84 (2H, m), 7.58 (2H, d, J=8.3 Hz), 7.83 (2H, d, J=8.4 Hz); m/z (ES+) 377 (M+H), 280 (M−N[allyl]$_2$).

e) {1-[4-Propylsulphonyl)phenyl]-2-pyrrolidin-1-ylethyl}amine

To a solution of diallyl{1-[4-(propylsulphonyl)phenyl]-2-pyrrolidin-1-ylethyl}amine (266 mg, 0.706 mmol) in anhydrous dichloromethane (8 mL) were added 1,3-dimethylbarbituric acid (0.44 g, 2.82 mmol) and tetrakis(triphenylphosphine)-palladium(0) (41 mg, 0.0355 mmol). The mixture was heated at reflux for 1 h after which time NMR analysis indicated incomplete reaction. A further portion of 1,3-dimethylbarbituric acid (0.22 g, 1.41 mmol) was added and the mixture heated at reflux for 6 h. On cooling, the mixture was concentrated in vacuo and then purified using an SCX cartridge eluting with dichloromethane, then methanol and finally 2M ammonia in methanol. The title compound was obtained as a colorless oil (202 mg, 96%). $^1$H NMR δ (400 MHz, CDCl$_3$) δ 0.99 (3H, t, J=7.4 Hz), 1.71-1.79 (6H, m), 2.39 (1H, dd, J=12.0, 3.8 Hz), 2.49-2.51 (2H, m), 2.64-2.76 (3H, m), 3.03-3.07 (2H, m), 4.18 (1H, dd, J=10.2, 3.7 Hz), 7.60 (2H, d, J=8.3 Hz), 7.85 (2H, d, J=8.4 Hz); m/z (ES+) 280 (M−NH$_2$).

f) 2,4-Dichloro-N-{1-[4-(propylsulphonyl)phenyl]-2-pyrrolidin-1-ylethyl}benzamide To a solution of {1-[4-(propylsulphonyl)phenyl]-2-pyrrolidin-1-ylethyl}amine (100 mg, 0.337 mmol) in dichloromethane (5 mL) under nitrogen was added triethylamine (47 □L, 0.337 mmol) followed by 2,4-dichlorobenzoyl chloride (47 □L, 0.336 mmol). The mixture was stirred at ambient temperature for 2 h, then diluted with water and extracted with ethyl acetate (×2). The combined organic extracts were washed with brine, dried (MgSO$_4$) and concentrated. The product was purified by chromatography on silica eluting with 3% MeOH in dichloromethane to give the product as an off-white solid (123 mg, 78%). $^1$H NMR δ (400 MHz, CDCl$_3$) δ 1.00 (3H, t, J=7.4 Hz), 1.69-1.81 (6H, m), 2.46-2.49 (2H, m), 2.58-2.62 (2H, m), 2.73 (1H, dd, J=12.5, 5.1 Hz), 2.91 (1H, dd, J=12.52, 9.5 Hz), 3.03-3.07 (2H, m), 5.01-5.09 (1H, m), 7.33 (1H, dd, J=8.3, 1.9 Hz), 7.46 (1H, d, J=1.9 Hz), 7.56 (2H, d, J=8.3 Hz), 7.64 (1H, d, J=8.3 Hz), 7.72 (1H, br d, J=3.9 Hz), 7.87 (2H, d, J=8.32 Hz); m/z (ES+) 471 (M+H), 469 (M+H), 400 (M-pyrrolidine), 398 (M-pyrrolidine).

Example 48

2-Cyclopropyl-N-{1-[4-(propylsulphonyl)phenyl]-2-pyrrolidin-1-ylethyl}quinoline-4-carboxamide

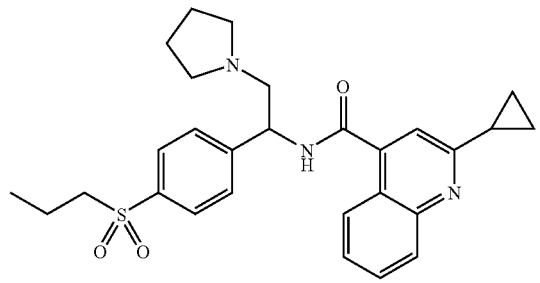

{1-[4-(Propylsulphonyl)phenyl]-2-pyrrolidin-1-ylethyl}amine, the intermediate described in Example 47e, was reacted with 2-cyclopropylquinoline-4-carbonyl chloride (see above) under the conditions described in Example 47f. $^1$H NMR δ (400 MHz, CDCl$_3$) δ 0.97 (3H, t, J=7.4 Hz), 1.07-1.11 (2H, m), 1.16-1.20 (2H, m), 1.66-1.77 (6H, m), 2.18-2.24 (1H, m), 2.48-2.50 (2H, m), 2.63-2.71 (3H, m), 2.91-3.02 (3H, m), 5.19-5.24 (1H, m), 7.29 (1H, s), 7.42-7.48 (2H, m), 7.56 (2H, d, J=8.3 Hz), 7.62-7.66 (1H, m), 7.82 (2H, d, J=8.3 Hz), 7.96 (1H, d, J=8.4 Hz), 8.13 (1H, d, J=8.3 Hz); m/z (ES+) 492 (M+H).

Example 49

2,4-Dichloro-N-{2-morpholin-4-yl-1-[4-(propylsulphonyl)phenyl]ethyl}benzamide

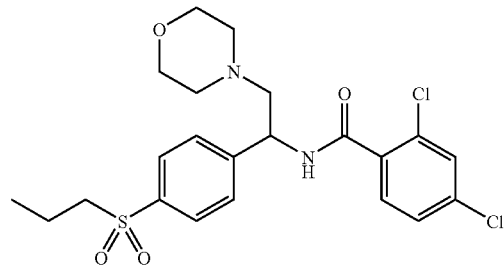

a) N-Allyl-N-{2-morpholin-4-yl-1-[4-(propylsulphonyl)phenyl]ethyl}prop-2-en-1-amine N$^1$,N$^1$-Diallyl-1-[4-propylsulphonyl)phenyl]ethane-1,2-diamine (375 mg, 1.16 mmol, prepared as described in Example 47c, 2-bromoethyl ether (0.15 mL, 1.16 mmol) and sodium carbonate (0.62 g, 5.81 mmol) were heated at 60° C. overnight. The mixture was concentrated in vacuo, diluted with water and extracted into ethyl acetate (×2). The combined organic extracts were washed with brine, dried (MgSO$_4$) and concentrated to give the title compound. m/z (ES+) 393 (M+H).

b) 2,4-Dichloro-N-{2-morpholin-4-yl-1-[4-(propylsulphonyl)phenyl]ethyl}-benzamide N-Allyl-N-{2-morpholine-4-yl-[4-(propylsulphonyl)phenyl]ethyl}prop-2-en-1-amine was converted to the title compound using the conditions described in Example 47 steps e and f; $^1$H NMR δ (400 MHz, CDCl$_3$) δ 1.01 (3H, t, J=7.4 Hz), 1.72-1.79 (2H, m), 2.40 (2H, br s), 2.60 (2H, br s), 2.68 (2H, d, J=6.6 Hz), 3.04-3.06 (2H, m), 3.66-3.70 (4H, br s), 5.12-5.16 (1H, m), 7.35 (1H, dd, J=1.8, 8.3 Hz), 7.49 (1H, d, J=1.8 Hz), 7.54-7.58 (3H, m), 7.70 (1H, d, J=8.3 Hz), 7.89 (2H, d, J=8.2 Hz); m/z (ES+) 487 (M+H), 485 (M+H), 400, 398.

Example 50

2,4-Dichloro-N-{2-piperidin-1-yl-1-[4-(propylsulphonyl)phenyl]ethyl}benzamide

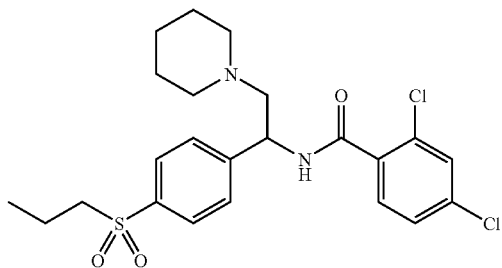

a) 2-Methyl-N-{(1E)-[4-(propylsulphonyl)phenyl]methylene}propane-2-sulphinamide 4-(Propylsulphonyl)benzaldehyde (1.81 g, 8.53 mmol, prepared as described in Example 47a, tert-butyl sulphinamide (1.55 g, 12.8 mmol), titanium(V) ethoxide (3.58 mL, 17.1 mmol) and THF (50 mL) were heated at reflux for 3 h then stirred at room temperature overnight. The reaction mixture was quenched with water (200 mL) before addition of ethyl acetate (200 mL). Celite was added and the mixture stirred for 15 min before being filtered. The phases were separated and the organic extract dried (MgSO$_4$) and concentrated. The yield of the title compound was assumed to be quantitative and the material was used without further purification. m/z (ES+) 316 (M+H).

b) 1(tert-Butylsulphinyl)-2-[4-(propylsulphonyl)phenyl]aziridine

Sodium hydride (0.33 g of a 60% dispersion in mineral oil, 8.37 mmol) was added portionwise to a stirred solution of trimethylsulphoxonium iodide (1.84 g, 8.37 mmol) in DMSO (30 mL). The mixture was stirred at room temperature for 1 h by which time effervescence had ceased and the mixture was mostly clear. 2-Methyl-N-{(1E)-[4-(propylsulphonyl)phenyl]methylene}propane-2-sulphinamide (1.76 g, 5.58 mmol) was added and the resulting solution stirred at room temperature overnight. The reaction mixture was quenched by addition of water and the product extracted into ethyl acetate (×2). The combined organic extracts were washed with brine, dried (MgSO$_4$) and concentrated to give the title compound (1.44 g, 88% yield).

c) 2-Piperidin-1-yl-1-[4-(propylsulphonyl)phenyl]ethanamine and 2-Piperidin-1-yl-2-[4-(propylsulphonyl)phenyl]ethanamine A solution of the aziridine (232 mg, 0.704 mmol) and piperidine (0.14 mL, 1.41 mmol) in DMSO (2 mL) was heated in the microwave at 160° C. for 20 min. The mixture was diluted with ethyl acetate and washed with water (×3) and then brine before being dried (MgSO$_4$) and concentrated. The crude material was dissolved in methanol (4 mL) and a solution of concentrated HCl in methanol (2 mL) was added. After 1 h, the mixture was concentrated in vacuo to give a mixture of the title compounds. m/z (ES+) 311 (M+H).

d) 2,4-Dichloro-N-{2-piperidin-1-yl-1-[4-(propylsulphonyl)phenyl]ethyl}benzamide The title compound together with the regioisomer arising from aroylation of 2-piperidin-1-yl-2-[4-(propylsulphonyl)phenyl]ethanamine were synthesised using the procedure outlined in Example 47f. The title compound was obtained following chromatography on silica eluting with 5% methanol in dichloromethane and then purification using mass-directed HPLC. $^1$H NMR δ (400 MHz, CDCl$_3$) δ 0.83-0.89 (2H, m), 1.00 (3H, t, J=7.4 Hz), 1.43-1.62 (4H, m), 1.72-1.81 (2H, m), 2.31 (2H, br s), 2.55 (2H, br s), 2.61 (2H, d, J=5.8 Hz), 3.03-3.07 (2H, m), 5.05-5.10 (1H, m), 7.34 (1H, dd, J=2.0, 8.4 Hz), 7.47 (1H, d, J=2.0 Hz), 7.54 (2H, d, J=8.3 Hz), 7.68 (1H, d, J=8.3 Hz), 7.78 (1H, s), 7.87 (2H, d, J=8.3 Hz).

Example 51

2,4-Dichloro-N-{2-(diethylamino)-1-[4-(propylsulphonyl)phenyl]ethyl}benzamide

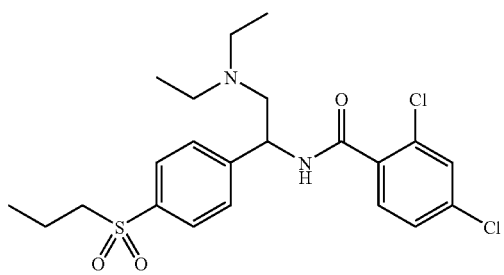

a) $N^2,N^2$-Diethyl-1-[4-(propylsulphonyl)phenyl]ethane-1,2-diamine

To a solution of $N^1,N^1$-diallyl-1-[4-(propylsulphonyl)phenyl]ethane-1,2-diamine (473 mg, 1.47 mmol, prepared as described in Example 47c in methanol (10 mL) was added acetaldehyde (approximately 0.5 mL, approx. 9 mmol), acetic acid (0.42 mL, 7.3 mmol) and finally, sodium cyanoborohydride (203 mg, 3.2 mmol). The mixture was stirred at room temperature, under nitrogen, overnight and then quenched by addition of satd. NaHCO$_3$(aq). Methanol was removed in vacuo, the residue diluted with water and the product extracted into ethyl acetate (×3). The combined organic extracts were washed with brine, dried (MgSO$_4$) and concentrated. The crude material was dissolved in dichloromethane and to this solution was added 1,3-dimethylbarbituric acid (1.37 g, 8.8 mmol) and palladium (tetrakis)triphenylphosphine (85 mg, 0.07 mmol). The mixture was heated at reflux for 6 h, then cooled and concentrated. The title compound was partially purified using an SCX cartridge (330 mg obtained, 75% yield over two steps, approximate since not pure). m/z (ES+) 282 (M–NH$_2$).

b) 2,4-Dichloro-N-{2-(diethylamino)-1-[4-(propylsulphonyl)phenyl]ethyl}-benzamide The title compound was prepared from N$^2$,N$^2$-diethyl-1-[4-propylsulphonyl)phenyl]thane-1,2-diamine using the procedure outlined in Example 47f. Purification by preparative HPLC gave the title compound. m/z (ES+) 473 (M+H), 471 (M+H), 398 (M–NEt$_2$).

Example 52

2,4-Dichloro-N-{2-[(2R)-2-(methoxymethyl)pyrrolidin-1-yl]-1-[4-(propylsulphonyl)-phenyl]ethyl}benzamide

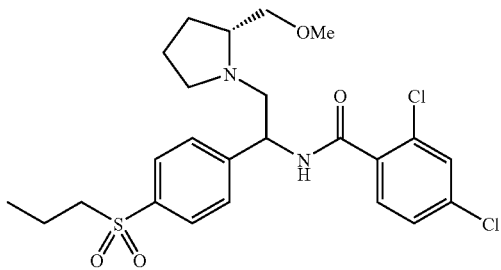

a) 2-Methyl-N-{1-[4-(propylsulphonyl)phenyl]prop-2-en-1-yl}propane-2-sulphinamide Vinylmagnesium bromide (3.3 mL of a 1.0 M solution in THF, 3.3 mmol) was added dropwise to a solution of 2-methyl-N-{(1E)-[4-(propylsulphonyl)phenyl]methylene}-propane-2-sulphinamide (1.0 g, 3.17 mmol, prepared as described in Example 50a in THF (15 mL) at –78° C. The mixture was stirred at –78° C. for 6 h and then allowed to warm to room temperature overnight. The reaction mixture was quenched by addition of saturated NH$_4$Cl$_{(aq)}$ and the product extracted into ethyl acetate (×2). The combined organic extracts were dried (MgSO$_4$) and concentrated. The product was purified by gradient chromatography on silica eluting with 30 to 80% ethyl acetate in hexane giving the title compound as a yellow solid (485 mg, 45% yield). m/z (ES+) 366 (M+Na), 344 (M+H).

b) 2,4-Dichloro-N-{1-[4-(propylsulphonyl)phenyl]prop-2-en-1-yl}benzamide

2-Methyl-N-{1-[4-(propylsulphonyl)phenyl]prop-2-en-1-yl}propane-2-sulphinamide (213 mg, 0.62 mmol) was dissolved in methanol. Methanolic hydrogen chloride was added and the reaction mixture was stirred at room temperature for 2 h. Following concentration in vacuo the residue was suspended in dichloromethane and stirred under nitrogen. Triethylamine (0.173 mL, 1.24 mmol) was added followed by 2,4-dichlorobenzoyl chloride (87 µL, 0.62 mmol) and the reaction mixture was stirred overnight. The reaction was quenched by addition of water and satd. NaHCO$_3$(aq). The product was extracted into ethyl acetate (×2) and then the combined organic layers washed with brine, dried (MgSO$_4$) and concentrated. $^1$H NMR 5 (400 MHz, CDCl$_3$) δ 0.99 (3H, t, J=7.4 Hz), 1.66-1.76 (2H, m), 3.00-3.04 (2H, m), 5.30-5.37 (2H, m), 5.86 (1H, t, J=6.9 Hz), 6.02-6.10 (1H, m), 7.19 (1H, d, J=7.9 Hz), 7.29 (1H, dd, J=8.5, 2.1 Hz), 7.40 (1H, d, J=1.9 Hz), 7.56 (2H, dd, J=8.3, 2.5 Hz), 7.83 (2H, d, J=8.3 Hz).

c) 2-4-Dichloro-N-{2,3-dihydroxy-1-[4-(propylsulphonyl)phenyl]propyl}-benzamide

To a stirred solution of the alkene from Example 52b (358 mg, 0.87 mmol) in 2:1 acetonitrile:water (6 mL:3 mL) was added 4-methylmorpholine N-oxide (0.20 g, 1.7 mmol) followed by osmium tetroxide solution (0.55 mL of a 4 wt. % in water, 0.087 mmol). The mixture was stirred overnight at room temperature, sealed apart from a narrow gauge vent to an oil bubbler. The reaction was quenched by addition of saturated sodium thiosulphate solution (aq.) and the product extracted into dichloromethane (×3). The combined organic extracts were dried (MgSO$_4$) and concentrated. Chromatography on silica afforded the title compound (337 mg, 87% yield). m/z (ES+) 448 (M+H), 446 (M+H).

d) 2,4-Dichloro-N-{2-oxo-1-[4-(propylsulphonyl)phenyl]ethyl}benzamide

To a solution of 2-4-dichloro-N-{2,3-dihydroxy-1-[4-(propylsulphonyl)phenyl]propyl-benzamide (325 mg, 0.73 mmol) in THF (6 mL) at 0° C. was added sodium periodate (312 mg, 1.46 mmol) followed by water (3 mL). The reaction mixture was stirred at room temperature for 1 h, then quenched by addition of saturated aqueous sodium thiosulphate solution. The product was extracted into ethyl acetate (×3) and the combined organic layers washed with brine, dried (MgSO$_4$) and concentrated. The title compound was used without further purification.

e) 2,4-Dichloro-N-{2-[(2R)-2-(methoxymethyl)pyrrolidin-1-yl]-1-[4-(propylsulphonyl)-phenyl]ethyl}benzamide To a solution of 2,4-dichloro-N-{2-oxo-1-[4-(propylsulphonyl)phenyl]-ethyl}benzamide (135 mg, 0.33 mmol) in 1,2-dichloroethane (5 mL) under nitrogen was added (R)-2-(methoxymethyl)pyrrolidine (81 µL, 0.66 mmol) followed by sodium triacetoxyborohydride (138 mg, 0.65 mmol) and the resulting mixture was stirred at room temperature overnight. The reaction mixture was quenched by addition of satd. NaHCO$_3$(aq) and the product extracted into ethyl acetate (×2). The combined organic extracts were washed with brine, dried (MgSO$_4$) and concentrated. One diastereoisomer of the title compound was isolated in pure form following preparative HPLC. $^1$H NMR δ (400 MHz, CDCl$_3$) δ 1.00 (3H, t, J=7.4 Hz), 1.32-1.40 (1H, m), 1.52-1.59 (2H, m), 1.71-1.82 (4H, m), 1.96-2.04 (1H, m), 2.37-2.42 (1H, m), 2.87 (1H, br s), 3.00 (3H, s), 3.03-3.07 (2H, m), 3.21-3.35 (3H, m), 5.15-5.19 (1H, m), 7.34 (1H, dd, J=1.9, 8.3 Hz), 7.47 (1H, d, J=1.9 Hz), 7.59-7.61 (3H, m), 7.87 (2H, d, J=8.3 Hz), 8.31 (1H, d, J=5.3 Hz); m/z (ES+) 515 (M+H), 513 (M+H).

Example 53

2,4-Dichloro-N-[{4-[(cyclopropylmethyl)sulphonyl]phenyl}(pyridin-3-yl)methyl]benzamide

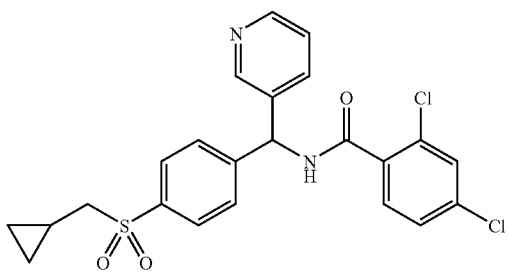

a) 4-[(Cyclopropylmethyl)thio]benzaldehyde

4-Bromothiophenol (106.12 g, 561 mmol), cyclopropylmethyl bromide (83.3 g, 617 mmol) and potassium carbonate (85.2 g, 617 mmol) were stirred in DMF (400 mL) overnight. The mixture was diluted with water (1.5 L) and the product extracted into hexanes (2×1 L). The combined organic extracts were dried ($MgSO_4$) and concentrated to give 4-bromophenyl cyclopropylmethyl sulphide as an oil (130.7 g, quantitative). The aforementioned sulphide (10 g, 41 mmol) was dissolved in THF (400 mL) and cooled to −78° C. n-Butyllithium (51 mL of a 1.6 M solution in hexanes) was added dropwise. On completion of addition, the mixture was stirred for a further 15 min before dropwise addition of DMF. The reaction mixture was stirred for 18 h, allowing to warm to room temperature. The reaction was quenched by addition of satd. $NH_4Cl$(aq) followed by water. The product was extracted into diethyl ether (×2) and the combined organic layers were dried ($MgSO_4$) and concentrated. Purification by chromatography on silica eluting with 5 to 10% ethyl acetate in hexane gave the title compound (5.50 g, 70% yield). $^1$H NMR δ (360 MHz, $CDCl_3$) δ 9.92 (1H, s), 7.76 (2H, d, J=8.4 Hz), 7.38 (2H, d, J=8.2 Hz), 2.97 (2H, d, J=7.0 Hz), 1.14-1.08 (1H, m), 0.67-0.62 (2H, m) 0.35-0.30 (2H, m).

b) N-((1E)-{4-[(cyclopropylmethyl)thio]phenyl}methylene-2-methylpropane-2-sulphinamide To a solution of 4-[(cyclopropylmethyl)thio]benzaldehyde (5.64 g, 29.4 mmol) in THF (250 mL) was added tert-butyl sulphinamide (5.4 g, 44 mmol) and titanium(IV) ethoxide (12.6 mL, 60 mmol). The reaction mixture was stirred at room temperature for 3 d then quenched with water (250 mL) and ethyl acetate (250 mL). The mixture was stirred vigorously for 30 min then filtered through Celite, washing well with ethyl acetate. The organic phase was separated, dried ($MgSO_4$) and concentrated to give the title compound as an oil. $^1$H NMR δ (360 MHz, $CDCl_3$) δ 8.52 (1H, s), 7.74 (2H, d, J=8.3 Hz), 7.36 (2H, d, J=8.4 Hz), 2.95 (2H, d, J=7.0 Hz), 1.26 (9H, s), 1.14-1.06 (1H, m), 0.66-0.60 (2H, m), 0.34-0.29 (2H, m).

c) N-[{4-(cyclopropylmethyl)thio)phenyl}(pyridin-3-yl)methyl]-2-methylpropane-2-sulphinamide To i-PrMgCl.LiCl solution (8.0 mL of a 1M solution in THF, 8 mmol, prepared as described in *Angewandte Chem.* *Int. Ed. Engl.* 2004, 43, 3333) at −15° C. was added 3-bromopyridine (0.77 mL, 8 mmol). The mixture was stirred at −10° C. for 1 h and then at 0° C. for 1 h after which time it was added to a solution of N-(1E)-{4-[(cyclopropylmethyl)-sulphonyl]phenyl}methylene)-2-methylpropane-2-sulphinamide (1.18 g, 4 mmol) in THF (40 mL) at −78° C. The reaction mixture was stirred at −78° C. for 30 min, then allowed to warm to room temperature and stirred for a further 2 h. The mixture was quenched with water and extracted with ethyl acetate (×2). The combined organic extracts were dried ($MgSO_4$) and concentrated. Purification by chromatography on silica eluting with 20 to 50 to 75% ethyl acetate in hexane, then 5% methanol in ethyl acetate gave the title compound as a gum (695 mg, 46% yield). $^1$H NMR δ (360 MHz, $CDCl_3$) δ 8.69 (1H, s), 8.53-8.52 (1H, m), 7.68 (1H, br d, J=7.8 Hz), 7.32-7.25 (6H, m), 5.63 (1H, d, J=2.3 Hz), 2.84 (2H, d, J=7.0 Hz), 1.26 (9H, s), 1.09-0.98 (1H, m), 0.60-0.55 (2H, m), 0.27-0.23 (2H, m).

d) 2,4-Dichloro-N-[{-4-[(cyclopropylmethyl)sulphonyl]phenyl}(pyridin-3-yl)methyl]benzamide A solution of N-[{4-[(cyclopropylmethyl)sulphonyl]phenyl}(pyridin-3-yl)methyl]-2-methylpropane-2-sulphinamide (900 mg, 2.4 mmol) in methanol (10 mL) was treated with HCl/methanol which had been formed by dropwise addition of acetyl chloride (426 μL, 6 mmol) to methanol (10 mL). The mixture was stirred at room temperature for 30 min then concentrated. The residue was suspended in satd. $NaHCO_3$ (aq) and extracted with dichloromethane (×2). The combined organic extracts were dried ($MgSO_4$) and concentrated to give 1-{4-[(cyclopropylmethyl)sulphonyl]phenyl}-1-pyridin-3-ylmethanamine as an oil. To a solution of the crude material in dichloromethane (20 mL) was added 1N NaOH(aq) followed by 2,4-dichlorobenzoyl chloride (350 μL, 2.5 mmol). The reaction mixture was stirred vigorously for 1 h at room temperature, then the layers separated and the organic phase dried ($MgSO_4$) and concentrated to give crude 2,4-dichloro-N-[{4-[(cyclopropylmethyl)thio]phenyl}(pyridin-3-yl)methyl]benzamide. The crude thioether was dissolved in methanol (20 mL) and to this solution was added 1M HCl(aq) (2.5 mL, 2.5 mmol) followed by OXONE (2.58 g, 4.2 mmol). The mixture was stirred at room temperature for 30 min and then quenched with satd. $NaHCO_3$(aq). The product was extracted into dichloromethane (×2) and the combined organic layers dried ($MgSO_4$) and concentrated. The residue was purified by chromatography on silica using gradient elution of 50% EtOAc in hexane to 100% EtOAc to give the title compound as a foam (580 mg, 51% yield over 3 steps). $^1$H NMR δ (500 MHz, $CDCl_3$) δ 8.57-8.56 (2H, m), 7.91 (2H, d, J=8.3 Hz), 7.67 (1H, d, J=8.4 Hz), 7.58 (1H, d, J=8.0 Hz), 7.52 (2H, d, J=8.3 Hz), 7.44 (1H, d, J=1.9 Hz), 7.35-7.29 (2H, m), 7.22 (1H, d, J=7.6 Hz), 6.55 (1H, d, J=7.6 Hz), 3.00 (2H, d, J=7.2 Hz), 1.01-0.93 (1H, m), 0.59-0.55 (2H, m), 0.17-0.14 (2H, m); m/z (ES+) 477 (M+H), 475 (M+H).

Example 54

2,4-Dichloro-N-[{4-[(cyclopropylmethyl)sulphonyl]phenyl}(1-methyl-1,2,5,6-tetrahydropyridin-3-yl)methyl]benzamide

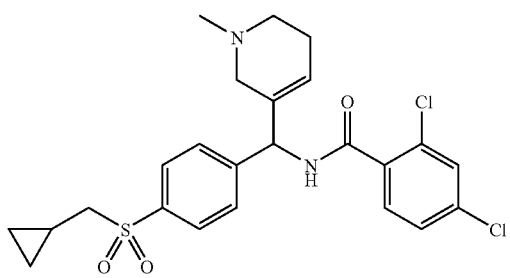

Methyl iodide (263 µL, 4.2 mmol) and 2,4-dichloro-N-[{4-[(cyclopropylmethyl)sulphonyl]phenyl}(pyridin-3-yl)methyl]benzamide (prepared as described in Example 53, 200 mg, 0.42 mmol) were stirred in acetone (4 mL) for 16 h under nitrogen. The resulting yellow suspension was concentrated in vacuo to give 3-{{4-[(cyclopropylmethyl)sulphonyl]phenyl}[(2,4-dichlorobenzoyl)amino]methyl}-1-methylpyridinium iodide. The salt was dissolved in methanol (5 mL) and the solution cooled to −10° C. Sodium borohydride (18 mg, 0.47 mmol) was added and the mixture was stirred at −10° C. for 10 mins and then allowed to warm to room temperature, with stirring, over 1 h. The reaction was quenched with 1N NaOH(aq) (20 mL) and extracted with dichloromethane (2×20 mL). The combined organic extracts were dried (MgSO$_4$) and concentrated. Purification by chromatography on silica eluting with 5% methanol in dichloromethane (+<0.5% ammonia) was followed by salt formation by treatment with ethereal HCl to give the title compound as a white solid (123 mg, 55% yield). m/z (ES+) 495 (M+H), 493 (M+H).

Example 55

2,4-Dichloro-N-[{-4-[(cyclopropylmethyl)sulphonyl]phenyl}(4-fluorophenyl)methyl]-benzamide

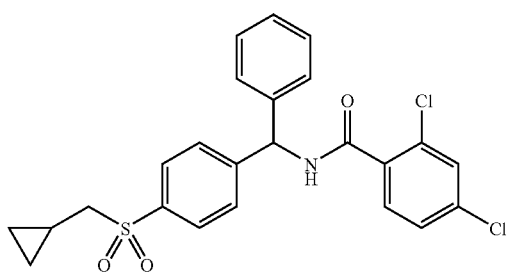

The title compound was prepared from N-((1E)-{4-[(cyclopropylmethyl)thio]phenyl}-methylene)-2-methylpropane-2-sulphinamide using the procedures described in Example 53 but with phenylmagnesium bromide instead of the pyridyl Grignard reagent. $^1$H NMR δ (360 MHz, CDCl$_3$) 7.91 (2H, d, J=8.2 Hz), 7.69 (1H, d, J=8.4 Hz), 7.54 (2H, d, J=8.2 Hz), 7.44 (1H, d, J=1.6 Hz), 7.40-7.32 (4H, m), 7.26-7.25 (2H, m), 7.01 (1H, d, J=7.3 Hz), 6.48 (1H, d, J=7.4 Hz), 3.00 (2H, d, J=7.2 Hz), 1.02-0.93 (1H, m), 0.60-0.55 (2H, m), 0.18-0.14 (2H, m).

Example 56

2,4-Dichloro-N-[{-4-[(cyclopropylmethyl)sulphonyl]phenyl}(4-fluorophenyl)methyl]-benzamide

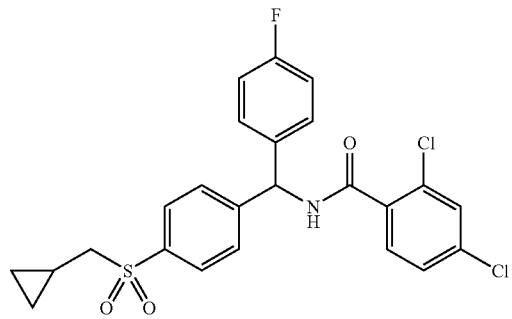

The title compound was prepared from N-((1E)-{4-[(cyclopropylmethyl)thio]phenyl}-methylene)-2-methylpropane-2-sulphinamide using the procedures described in Example 53 but with 4-fluorophenylmagnesium bromide instead of the pyridyl Grignard reagent. $^1$H NMR 8 (500 MHz, CDCl$_3$) 92 (2H, d, J=8.3 Hz), 7.70 (1H, d, J=8.3 Hz), 7.52 (2H, d, J=8.2 Hz), 7.45 (1H, d, J=1.9 Hz), 34 (1H, dd, J=1.9, 8.3 Hz), 7.26-7.22 (2H, m), 7.07 (2H, t, J=8.6 Hz), 6.96 (1H, d, J=7.3 Hz), 48 (1H, d, J=7.4 Hz), 3.01 (2H, d, J=7.2 Hz), 1.03-0.95 (1H, m), 0.60-0.56 (2H, m), 0.18-0.15 (2 m).

Examples 57-64

Those starting materials which were not commercial were prepared as described below.

4,4-Difluorocyclohexanecarbaldehyde

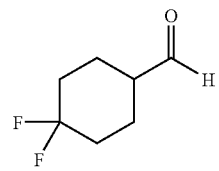

iso-Propylmagnesium chloride (20 mL of a 2.0 M solution in THF, 40 mmol) was added dropwise to a cooled (−15° C.) suspension of ethyl-4,4-difluorocyclohexanecarboxylate (3.0 g, 15.6 mmol) and N,O-methylhydroxylamine hydrochloride (2.28 g, 23.4 mmol) in THF (30 mL). The reaction mixture was stirred for 15 min then quenched with satd. NH$_4$Cl(aq). The product was extracted into ethyl acetate (×2). The combined organic extracts were washed with brine, dried (MgSO$_4$) and concentrated to give 4-difluoro-N-methoxy-N-methylcyclohexanecarboxamide as a clear oil (3.01 g, 93% yield). To a solution of the aforementioned Weinreb amide (3.0 g, 14.5 mmol) in diethyl ether (30 mL) at −78° C. as added, dropwise, diisobutylaluminium hydride (16 mL of a 1.0 M solution in toluene). On completion of addition, the mixture was stirred for a further 15 min before being poured into a stirred mixture of diethyl ether (50 mL), hexanes (50 mL) and 1N HCl(aq) (100 mL). The mixture was stirred or 5 mins and then the layers were separated and the organic phase dried (MgSO$_4$) and concentrated to have 4,4-difluorocyclohexanecarboxaldehyde.

2-Methoxy-4-methyl-6-(trifluoromethyl)nicotinoyl chloride

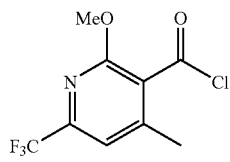

i) Methyl 2-methoxy-4-methyl-6-(trifluoromethyl)nicotinate

A solution of ethyl 2-chloromethyl-6-(trifluoromethyl)nicotinate (1 g, 3.7 mmol) was formed in methanol (20 mL). Sodium methoxide (808 mg, 17 mmol) was added and the mixture heated at reflux for 6 hours. The solution was cooled to room temperature then poured into water (50 mL) and extracted with ethyl acetate (3×50 mL). Combined organics were dried over magnesium sulphate, filtered and evaporated to a brown oil. Purification by flash column chromatography over silica using a 10% ethyl acetate: 90% iso-hexane mixture gave methyl 2-methoxy-4-methyl-6-(trifluoromethyl)nicotinate as a yellow oil: $^1$H NMR (500 MHz, CDCl$_3$): δ 7.13 (1H, s), 4.00 (3H, s), 3.94 (3H, s), 2.36 (3H, s); m/z 250 (M+H$^+$).

ii) 2-Methoxy-4-methyl-6-(trifluoromethyl)nicotinic acid

A solution of methyl 2-methoxy-4-methyl-6-(trifluoromethyl)nicotinate (400 mg, 1.6 mmol) was formed in ethanol (10 mL). A solution of potassium hydroxide (400 mg, 7 mmol) in water (10 mL) was added and the mixture heated at 60° C. for 3 hours. The mixture was cooled in an ice-bath and acidified with aqueous hydrochloric acid (2 N) to approximately pH 3 then extracted with ethyl acetate (3×50 mL). Combined organics were dried over magnesium sulphate, filtered and evaporated to give 2-methoxy-4-methyl-6-(trifluoromethyl)nicotinic acid as a brown solid: $^1$H NMR (400 MHz, CDCl$_3$): δ 7.20 (1H, s), 4.09 (3H, s), 2.55 (3H, s); m/z=236 (M+Ht).

iii) 2-Methoxy-4-methyl-6-(trifluoromethyl)nicotinoyl chloride

Thionyl chloride (2 mL) was added to 2-methoxy-4-methyl-6-(trifluoromethyl)-nicotinic acid (68 mg, 0.29 mmol) and then the mixture was heated at 60° C. for 1 hour. The mixture was evaporated to dryness.

General Procedure for Preparation of Examples 57-64

The compounds were prepared in a manner analogous to Examples 5 and 6 and using the Grignard reagent of Example 7c.

| Example | Structure | m/e (M + 1) |
|---------|-----------|-------------|
| 57 | 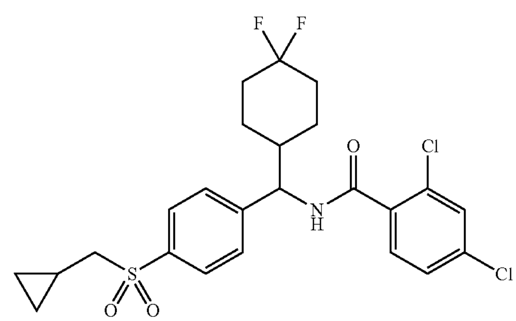 | 518, 516 |
| 58 | 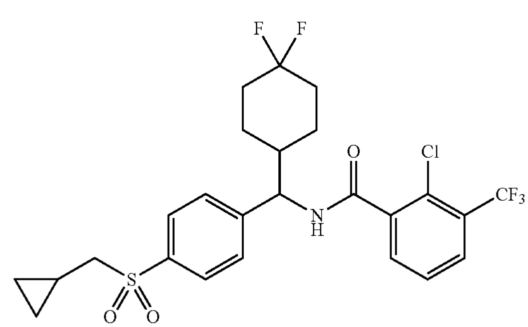 | 552, 550 |

-continued

| Example | Structure | m/e (M + 1) |
|---|---|---|
| 59 | 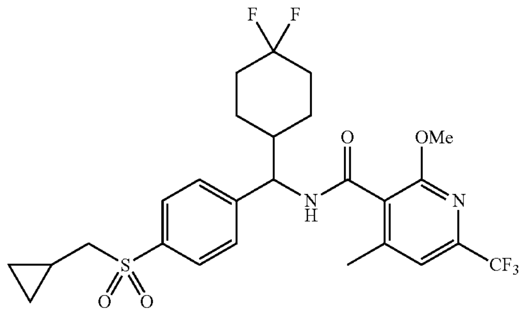 | 561 |
| 60 | 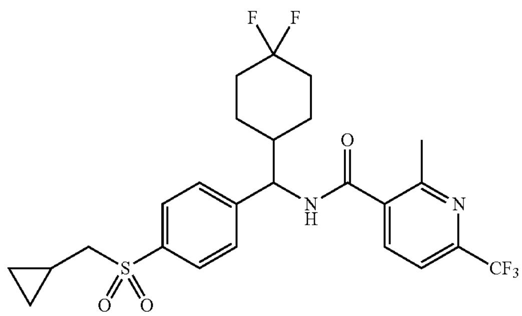 | 531 |
| 61 | 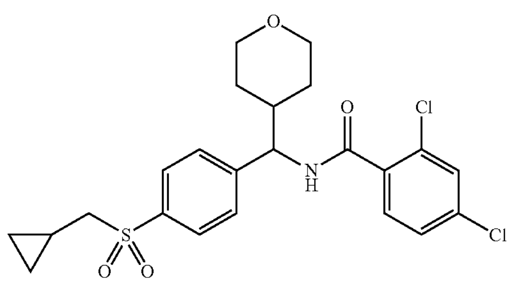 | 484<br>482 |
| 62 | 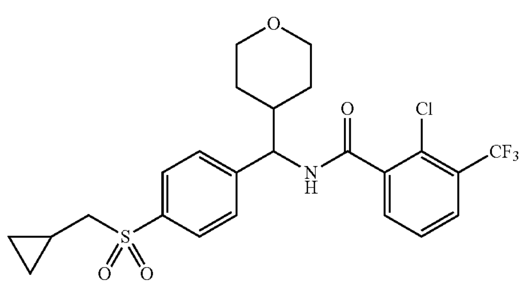 | 518<br>516 |
| 63 | 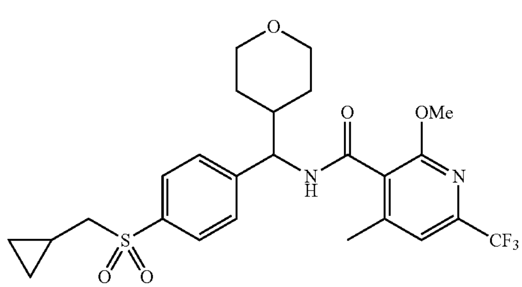 | 527 |

| Example | Structure | m/e (M + 1) |
|---|---|---|
| 64 | | 497 | a) All compounds are racemic

Example 65

2,4-Dichloro-N-(2-cyclopropyl-1-{5-[(cyclopropylmethyl)sulphonyl]-4-methyl-4H-1,2,4-triazol-3-yl}ethyl)benzamide

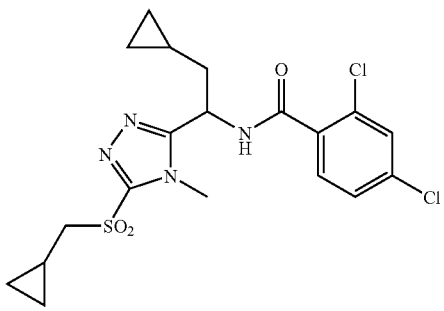

a) 3-[(Cyclopropylmethyl)thio]-4-methyl-4H-1,2,4-triazole

To 4-methyl-4H-1,2,4-triazole-3-thiol (5.2 g, 45 mmol) in absolute ethanol (30 mL) under nitrogen was added (bromomethyl)cyclopropane (4.50 mL, 46 mmol). The reaction was stirred at room temperature for 24 h and then concentrated in vacuo. The residue was partitioned between ethyl acetate and sat aq. $Na_2CO_3$ solution. The layers were separated and the aqueous phase further extracted with ethyl acetate (×3). The combined organic extracts were dried ($MgSO_4$) and concentrated to give the title compound as a colourless oil (4.795 g, 28 mmol). $^1$H NMR (500 MHz, $CDCl_3$) δ (ppm) 8.14 (1H, s), 3.62 (3H, s), 3.17 (2H, d, J=7.3 Hz), 1.27-1.15 (1H, m), 0.63-0.59 (2H, m), 0.30-0.27 (2H, m); m/z (ES+) 170 (M+H).

b) 2-Cyclopropyl-1-{5-[(cyclopropylmethyl)thiol]-meth-4H-1,2,4-triazol-3-yl}ethanone Oxalyl chloride (0.95 mL, 10.9 mmol) was added dropwise to stirred cyclopropylacetic acid (0.94 g, 9.4 mmol) in toluene (12 mL) under nitrogen and the resulting mixture stirred at room temperature for 2 h. To this mixture was added a solution of 3-[(cyclopropylmethyl)thio]-4-methyl-4H-1,2,4-triazole (1.60 g, 9.5 mmol) in toluene (10 mL). The mixture was then stirred vigorously as triethylamine (1.40 mL, 10 mmol) was added dropwise. After 30 min, an additional portion of triethylamine (1.40 mL, 10 mmol) was added and the mixture stirred at room temperature for 2 h and then at reflux for 18 h. Following aqueous work-up, the product was purified to some extent by chromatography on silica eluting with ethyl acetate. Some of the residual starting material was removed from this product by crystallisation from ether; the first crop of solid obtained being starting material. The title compound was used without further purification. In/z (ES+) 252 (M+).

c) 2-Cyclopropyl-1-{5-[(cyclopropylmethyl)thio]-4-methyl-4H-1,2,4-triazol-3-yl}ethanol The crude 2-cyclopropyl-1-{5-[(cyclopropylmethyl)thio]-4-methyl-4H-1,2,4-triazol-3-yl}ethanone (817 mg, 3.25 mmol) was dissolved in methanol (20 mL) and the mixture cooled in an ice bath (4° C.). Sodium borohydride (285 mg, 7.5 mmol) was added portionwise and the reaction mixture stirred at 4° C. for 30 min and then at room temperature for 2 h. Solvent was removed in vacuo and the residue purified by chromatography on silica eluting with ethyl acetate to give the title compound (578 mg, 24% yield over 2 steps). $^1$H NMR (500 MHz, $CDCl_3$) δ (ppm) 4.91 (1H, s), 3.75 (1H, s), 3.65 (3H, s), 3.11 (2H, d, J=7.3 Hz), 1.98-1.90 (1H, m), 1.84-1.78 (1H, m), 1.20-1.12 (1H, m), 0.88-0.80 (1H, m), 0.62-0.58 (2H, m), 0.53-0.43 (2H, m), 0.29-0.26 (2H, m), 0.18-0.12 (1H, m), 0.08-0.04 (1H, m).

d) 3-(1-Chloro-2-cyclopropylethyl)-5-[(cyclopropylmethyl)thio]-4-methyl-H-1,2,4-triazole To a cooled (4° C.) solution of 2-cyclopropyl-1-{5-[(cyclopropylmethyl)thio]-4-methyl-4H-1,2,4-triazol-3-yl}ethanol (382 mg, 1.5 mmol) in dichloromethane (10 mL) was added thionyl chloride (10 mL) followed by N,N-dimethylformamide (3 drops). The mixture was stirred at 4° C. for 15 min then at room temperature for 18 h Solvent was removed in vacuo and the residue azeotroped with toluene. The title compound was used without further purification. m/z (ES+) 272 (M+H).

e) 2-Cyclopropyl-1-{5-[(cyclopropylmethyl)thio]-methyl-4H-1,2,4-triazol-3-yl}ethanamine To a crude solution of the 3-(1-chloro-2-cyclopropylethyl)-5-[(cyclopropylmethyl)thio]-4-methyl-4H-1,2,4-triazole from step d in DMF (3 mL) under nitrogen was added sodium azide (1.0 g, 15 mmol). The mixture was stirred at 65° C. for 20 h, then cooled to room temperature, diluted with water and extracted into ethyl acetate. The organic extract was washed with water and then brine before being dried ($MgSO_4$) and concentrated. The residue was taken up in THF (10 mL), and water (2 mL) was added followed by triphenylphosphine (1.6 g, 6.1 mmol). The reaction mixture was stirred under nitrogen for 5 h, then concentrated in vacuo. The residue was dissolved in methanol and applied to an SCX cartridge. Elution with methanol afforded organophosphorus residues and subsequent elution with 2M ammonia in methanol provided the title amine.

f) 2,4-Dichloro-N-(2-cyclopropyl-1-{5-[(cyclopropylmethyl)thio]-4-methyl-4H-1,2,4-triazol-3-yl}ethyl)benzamide To a solution of the amine obtained in step e in dichloromethane (3 mL) was added 2,4-dichlorobenzoyl chloride (210 µL, 1.5 mmol) and triethylamine (500 µL, 3.6 mmol). The reaction mixture was stirred at room temperature for 6 h. Following aqueous work-up, the residue was purified by chromatography on silica eluting with 40 to 50% ethyl acetate in hexanes to give the title compound. m/z (ES+) 427 (M+H), 425 (M+H).

g) 2,4-Dichloro-N-(2-cyclopropyl-1-{5-[(cyclopropylmethyl)sulphonyl]-4-methyl-4H-1,2,4-triazol-3-yl}ethyl)benzamide To a solution of 2,4-dichloro-N-(2-cyclopropyl-1-{5-[(cyclopropylmethyl)thio]-4-methyl-4H-1,2,4-triazol-3-yl}ethyl)benzamide (158 mg, 0.37 mmol) in DMF (2 mL) was added OXONE (800 mg, 1.3 mmol). The mixture was stirred at room temperature overnight then diluted with ethyl acetate and washed with water (×2). The organic layer was concentrated and the residue purified by chromatography on silica eluting with 40% ethyl acetate in hexane. The title compound crystallised from dichloromethane/diethyl ether/hexanes as a white solid (124 mg). $^1$H NMR (500 MHz, CDCl$_3$) δ (ppm) 7.59 (1H, d, J=8.3 Hz), 7.43 (1H, d, J=1.9 Hz), 7.31 (1H, dd, J=1.9, 8.3 Hz), 7.16 (1H, d, J=8.3 Hz), 5.47 (1H, q, J=7.6 Hz), 4.08 (3H, s), 3.56-3.46 (2H, m), 2.11-1.97 (2H, m), 1.27-1.19 (1H, m), 0.74-0.66 (3H, m), 0.54-0.46 (2H, m), 0.41-0.27 (2H, m), 0.21-0.17 (1H, m), 0.08-0.04 (1H, m); m/z (ES+) 459 (M+H), 457 (M+H).

Example 66

N-(2-Cyclopropyl-1-{5-[(cyclopropylmethyl)sulphonyl]-4-methyl-4H-1,2,4-triazol-3-yl}ethyl-2-methoxy-4-methyl-6-(trifluoromethyl)nicotinamide

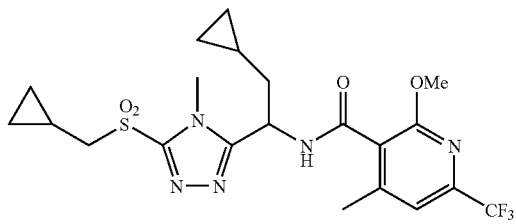

The title compound was prepared from 2-cyclopropyl-1-{5-[(cyclopropylmethyl)thio]-4-methyl-4H-1,2,4-triazol-3-yl}ethanamine (Example 65e) and 2-methoxy-4-methyl-6-trifluoromethyl)nicotinoyl chloride (described above, see Examples 57-64) using the conditions described in Example 65 steps f and g. $^1$H NMR (500 MHz, CDCl$_3$) δ (ppm) 7.15 (1H, s), 6.91 (1H, d, J=5.2 Hz), 5.49 (1H, q, J=7.7 Hz), 4.08 (3H, s), 3.97 (3H, s), 3.58-3.48 (2H, m), 2.40 (3H, s), 2.08-1.98 (2H, m), 1.28-1.20 (1H, m), 0.77-0.67 (3H, m), 0.55-0.47 (2H, m), 0.40-0.32 (2H, m), 0.24-0.18 (1H, m), 0.12-0.06 (1H, m); m/z (ES+) 524 (M+Na), 502 (M+H).

Example 67

N-(2-Cyclopropyl-1-{5-[(cyclopropylmethyl)sulphonyl]-4-methyl-4H-1,2,4-triazol-3-yl}ethyl-2-methyl-6-(trifluoromethyl)nicotinamide

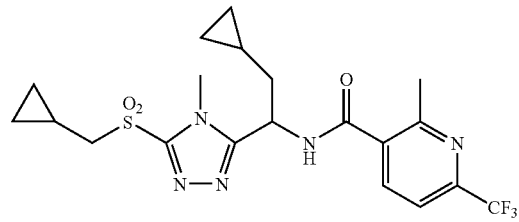

The title compound was prepared from 2-cyclopropyl-1-{5-[(cyclopropylmethyl)thio]-4-methyl-4H-1,2,4-triazol-3-yl}ethanamine (Example 65e) and 2-methyl-6-trifluoromethyl)nicotinoyl chloride using the conditions described for Example 65 steps f and g. $^1$H NMR (500 MHz, CDCl$_3$) δ (ppm) 7.88 (1H, d, J=7.9 Hz), 7.52 (1H, d, J=7.9 Hz), 7.49 (1H, br s), 5.43 (1H, q, J=7.7 Hz), 4.09 (3H, s), 3.51-3.43 (2H, m), 2.70 (3H, s), 2.01-1.91 (2H, m), 1.24-1.16 (1H, m), 0.72-0.66 (2H, m), 0.59-0.45 (3H, m), 0.35-0.29 (2H, m), 0.21-0.15 (1H, m), 0.03-0.00 (1H, m); m/z (ES+) 472 (M+H).

Example 68

2,4-Dichloro-N-(1-{5-[(cyclopropylmethyl)sulphonyl]-4-methyl-4H-1,2,4-triazol-3-yl}-3,3-dimethylbutyl)benzamide

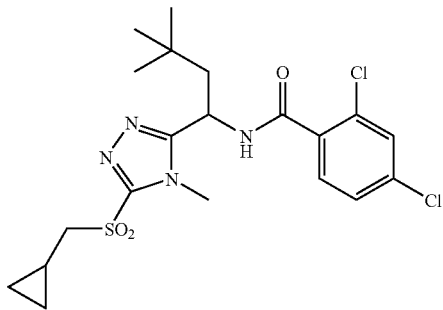

a) 1-{5-[(Cyclopropylmethyl)thio]-4-methyl-4H-1,2,4-triazol-3-yl}-3,3-dimethylbutan-1-ol To 3-[(cyclopropylmethyl)thio]-4-methyl-4H-1,2,4-triazole (822 mg, 4.9 mmol) and 3,3-dimethylbutyraldehyde (1 mL, 8.0 mmol) in dry acetonitrile (12 mL) were added di-tert-butyl dicarbonate (1.3 g, 6.0 mmol), diisopropylethylamine (0.25 mL, 1.4 mmol) and 4-dimethylaminopyridine (50 mg, 0.41 mmol). The mixture was stirred at room temperature for 72 h after which time analysis by mass spectrometry indicated incomplete reaction. Additional di-tert-butyl dicarbonate (0.50 g, 2.3 mmol) was added and the mixture stirred for a further 24 h. Solvent was removed in vacuo and the residue purified by chromatography on silica eluting with 40% ethyl acetate in hexanes to give tert-butyl 1-{5-[(cyclopropylmethyl)thio]-4-methyl-4H-1,2,4-triazol-3-yl}-3,3-dimethylbutyl carbonate. This material was dissolved in dichloromethane (3 mL) and to the resulting solution was added trifluoroacetic acid (3 mL). The mixture was stirred at room temperature for 18 h, then methanol (2 mL) added and the mixture allowed to stand for 3 h. The title compound was obtained following removal of solvent and azeotroping with toluene.

b) 2,4-Dichloro-N-(1-{5-[(cyclopropylmethyl)sulphonyl]-4-methyl-4H-1,2,4-triazol-3-yl}-3,3-dimethylbutyl)benzamide 1-{5-[(Cyclopropylmethyl)thio]-4-methyl-4H-1,2,4-triazol-3-yl}-3,3-dimethylbutan-1-ol was converted to the title compound using the steps outlined in Example 65 steps d-g. $^1$H NMR (500 M, CDCl$_3$) δ (ppm) 7.57 (1H, d, J=8.3 Hz), 7.42 (1H, d, J=1.8 Hz), 7.31 (1H, dd, J=1.9, 8.3 Hz), 6.89 (1H, d, J=8.6 Hz), 5.49-5.45 (1H, m), 4.09 (3H, s), 3.55-3.45 (2H, m), 2.22-2.16 (1H, m), 2.02 (1H, dd, J=7.4, 14.5 Hz), 1.26-1.18 (1H, m), 0.99 (9H, s), 0.70-0.65 (2H, m), 0.37-0.28 (2H, m); m/z (ES+) 475 (M+H), 473 (M+H).

Example 69

N-(1-{5-[(cyclopropylmethyl)sulphonyl]-4-methyl-4H-1,2,4-triazol-3-yl}-3,3-dimethylbutyl)-2-methyl-6-(trifluoromethyl)nicotinamide

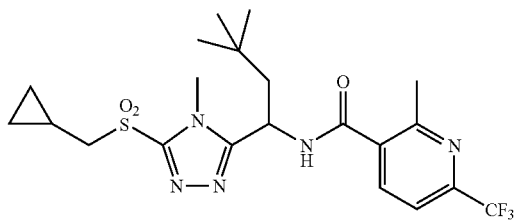

$^1$H NMR (500 MHz, CDCl$_3$) δ (ppm) 7.86 (1H, d, J=7.9 Hz), 7.51 (1H, d, J=7.9 Hz), 7.34 (1H, d, J=8.6 Hz), 5.47-5.43 (1H, m), 4.09 (3H, s), 3.51-3.41 (2H, m), 2.67 (3H, s), 1.96 (2H, d, J=6.5 Hz), 1.23-1.15 (1H, m), 0.98 (9H, s), 0.72-0.65 (2H, m), 0.37-0.28 (2H, m); m/z (ES+) 488 (M+H).

Example 70

N-((1S)-1-{5-[(cyclopropylmethyl)sulphonyl]-4-methyl-4H-1,2,4-triazol-3-yl}-2-morpholin-4-ylethyl)-2-methyl-6-(trifluoromethyl)nicotinamide

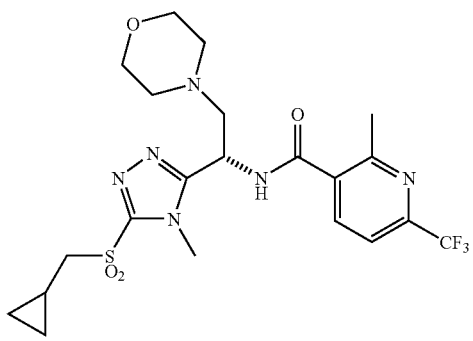

a) Methyl (2S)-2-[(tert-butoxycarbonyl)amino]-3-morpholin-4-ylpropanoate

Methanesulphonyl chloride (0.86 mL, 11 mmol) was added dropwise to a cooled (0° C.), stirred solution of Boc-L-serine methyl ester (2.10 g, 9.6 mmol) and triethylamine (1.53 mL, 11 mmol) in dichloromethane (20 mL) under nitrogen. The mixture was stirred for 45 min, then morpholine (4.5 mL, 52 mmol) was added and the mixture stirred for a further 30 min at 0° C. followed by 1 h at room temperature. Solvent was removed in vacuo and the residue partitioned between ethyl acetate and aq. Na$_2$CO$_3$ solution. The layers were separated and the organic phase concentrated. The residue was azeotroped with toluene and the resulting title compound used without further purification. m/z (ES+) 289 (M+H).

b) tert-Butyl[(1S)-2-hydrazino-1-(morpholin-4-ylmethyl)-2-oxoethyl]carbamate

To a solution of methyl (2S)-2-[(tert-butoxycarbonyl)amino]-3-morpholin-4-ylpropanoate (2.76 g, 9.6 mmol) in methanol (15 mL) under nitrogen was added hydrazine (3.0 mL, 96 mmol). The mixture was allowed to stand at room temperature for 60 h, then the solvent was removed in vacuo and the residue azeotroped with toluene. The title compound was obtained as a colourless foal m/z (ES+) 289 M+H).

c) ((1S)-1-{5-[(cyclopropylmethyl)thio]-4-methyl-4H-1,2,4-triazol-3-yl}-2-morpholin-4-ylethyl)carbamate

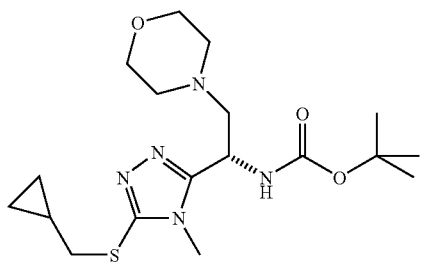

To a solution of crude tert-butyl[(1S)-2-hydrazino-1-(morpholin-4-ylmethyl)-2-oxoethyl]carbamate (2.76 g, 9.6 mmol) in ethanol (25 mL) under nitrogen was added methyl isothiocyanate (0.86 g, 11.8 mmol). The mixture was heated at reflux for 1 h then cooled to room temperature before addition of sodium hydrogencarbonate (8.04 g, 96 mmol). The mixture was heated at reflux for 18 h then cooled to room temperature at which time analysis by mass spectrometry indicated mercaptotriazole formation. Cyclopropylmethyl bromide (1.45 g, 10.7 mmol) was added and the mixture stirred at room temperature for 3 h. Solvent was removed in vacuo and the residue partitioned between ethyl acetate and water. The organic phase was concentrated and the residue purified by chromatography on silica eluting with ethyl acetate followed by 5% methanol in dichloromethane to give the title compound (0.80 g). m/z (ES+) 398 (M+H).

d) (1S)-{5-[(cyclopropylmethyl)sulphinyl]-4-methyl-4H-1,2,4-triazol-3-yl}-2-morpholin-4-ylethanamine bis(trifluoroacetate

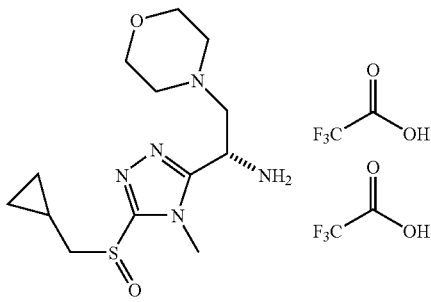

To a cooled (0° C.) solution of ((1S)-1-{5-[(cyclopropylmethyl)thio]-4-methyl-4H-1,2,4-triazol-3-yl}-2-morpholin-4-ylethyl)carbamate (0.80 g, 2.0 mmol) in dichloromethane (10 mL) was added trifluoroacetic acid (0.175 mL, 2.3 mmol) followed my 3-chloroperoxybenzoic acid (0.84 of 77% pure material, 3.75 mmol). The mixture was stirred at 0° C. for 1 h, then partitioned between ethyl acetate and NaHCO$_3$(aq). The layers were separated and the organic phase was washed with NaHCO$_3$(aq) before being concentrated. The residue was redissolved in dichloromethane (10 mL) and then trifluoroacetic acid (10 mL) and methanol (5 mL) added. The mixture was allowed to stand for 18 h, then concentrated in vacuo and azeotroped with toluene to give the title compound. m/z (ES+) 314 (M+H).

e) N-((1S)-1-{5-[(cyclopropylmethyl)sulphonyl]-4-methyl-4H-1,2,4-triazol-3-yl}-2-morpholin-4-ylethyl)-2-methyl-6-(trifluoromethyl)nicotinamide The title compound was prepared from (1S)-1-{5-[(cyclopropylmethyl)sulphinyl]-4-methyl-4H-1,2,4-triazol-3-yl}-2-morpholin-4-ylethanamine bis(trifluoroacetate and 2-methyl-6-(trifluoromethyl)nicotinoyl chloride using the conditions described in Example 65 steps f and g. $^1$H NMR (500 MHz, d$_6$-DMSO) δ (ppm) 9.23 (1H, d, J=8.1 Hz), 7.99 (1H, d, J=7.9 Hz), 7.81 (1H, d, J=7.9 Hz), 5.57-5.53 (1H, m), 3.94 (3H, s), 3.65-3.51 (6H, m), 3.07 (1H, dd, J=9.4, 12.7 Hz), 2.90 (1H, dd, J=5.7, 12.8 Hz), 2.62 (3H, s), 2.61-2.58 (2H, m), 2.51-2.46 (2H, m), 1.06-0.98 (1H, m), 0.56-0.48 (2H, m), 0.22-0.14 (2H, m); m/z (ES+) 517 (M+H).

Example 71

N-((1S)-1-{5-[(cyclopropylmethyl)sulphonyl]-4-methyl-4H-1,2,4-triazol-3-yl}-3,3,3-trifluoropropyl-2-methyl-6-(trifluoromethyl)nicotinamide

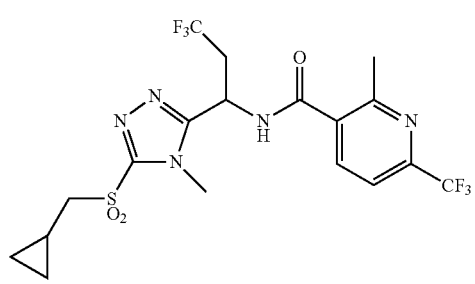

a) tert-Butyl[3,3,3-trifluoro-1-hydrazinocarbonyl)propyl]carbamate

To 2-[(tert-butoxycarbonyl)amino]-4,4,4-trifluorobutanoic acid (1.40 g, 5.4 mmol) in dichloromethane 30 mL) cooled to 4° C. was added 1,1'-carbonyldiimidazole (1.06 g, 6.5 mmol) and the resulting mixture stirred for 1 h. Hydrazine monohydrate (0.955 mL, 19.1 mmol) was added and the mixture stirred for 1 h at 4° C. followed by 72 h at room temperature. The mixture was concentrated in vacuo and the residue azeotroped with toluene. The residue was taken up in ethyl acetate and washed with 10% citric acid aqueous) (×2) before being concentrated in vacuo to give the title compound as a colourless foam. m/z ES+) 216 (M-[Me$_2$C=CH$_2$]), 172 (M-Boc).

b) N-((1S)-1-{5[(cyclopropylmethyl)sulphonyl]-4-methyl-4H-1,2,4-triazol-3-yl}-3,3,3-trifluoropropyl)-2-methyl-6-(trifluoromethyl)nicotinamide The title compound was prepared following the procedures in Example 70 steps c, d and e. $^1$H NMR 500 MHz, CDCl$_3$) δ (ppm) 7.88 (1H, d, J=7.9 Hz), 7.53 (1H, d, J=7.9 Hz), 7.45 (1H, d, J=8.8 Hz), 5.88-5.82 (1H, m), 4.06 (3H, s), 3.37-3.26 (2H, m), 3.13-3.01 (2H, m), 2.72 (3H, s), 1.13-1.05 (1H, m), 0.68-0.60 (2H, m), 0.30-0.24 (1H, m), 0.23-0.17 (1H, m); m/z (ES+) 500 (M+H).

Example 72

2,4-Dichloro-N-{2-cyclobutyl-1-[4-(propylsulphonyl)phenyl]ethyl}benzamide

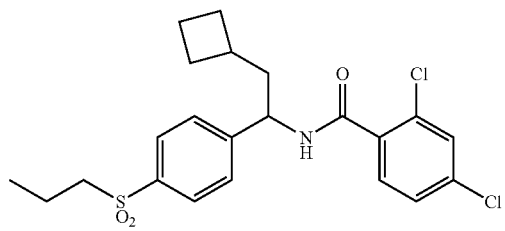

The title compound was prepared in a manner analogous to Example 1 and utilising the reaction of cyclobutylmethylmagnesium bromide with 4-(propylsulphonyl)-benzaldehyde. m/z (ES+) 456 (M+H), 0.54 (M+H).

Example 73

2,4-Dichloro-N-[{-4-[(cyclopropylmethyl)sulphonyl]phenyl}(piperidin-4-yl)methyl]-benzamide

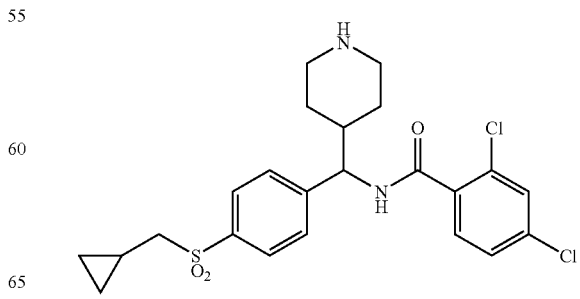

The title compound was prepared from tert-butyl 4-formylpiperidine-1-carboxylate using the method outlined in Examples 5 and 6 and employing the Grignard reagent described in Example 7. m/z (ES+) 483 (M+H), 481 (M+H).

Example 74

2-Chloro-N-[{-4-[(cyclopropylmethyl)sulphonyl]phenyl}(piperidin-4-yl)methyl]-3-(trifluoromethyl)benzamide

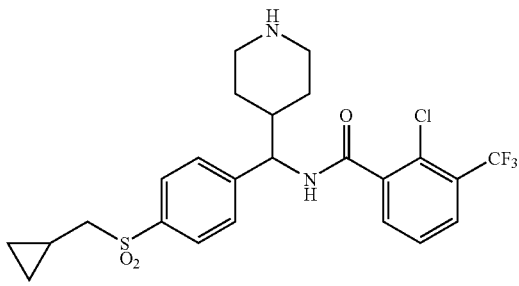

The title compound was prepared from tert-butyl 4-formylpiperidine-1-carboxylate using the method outlined in Examples 5 and 6 and employing the Grignard reagent described in Example 7. m/z (ES+) 517 (M+H), 515 (M+H).

Example 75

(2S,4R)-2-((R)-{[2-Chloro-3-(trifluoromethyl)benzoyl]amino}{4-[(cyclopropyl-methyl)sulphonyl]phenyl}methyl)-4-hydroxypyrrolidinium trifluoroacetate

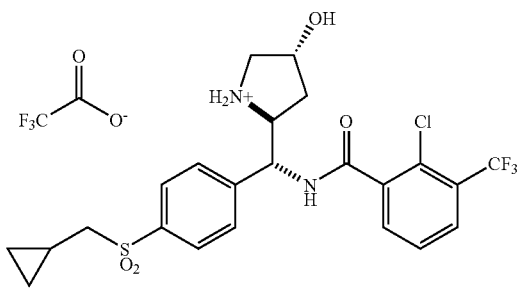

a) tert-Butyl (2S,4R)-2-((R)-{[2-chloro-3-(trifluoromethyl)benzoyl]amino}{4-[(cyclopropylmethyl)sulphonyl]phenyl}methyl)-4-hydroxypyrrolidine-1-carboxylate A mixture of tert-butyl (2S,4R)-4-(benzyloxy)-2-((R)-{[2-chloro-3-(trifluoromethyl)benzoyl]amino}{4-[(cyclopropylmethyl)sulfonyl]phenyl}methyl)-pyrrolidine-1-carboxylate (330 mg, 0.49 mmol) prepared from (2S,4R)-4-(benzyloxy)-1-(tert-butoxycarbonyl)pyrrolidine-2-carboxylic acid using the method outlined for Examples 11-46, DDQ (0.78 g, 3.4 mmol), DCE (25 mL) and water (1.5 mL) was stirred at 60° C. for 10 hours. After cooling to rt, 1,4-cyclohexadiene (0.76 ml) was added. The mixture was stirred for 5 min. and diluted with ether (70 ml). The mixture was washed with sat. aq. NaHCO₃. The organic extract was dried and concentrated. The residue purified by preparative TLC (DCM:MeOH 10%) to give the title product (150 mg, 50%). 1H NMR (CDCl₃) δ (ppm) 9.77 (1H, d, J=5.9 Hz), 7.92 (2H, d, J=8.2 Hz), 7.76 (1H, d, J=7.5 Hz), 7.65 (1H, d, J=6.8 Hz), 7.54 (2H, t, J=8.0 Hz), 7.43 (1H, t, J=7.6 Hz), 5.12 (1H, d, J=6.4 Hz), 4.56 (1H, t, J=7.9 Hz), 3.92 (1H, br s), 3.40 (1H, d, J=12.2 Hz), 3.07-2.97 (2H, m), 2.52 (1H, dd, J=8.6 and 3.8 Hz), 2.32-2.22 (1H, m), 1.93-1.87 (1H, m), 1.49 (9H, s), 1.01 (1H, m), 0.57 (2H, m), 0.14 (2H, m).

b) (2S,4R)-2-((R)-{[2-Chloro-3-(trifluoromethyl)benzoyl]amino}{4-[(cyclopropyl-methyl)sulphonyl]phenyl}methyl)-4-hydroxypyrrolidinium trifluoroacetate The title compound was prepared from tert-butyl (2S,4R)-2-((R)-{[2-chloro-3-(trifluoromethyl)benzoyl]amino} (4-[(cyclopropylmethyl)sulphonyl]phenyl}methyl)-4-hydroxypyrrolidine-1-carboxylate using the deprotection conditions described in Examples 5 and 6 d). m/z (ES+) 517 (M+H).

Example 76

2,4-Dichloro-N-[{4-(cyclopropylmethyl)sulphonyl]phenyl}(1-hydroxycyclopentyl)-methylbenzamide

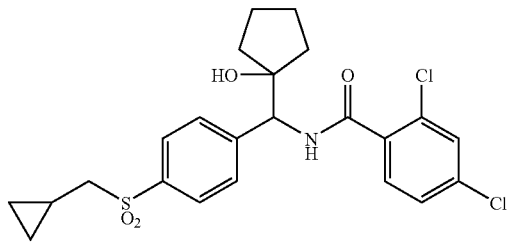

The title compound was prepared in a manner analogous to Example 7 but using cyclopentanone in place of acetone. m/z (ES+) 504 (M+Na), 482 (M+H), 464.

Example 77

2-Chloro-N-[{4-[(cyclopropylmethyl)sulphonyl]phenyl}(1-hydroxycyclopentyl-methyl]-3-(trifluoromethyl)benzamide

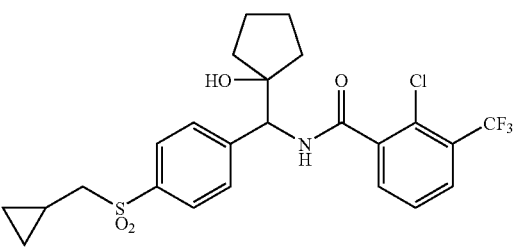

The title compound was prepared in a manner analogous to Example 7 but using cyclopentanone in place of acetone. ¹H NMR (500 MHz, CDCl₃) δ (ppm) 0.20-0.12 (2H, m), 0.62-0.54 (2H, m), 1.04-0.98 (1H, m), 1.12 (1H, t, J=9.4 Hz), 1.78-1.68 (4H, m), 1.97-1.89 (3H, m), 3.09-2.97 (2H, m), 5.12 (1H, d, J=8.2 Hz), 7.22 (1H, s), 7.44 (1H, t, J=7.7 Hz), 7.65 (3H, m), 7.79 (1H, d, J=7.9 Hz), 7.93 (2H, d, J=8.3 Hz).

The invention claimed is:
1. A compound of the formula (Ia):

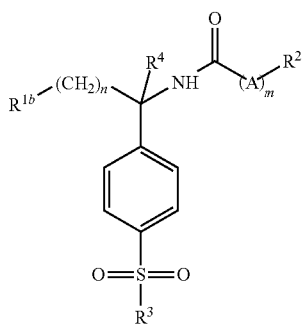

wherein
n is 0-6;
$R^{1b}$ is a $C_{3-6}$ cycloalkyl, which is unsubstituted or substituted with $R^{2a}$, $R^{2b}$ and $R^{2c}$;
$R^2$ is selected from the group consisting of:
(1) phenyl, which is substituted with $R^{2a}$, $R^{2b}$ and $R^{2c}$,
(2) heterocycle, which is substituted with $R^{2a}$, $R^{2b}$ and $R^{2c}$,
(3) $C_{1-8}$alkyl, which is unsubstituted or substituted with 1-6 halogen, hydroxy, $-NR^{10}R^{11}$, phenyl or heterocycle, where the phenyl or heterocycle is substituted with $R^{2a}$, $R^{2b}$ and $R^{2c}$,
(4) $C_{3-6}$cycloalkyl, which is unsubstituted or substituted with 1-6 halogen, hydroxy or $-NR^{10}R^{11}$, and
(5) $-C_{1-6}$alkyl-($C_{3-6}$cycloalkyl), which is unsubstituted or substituted with 1-6 halogen, hydroxy or $-NR^{10}R^{11}$;
$R^{2a}$, $R^{2b}$ and $R^{2c}$ are independently selected from the group consisting of:
(1) hydrogen,
(2) halogen,
(3) $-C_{1-6}$alkyl, which is unsubstituted or substituted with:
 (a) 1-6 halogen,
 (b) phenyl,
 (c) $C_{3-6}$cycloalkyl, or
 (d) $-NR^{10}R^{11}$,
(4) $-O-C_{1-6}$alkyl, which is unsubstituted or substituted with 1-6 halogen,
(5) hydroxy,
(6) $-SCF_3$,
(7) $-SCHF_2$,
(8) $-SCH_3$,
(9) $-CO_2R^9$,
(10) $-CN$,
(11) $-SO_2R^9$,
(12) $-SO_2-NR^{10}R^{11}$,
(13) $-NR^{10}R^{11}$,
(14) $-CONR^{10}R^{11}$, and
(15) $-NO_2$;
$R^3$ is selected from the group consisting of:
(1) $C_{1-6}$alkyl, which is unsubstituted or substituted with 1-6 halogen, hydroxy, $-NR^{10}R^{11}$, or heterocycle, which is substituted with $R^{2a}$, $R^{2b}$ and $R^{2c}$,
(2) $C_{3-6}$cycloalkyl, which is unsubstituted or substituted with 1-6 halogen, hydroxy or $-NR^{10}R^{11}$,
(3) $-C_{1-6}$alkyl-($C_{3-6}$cycloalkyl), which is unsubstituted or substituted with 1-6 halogen, hydroxy or $-NR^{10}R^{11}$,
(4) $-NR^{10}R^{11}$, and
(5) heterocycle, which is substituted with $R^{2a}$, $R^{2b}$ and $R^{2c}$;

$R^4$ is selected from the group consisting of:
(1) hydrogen, and
(2) $C_{1-6}$alkyl, which is unsubstituted or substituted with halogen or hydroxy;
$R^9$ is independently selected from:
(1) hydrogen,
(2) $-C_{1-6}$alkyl, which is unsubstituted or substituted with 1-6 fluoro,
(3) benzyl, and
(4) phenyl;
$R^{10}$ and $R^{11}$ are independently selected from:
(1) hydrogen,
(2) $-C_{1-6}$alkyl, which is unsubstituted or substituted with hydroxy, 1-6 fluoro or $-NR^{12}R^{13}$, where $R^{12}$ and $R^{13}$ are independently selected from hydrogen and $-C_{1-6}$alkyl,
(3) $-C_{3-6}$cycloalkyl, which is unsubstituted or substituted with hydroxy, 1-6 fluoro or $-NR^{12}R^{13}$,
(4) benzyl,
(5) phenyl;
A is selected from the group consisting of:
(1) $-O-$, and
(2) $-NR^{10}-$;
m is zero or one, whereby when m is zero $R^2$ is attached directly to the carbonyl;
or a pharmaceutically acceptable salt thereof.
2. A compound of the formula (Ib):

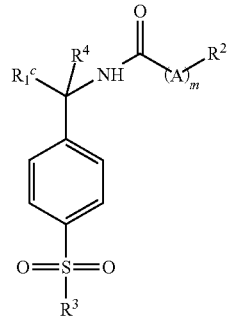

wherein
$R^{1c}$ is a saturated heterocycle, which is unsubstituted or substituted with $R^{2a}$, $R^{2b}$ and $R^{2c}$;
$R^2$ is selected from the group consisting of
(1) phenyl, which is substituted with $R^{2a}$, $R^{2b}$ and $R^{2c}$,
(2) heterocycle, which is substituted with $R^{2a}$, $R^{2b}$ and $R^{2c}$,
(3) $C_{1-8}$alkyl, which is unsubstituted or substituted with 1-6 halogen, hydroxy, $-NR^{10}R^{11}$, phenyl or heterocycle, where the phenyl or heterocycle is substituted with $R^{2a}$, $R^{2b}$ and $R^{2c}$,
(4) $C_{3-6}$cycloalkyl, which is unsubstituted or substituted with 1-6 halogen, hydroxy or $-NR^{10}R^{11}$, and
(5) $-C_{1-6}$alkyl-($C_{3-6}$cycloalkyl), which is unsubstituted or substituted with 1-6 halogen, hydroxy or $-NR^{10}R^{11}$;
$R^{2a}$, $R^{2b}$ and $R^{2c}$ are independently selected from the group consisting of:
(1) hydrogen,
(2) halogen,
(3) $-C_{1-6}$alkyl, which is unsubstituted or substituted with:
 (a) 1-6 halogen,
 (b) phenyl,
 (c) $C_{3-6}$cycloalkyl, or
 (d) $-NR^{10}R^{11}$,
(4) $-O-C_{1-6}$alkyl, which is unsubstituted or substituted with 1-6 halogen, (5) hydroxy,
(6) —$SCF_3$,
(7) —$SCHF_2$,
(8) —$SCH_3$,
(9) —$CO_2R^9$,
(10) —CN,
(11) —$SO_2R^9$,
(12) —$SO_2$—$NR^{10}R^{11}$,
(13) —$NR^{10}R^{11}$,
(14) —$CONR^{10}R^{11}$, and
(15) —$NO_2$;

$R^3$ is selected from the group consisting of:
 (1) $C_{1-6}$alkyl, which is unsubstituted or substituted with 1-6 halogen, hydroxy, —$NR^{10}R^{11}$, or heterocycle, which is substituted with $R^{2a}$, $R^{2b}$ and $R^{2c}$,
 (2) $C_{3-6}$cycloalkyl, which is unsubstituted or substituted with 1-6 halogen, hydroxy or —$NR^{10}R^{11}$,
 (3) —$C_{1-6}$alkyl-($C_{3-6}$cycloalkyl), which is unsubstituted or substituted with 1-6 halogen, hydroxy or —$NR^{10}R^{11}$,
 (4) —$NR^{10}R^{11}$, and
 (5) heterocycle, which is substituted with $R^{2a}$, $R^{2b}$ and $R^{2c}$;

$R^4$ is selected from the group consisting of:
 (1) hydrogen, and
 (2) $C_{1-6}$alkyl, which is unsubstituted or substituted with halogen or hydroxy;

$R^9$ is independently selected from:
 (1) hydrogen,
 (2) —$C_{1-6}$alkyl, which is unsubstituted or substituted with 1-6 fluoro,
 (3) benzyl, and
 (4) phenyl;

$R^{10}$ and $R^{11}$ are independently selected from:
 (1) hydrogen,
 (2) —$C_{1-6}$alkyl, which is unsubstituted or substituted with hydroxy, 1-6 fluoro or —$NR^{12}R^{13}$, where $R^{12}$ and $R^{13}$ are independently selected from hydrogen and —$C_{1-6}$alkyl,
 (3) —$C_{3-6}$cycloalkyl, which is unsubstituted or substituted with hydroxy, 1-6 fluoro or —$NR^{12}R^{13}$,
 (4) benzyl,
 (5) phenyl;

A is selected from the group consisting of
 (1) —O—, and
 (2) —$NR^{10}$—;

m is zero or one, whereby when m is zero $R^2$ is attached directly to the carbonyl;
or a pharmaceutically acceptable salt thereof.

3. A compound of the formula (Id):

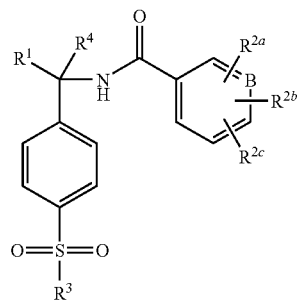

Id wherein
B is CH or N;
$R^{2a}$, $R^{2b}$ and $R^{2c}$ are selected from hydrogen, fluoro, chloro, bromo, $OCH_3$, $CF_3$, $OCF_3$ and $NH_2$;
$R^1$ is —$(CH_2)_n$—$R^{1a}$, wherein n is 0-6, and $R^{1a}$ is selected from the group consisting of
 (1) $C_{1-6}$alkyl or $C_{1-6}$alkenyl, which is unsubstituted or substituted with 1-6 halogen, hydroxy or —$NR^{10}R^{11}$,
 (2) phenyl substituted with $R^{2a}$, $R^{2b}$ and $R^{2c}$,
 (3) heterocycle substituted with $R^{2a}$, $R^{2b}$ and $R^{2c}$,
 (4) $C_{3-6}$cycloalkyl, which is unsubstituted or substituted with $C_{1-6}$alkyl, 1-6 halogen, hydroxy or —$NR^{10}R^{11}$,
 (5) —O—$C_{1-6}$alkyl, which is unsubstituted or substituted with 1-6 halogen, hydroxy or —$NR^{10}R^{11}$,
 (6) —$CO_2R^9$,
 wherein $R^9$ is independently selected from:
  (a) hydrogen,
  (b) —$C_{1-6}$alkyl, which is unsubstituted or substituted with 1-6 fluoro,
  (c) benzyl, and
  (d) phenyl,
 (7) —$NR^{10}R^{11}$,
 wherein $R^{10}$ and $R^{11}$ are independently selected from:
  (a) hydrogen,
  (b) —$C_{1-6}$alkyl, which is unsubstituted or substituted with hydroxy, 1-6 fluoro or —$NR^{12}R^{13}$, where $R^{12}$ and $R^{13}$ are independently selected from hydrogen and —$C_{1-6}$alkyl,
  (c) —$C_{3-6}$cycloalkyl, which is unsubstituted or substituted with hydroxy, 1-6 fluoro or —$NR^{12}R^{13}$,
  (d) benzyl,
  (e) phenyl, and
 (8) —$CONR^{10}R^{11}$;

$R^3$ is selected from the group consisting of:
 (1) $C_{1-6}$alkyl, which is unsubstituted or substituted with 1-6 halogen, hydroxy, —$NR^{10}R^{11}$, or heterocycle, which is substituted with $R^{2a}$, $R^{2b}$ and $R^{2c}$,
 (2) $C_{3-6}$cycloalkyl, which is unsubstituted or substituted with 1-6 halogen, hydroxy or —$NR^{10}R^{11}$,
 (3) —$C_{1-6}$alkyl-($C_{3-6}$cycloalkyl), which is unsubstituted or substituted with 1-6 halogen, hydroxy or —$NR^{10}R^{11}$,
 (4) —$NR^{10}R^{11}$, and
 (5) heterocycle, which is substituted with $R^{2a}$, $R^{2b}$ and $R^{2c}$;

$R^4$ is selected from the group consisting of:
 (1) hydrogen, and
 (2) $C_{1-6}$alkyl, which is unsubstituted or substituted with halogen or hydroxy;

with the proviso that when $R^1$ is methyl, $R^3$ is not methyl;
or a pharmaceutically acceptable salt thereof.

4. A compound of the formula (Ie):

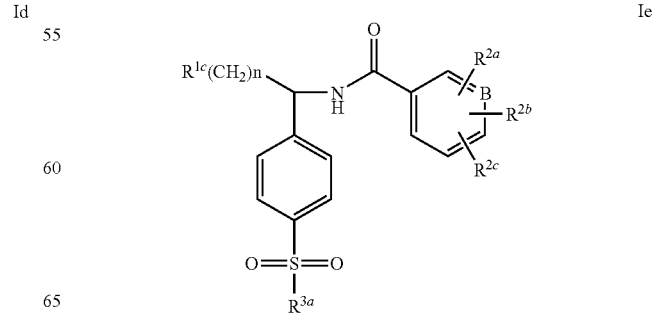

Ie wherein n is 0-6;

B is CH or N;

$R^{2a}$, $R^{2b}$ and $R^{2c}$ are selected from hydrogen, fluoro, chloro, bromo, $OCH_3$, $CF_3$, $OCF_3$ and $NH_2$;

$R^{1c}$ is a saturated heterocycle, which is unsubstituted or substituted with $R^{2a}$, $R^{2b}$ and $R^{2c}$; and $R^{3a}$ is an unsaturated heterocycle optionally substituted by a halogen or a $C_{1-6}$ alkyl or $C_{1-6}$ haloalkyl group;

or a pharmaceutically acceptable salt thereof.

5. The compound of claim 4 wherein the unsaturated heterocycle $R^{3a}$ is triazolyl, pyrazolyl and imidazolyl.

6. A compound of the formula (If):

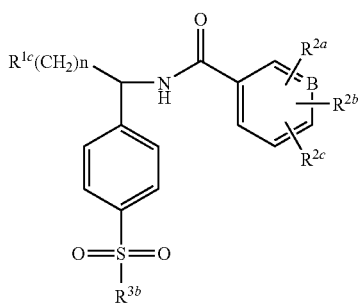

If $R^{1c}$ is a saturated heterocycle, which is unsubstituted or substituted with $R^{2a}$, $R^{2b}$ and $R^{2c}$;

$R^{2a}$, $R^{2b}$ and $R^{2c}$ are selected from hydrogen, fluoro, chloro, bromo, $OCH_3$, $CF_3$, $OCF_3$ and $NH_2$;

n is 0-6; and $R^{3b}$ is a $C_{1-4}$ alkyl group optionally substituted by a cyclopropyl group.

7. The compound of claim 6 wherein $R^{3b}$ is propyl or cyclopropylmethyl.

8. The compound of claim 3 wherein $R^{2a}$, $R^{2b}$ and $R^{2c}$ are selected from hydrogen, fluoro, chloro, bromo and $CF_3$.

9. A pharmaceutical formulation which comprises a compound of claim 1 or a pharmaceutically acceptable salt thereof and a pharmaceutically acceptable carrier.

10. A pharmaceutical formulation which comprises a compound of claim 2 or a pharmaceutically acceptable salt thereof and a pharmaceutically acceptable carrier.

11. A pharmaceutical formulation which comprises a compound of claim 3 or a pharmaceutically acceptable salt thereof and a pharmaceutically acceptable carrier.

* * * * *